US009546151B2

(12) United States Patent
Janowsky et al.

(10) Patent No.: US 9,546,151 B2
(45) Date of Patent: Jan. 17, 2017

(54) VMAT INHIBITORY COMPOUNDS

(71) Applicants: Oregon Health & Science University, Portland, OR (US); United States Department of Veterans Affairs, Washington, DC (US); Organix Inc., Woburn, MA (US)

(72) Inventors: Aaron Janowsky, Portland, OR (US); Peter Meltzer, Woburn, MA (US)

(73) Assignees: Oregon Health & Science University, Portland, OR (US); The United States of America as Represented by the Department of Veteran Affairs, Washington, DC (US); Organix Inc., Woburn, MA (US)

( * ) Notice: Subject to any disclaimer, the term of this patent is extended or adjusted under 35 U.S.C. 154(b) by 0 days.

(21) Appl. No.: 14/815,356

(22) Filed: Jul. 31, 2015

(65) Prior Publication Data

US 2016/0031852 A1    Feb. 4, 2016

Related U.S. Application Data

(60) Provisional application No. 62/031,543, filed on Jul. 31, 2014.

(51) Int. Cl.
| | | |
|---|---|---|
| *C07D 401/06* | (2006.01) | |
| *C07D 409/14* | (2006.01) | |
| *C07D 405/14* | (2006.01) | |
| *C07D 401/14* | (2006.01) | |
| *A61K 31/517* | (2006.01) | |
| *A61K 31/519* | (2006.01) | |
| *A61K 31/506* | (2006.01) | |

(52) U.S. Cl.
CPC ........... *C07D 401/06* (2013.01); *C07D 401/14* (2013.01); *C07D 405/14* (2013.01); *C07D 409/14* (2013.01); *A61K 31/506* (2013.01); *A61K 31/517* (2013.01); *A61K 31/519* (2013.01)

(58) Field of Classification Search
CPC ... A61K 31/517; A61K 31/519; A61K 31/506
USPC ........................................................ 514/260
See application file for complete search history.

(56) References Cited

U.S. PATENT DOCUMENTS

| | | | |
|---|---|---|---|
| 3,274,194 A * | 9/1966 | Hayao | C07D 211/14 540/569 |
| 4,939,137 A | 7/1990 | Russell et al. | |
| 5,296,487 A | 3/1994 | Shimazaki et al. | |
| 2002/0025967 A1 | 2/2002 | Smith | |
| 2003/0109516 A1 | 6/2003 | Fliri et al. | |
| 2011/0105505 A1 | 5/2011 | Stieber et al. | |

FOREIGN PATENT DOCUMENTS

DE    3601731    7/1987

OTHER PUBLICATIONS

Dwoskin et al., "A novel mechanism of action and potential use for lobeline as a treatment for psychostimulant abuse." Biochemical Pharmacology 63, 89 (2002).
Erickson et al, "Distinct pharmacological properties and distribution in neuronsand endocrine cells of two isoforms of the human vesicularmonoamine transporter." Proc Natl Acad Sci U S A 93, 5166-5171 (1992).
Eshleman et al, "Characteristics of Drug Interactions with RecombinantBiogenic Amine Transporters Expressed in the SameCell Type." J Pharmacol Exp Therap 289, 877-885 (1999).
Fleckenstein et al, "Rapid and Reversible Effects of Methamphetamine onDopamine Transporters." J Pharmacol Exp Ther 282, 834-838 (1997).
Fumagalli et al, "Increased Methamphetamine Neurotoxicity in HeterozygousVesicular Monoamine Transporter 2 Knock-Out Mice." J Neurosci 19, 2424-2431. (1999).
German et al, "Pharmacological Inactivation of the Vesicular Monoamine Transporter Can Enhance 1-Methyl-4-Phenyl-1,2,3,6-Tetrahydropyridine-Induced Neurodegeneration of Midbrain Dopaminergic Neurons, But Not Locus Coeruleus Noradrenergic Neurons." Neuroscience 101, 1063-1069 (2000).
Harrod et al, "Lobeline Attenuates d-Methamphetamine Self-Administrationin Rats." J Pharmacol Exp Ther 298, 172-179 (2001).
Hayao et al., "New sedative and hypotensive 3-substituted 2, 4 (1H, 3H)-quinazolinediones," Journal of medicinal chemistry, 1965, vol. 8, No. 6, pp. 807-811.
Henry et al, "Biochemistry and Molecular Biology of the Vesicular Monoamine Transporter From Chromaffin Granules." J Exp Biol 196, 251-262 (1994).
Inoue et al, "Effect of reserpine on the brain uptake of carbon 11 methamphetamine and its N-propagyl derivative, deprenyl." Eur J Nucl Med 17, 121-126 (1990).
Jones et al, "Mechanisms of Amphetamine Action Revealed in Mice Lacking theDopamine Transporter." J Neurosci 18, 1979-1985 (1998).
Kahlig et al, "Amphetamine Regulation of Dopamine Transport : Combined Measurements of Transporter Currents and Transporter Imaging Support the Endocytosis of an Active Carrier." J Biol Chem 279, 8966-8975 (2004).
Kahlig et al, "Regulation of Dopamine Transporter Trafficking by Intracellular Amphetamine." Mol Pharmacol 70, 542-548 (2006).
Kenny et al, "Tetrabenazine in the treatment of hyperkinetic movement disorders." Expert Rev Neurother 6, 7-17 (2006).

(Continued)

*Primary Examiner* — Jennifer M Kim
(74) *Attorney, Agent, or Firm* — Stoel Rives LLP; Zhi-Xiang (Alex) Oh

(57) ABSTRACT

Disclosed herein are compounds that bind to the vesicular monoamine transporter 2 (VMAT2), pharmaceutical compositions comprising those compounds, and methods of treatment using said compounds and pharmaceutical compositions.

19 Claims, No Drawings

(56) References Cited

OTHER PUBLICATIONS

Kokoshka et al, "Nature of methamphetamine-induced rapid and reversible changes indopamine transporters." Eur J Pharmacol 361, 269-275 (1998).
Liu et al., "The Role of Vesicular Transport Proteins in Synaptic Transmission and Neural Degeneration." Ann Rev Neurosci 20, 125-156 (1997).
Melikian, "Neurotransmitter transporter trafficking: endocytosis, recycling,and regulation." Pharmacol Ther 104, 17-27 (2004).
Miller et al, "Lobeline Analogs with Enhanced Affinity and Selectivity forPlasmalemma and Vesicular Monoamine Transporters." J Pharmacol Ther 310, 1035-1045 (2004).
Nirenberg et al, "The vesicular monoamine transporter 2 is present in smallsynaptic vesicles and preferentially localizes to largedense core vesicles in rat solitary tract nuclei." 92, 8773-8777 (1995).
Partilla et al, "Interaction of Amphetamines and Related Compounds at theVesicular Monoamine Transporter." J Pharmacol Exp Ther 319, 237-246 (2006).
Saunders et al, "Amphetamine-induced loss of human dopamine transporter activity: An internalization-dependent and cocaine-sensitive mechanism." Proc Natl Acad Sci U S A 97, 6850-6855 (2000).
Schuldiner et al, "Amphetamine Derivatives Interact with Both Plasma Membrane and Secretory Vesicle Biogenic Amine Transporters." Mol Pharmacol 44, 1227-1231 (1993.
Sonders et al, "Multiple Ionic Conductances of the Human Dopamine Transporter: The Actions of Dopamine and Psychostimulants." J Neurosci 17, 960-974 (1997).

Sulzer et al., "Amphetamine and Other Psychostimulants Reduce pH Gradients in Midbrain Dopaminergic Neurons and Chromaffin Granules: A Mechanism of Action." Neuron 5, 797-808 (1990).
Sulzer et al, "Amphetamine Redistributes Dopamine from Synaptic Vesicles to the Cytosol and Promotes Reverse Transport." J Neurosci 15, 4102-4108 (1995).
Teng et al, "Lobeline and Nicotine Evoke [3H]Overflow from Rat Striatal Slices Preloaded with [3H]Dopamine: Differential Inhibition of Synaptosomal and Vesicular [3H]Dopamine Uptake." J Pharmacol Exp Ther 280, 1432-1444 (1997).
Torres, "The dopamine transporter proteome." J Neurochem 97 Suppl 1, 3-10 (2006).
Vartak et al, "Pyrrolidine Analogues of Lobelane: Relationship of Affinity for the Dihydrotetrabenazine Binding Site with Function of the Vesicular Monoamine Transporter 2 (VMAT2)." J Med Chem 52, 7878 (2009).
Vocci et al, "Approached to the development of medications for the treatment of methamphetamine dependence." Addiction 102 Suppl 1, 96-106 (2007).
Wimalasena, "Vesicular Monoamine Transporters: Sturcture-Function, Pharmacology, and Medicinal Chemistry." Med Res Rev 31, 483-519 (2010).
Zahniser et al, "Chronic and acute regulartion of Na/Cl-dependent neurotransmitter transporters:drugs, substrates, presynaptic receptors, and signaling systems." Pharmacol Ther 92, 21-55 (2001).
Zheng et al, "Vesicular Monoamine Transporter 2: Role as a Novel Target for Drug Development." AAPS J 8, E682-692 (2006).
International Search Report dated May 10, 2016 as received in International Patent Application No. PCT/US2015/043243.

* cited by examiner

VMAT INHIBITORY COMPOUNDS

CROSS-REFERENCE TO RELATED APPLICATIONS

This application claims the benefit of U.S. Provisional Application No. 62/031,543, filed Jul. 31, 2014, which is hereby incorporated by reference in its entirety.

ACKNOWLEDGEMENT OF GOVERNMENT SUPPORT

This work was supported by the United States Government under the terms of Grant # BX000939, awarded by the United States Department of Veterans Affairs. The United States Government has certain rights in this invention.

BACKGROUND

Methamphetamine (MA) is a Schedule II stimulant that has become a highly abused drug in the US. The National Institute on Drug Abuse (NIDA) has reported that about 0.3% of the population, (>730,000) has used methamphetamine, and that children as young as 12 were among those users. Although there are behavioral programs that report a measure of success in treating addicts, there are currently no medications approved for the treatment of MA addiction. Drugs such as methamphetamine bind to vesicular monoamine transporter 2 (VMAT2), also known as solute carrier family 18 member 2 (SLC18A2) and block the vesicular uptake of neurotransmitters. VMAT2 sequesters neurotransmitters into cytoplasmic vesicles following uptake by plasma membrane transporters on presynaptic nerve terminals. In addition, methamphetamine serves as a substrate for VMAT2 and plasma membrane transporters, substituting for the neurotransmitters, and causing their release from vesicular pools. The subsequent increase in synaptic neurotransmitter availability is the foundation for methamphetamine's psychostimulant effects.

VMAT2 is located presynaptically on intracellular storage vesicles and monoaminergic nerve terminals. VMAT2 has been cloned and is comprised of 515 amino acids putatively arranged in 12 interconnected helices. The tertiary structure is not known. VMAT2 facilitates uptake of dopamine (DA) into vesicles, where it is stored and later released to maintain physiological concentrations of DA in the synapse. Indeed, without this storage capacity, physiological DA demands cannot be met by intracellular synthesis alone. MA, a VMAT2 substrate, causes the release of DA from vesicles into the cytosol of presynaptic neurons. It then affects the further release of DA into the extracellular space by physiological neuronal firing or by reverse transport by the DA transporter (DAT). The result is an increase of DA in the synapse (Dwoskin L P and Crooks P A Biochemical Pharmacology 63, 89 (2002) and Sulzer D et al, J Neurosci 15, 4102 (1995); both of which are incorporated by reference herein). This increase is the foundation for methamphetamine's psychostimulant effects which may lead to methamphetamine addiction (Wimalasena K, Med Res Rev 31, 483-519 (2010); Zheng G et al, AAPS Journal 8, E682 (2006); and Vartak A P et al, J Med Chem 52, 7878 (2009); all of which are incorporated by reference herein).

Reserpine, an alkaloid that inhibits neurotransmitter uptake into vesicles by VMAT2, binds with high affinity but in an essentially irreversible fashion to a site that is closely associated with the uptake site. Although it has been used extensively as an antihypertensive agent, reserpine's irreversible binding properties make it less clinically attractive as a potential pharmacotherapy for treatment of symptoms associated with MA abuse. Other drugs such as tetrabenazine (TBZ) analogues bind with high affinity to a site on the VMAT2 that apparently differs from the reserpine binding site, and they are under scrutiny as potential medications for the treatment of symptoms associated with psychostimulant abuse.

SUMMARY

Currently, there are no approved pharmacotherapies to relieve craving for or symptoms associated with methamphetamine (MA) abuse and addiction. What is needed is a class of compounds that potently block VMAT2 function, bind weakly to the TBZ binding site, and have low affinity for other neurotransmitter receptors and transporters. Such compounds would represent a new class of anti-MA treatment medications.

The compounds described herein rely on a novel VMAT2 binding site for functional effects and therefore afford an opportunity to construct molecules that differ in binding and pharmacological profiles from those already in exploration as anti-MA pharmacotherapies.

In one aspect, provided herein are compounds of Formula I:

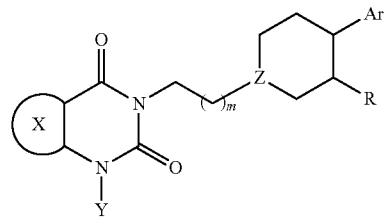

wherein
X is a substituted or unsubstituted 5- or 6-membered aryl or substituted or unsubstituted 5- or 6-membered heteroaryl,
Z is N or CH,
m is 1, 2, or 3,
Ar is substituted or unsubstituted 5- or 6-membered aryl or substituted or unsubstituted 5- or 6-membered heteroaryl,
R is H, ethyl ester, isopropyl ester, —C(O)-alkyl (i.e., methyl ketone, ethyl ketone, etc.), or substituted or unsubstituted 5-membered heteroaryl, and
Y is H, substituted or unsubstituted alkyl, substituted or unsubstituted aryl, or substituted or unsubstituted heteroaryl;
wherein the bond between the carbon atoms bearing Ar and R is a single or double bond,
or a pharmaceutically acceptable salt, solvate, hydrate, stereoisomer, mixture of stereoisomers, crystal form, isomer, or isotopomer thereof.

In some embodiments, the compound has the structure:

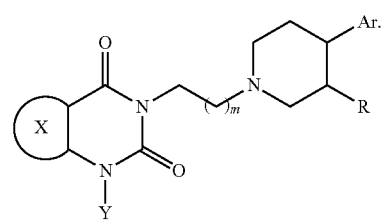

In some embodiments, the bond between the carbon atoms bearing Ar and R is a single bond, and the groups labeled Ar and R are in an RR configuration, an SS configuration, an SR configuration, or an RS configuration. In some embodiments, the bond between the carbon atoms bearing Ar and R is a double bond.

In some embodiments, R is —C(O)-alkyl (i.e., methyl ketone, ethyl ketone, etc.). In some embodiments, R is ethyl ester. In some embodiments, Ar is phenyl, substituted phenyl, pyrrolyl, substituted pyrrolyl, pyridinyl, substituted pyridinyl, thiophene-yl, substituted thiophene-yl, or [1,4]-dioxinyl.

In some embodiments, the compound has the structure:

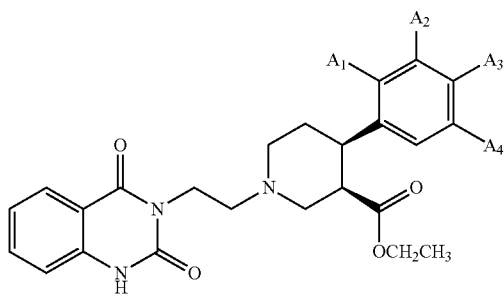

wherein $A_1$, $A_2$, $A_3$, and $A_4$ are independently H, alkyl, substituted alkyl, aryl, substituted aryl, halo, alkoxy, haloalkyl, haloalkoxy, ester, keto, hydroxyl, amino, substituted amino, amido, or nitro. In some embodiments, $A_1$, $A_2$, $A_3$, and $A_4$ are independently H, methyl, ethyl, isopropyl, [1,4]dioxin-5-yl, fluoro, chloro, trifluoromethyl, amino, dimethylamino, methylamido, nitro, azo, benzyl, 2-phenyl ethyl, pyrrolyl, ethyl ester, 1-hydroxyethyl, hydroxyl, methoxy, trifluoromethoxy, or tert-butoxycarbonylamino. In some embodiments, $A_1$ and $A_2$ are H, and $A_3$ and $A_4$ are independently H, fluoro, or trifluoromethyl.

In some embodiments, the compound has the structure:

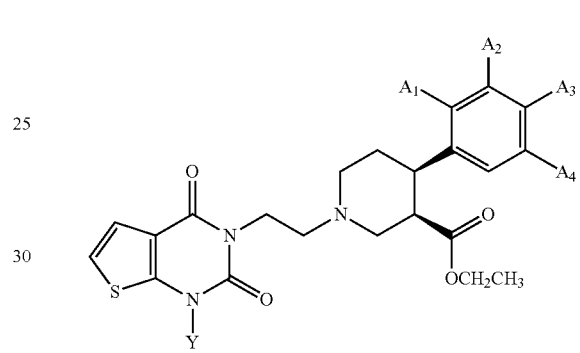

wherein $A_3$ is halo, and m is 2 or 3. In some embodiments, $A_3$ is fluoro.

In some embodiments, the compound has the structure:

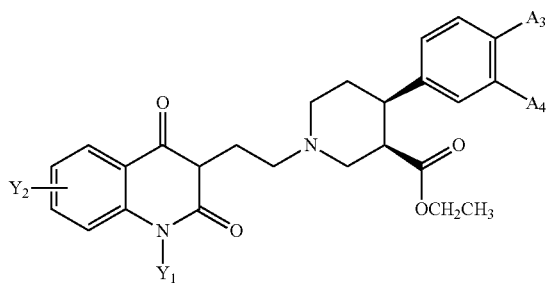

wherein $Y_1$ is H, methyl, ethyl, or 2-benzylethyl, wherein $Y_2$ is H or halo, and wherein $A_3$ and $A_4$ are independently H or halo.

In some embodiments, the compound has the structure:

wherein $A_1$, $A_2$, $A_3$, and $A_4$ are independently H, halo, or haloalkyl, and wherein Y is H or alkyl. In some embodiments, Y is H, $A_1$ and $A_2$ are H, and $A_3$ and $A_4$ are independently H, fluoro, or trifluoromethyl.

In another aspect, provided herein is a pharmaceutical composition comprising one or more compounds described herein, or a pharmaceutically acceptable salt thereof, and one or more pharmaceutically acceptable excipients.

In another aspect, provided herein is a method of treating methamphetamine addiction, the method comprising administering a therapeutically effective amount of a composition described herein to a subject in need thereof.

In another aspect, provided herein is the use of a composition described herein in treating methamphetamine addiction.

DETAILED DESCRIPTION

I—Definitions

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as X, R, Q, and Ar, including all subvariables thereof (such as X1, X2, etc.) used throughout the disclosure are the same variables as previously defined unless stated to the contrary.

"Administration of" and "administering a" compound refers to providing a compound, a prodrug of a compound, or a pharmaceutical composition comprising a compound as described herein. The compound or composition can be administered by another person to the subject or it can be self-administered by the subject.

The term "alkyl" refers to a branched or unbranched saturated hydrocarbon group, such as, without limitation, methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms ($C_{1-6}$ alkyl). The term "alkyl" also includes cycloalkyl. The term "substituted alkyl" refers to an alkyl group wherein one or more hydrogen atoms are replaced with a substituent such as, without limitation, halogen, cycloalkyl, alkoxy, amino, hydroxyl, aryl, or carboxyl.

The term "alkylamino" refers to any straight-chain alkylamino, branched-chain alkylamino, cycloalkylamino, cyclic alkylamino, heteroatom-unsubstituted alkylamino, heteroatom-substituted alkylamino, heteroatom-unsubstituted $C_{1-6}$-alkylamino, and heteroatom-substituted $C_{1-6}$-alkylamino. The term "heteroatom-unsubstituted $C_{1-6}$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_{1-10}$-alkylamino" includes groups, having the structure —NHR, in which R is a heteroatom-unsubstituted $C_{1-10}$-alkyl, as that term is defined above. A heteroatom-unsubstituted alkylamino group would include, without limitation, —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl.

The term "alkoxy" refers to an alkyl group attached to an oxygen atom to form an ether. The term "substituted alkoxy" refers to an alkoxy group wherein one or more hydrogen atoms are replaced with a substituent such as, without limitation, halogen, cycloalkyl, alkoxy, amino, hydroxyl, aryl, or carboxyl.

The term "aryl" refers to any carbon-based aromatic group including, but not limited to, benzene, naphthalene, and phenyl. The term "heteroaryl" is defined as an aromatic group that has at least one heteroatom incorporated within the ring of the aromatic group, including, but not limited to, oxazole. Examples of heteroatoms include, but are not limited to, nitrogen, oxygen, sulfur, and phosphorous. The terms "substituted aryl" and "substituted heteroaryl" refer to an aryl group or heteroaryl group that is substituted with one or more groups including, but not limited to, alkyl, alkynyl, alkenyl, aryl, halide, nitro, amino, ester, ether, ketone, aldehyde, hydroxy, carboxylic acid, cyano, amido, haloalkyl, haloalkoxy, or alkoxy.

"Carboxyl" refers to a —COOH radical. Substituted carboxyl refers to —COOR where R is aliphatic, heteroaliphatic, alkyl, heteroalkyl, or a carboxylic acid or ester. One such substituted carboxyl is an ethyl ester group which is a —COO—CH$_2$—CH$_3$ group.

The term "cycloalkyl" refers to a non-aromatic carbon-based ring composed of at least three carbon atoms. Examples of cycloalkyl groups include, but are not limited to, cyclopropyl, cyclobutyl, cyclopentyl, and cyclohexyl. The term "heterocycloalkyl group," is a cycloalkyl group as defined above where at least one of the carbon atoms of the ring is replaced with a heteroatom such as nitrogen, oxygen, sulfur, or phosphorous.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups replaced with a halogen (F, Cl, Br, I). A halogenated ether refers to a group in which one or more hydrogen atoms present on an ether, such as a methyl ether (—OCH$_3$), is replaced with one or more halogens. For example, a trifluoromethyl ether has a formula of —OCF$_3$.

"Heterocycle" means any saturated, unsaturated or aromatic cyclic moiety wherein said cyclic moiety contains at least one heteroatom selected from of the group consisting of oxygen (O), sulfur (S), phosphorus (P) and nitrogen (N). Heterocycles may be monocyclic or polycyclic rings. The term "substituted heterocycle" refers to an aryl group that is substituted with one or more groups including, but not limited to, halogen, alkyl, halogenated $C_{1-6}$ alkyl, alkoxy, halogenated $C_{1-6}$ alkoxy, amino, amidino, amido, azido, cyano, guanidino, hydroxyl, nitro, nitroso, urea, OS(O)$_2$R, OS(O)$_2$OR, S(O)$_2$OR, S(O)$_{0-2}$R, or C(O)OR wherein R may be H, alkyl, aryl or any 3 to 10 membered heterocycle; OP(O)OR$_1$OR$_2$, P(O)OR$_1$OR$_2$, SO$_2$, NR$_1$R$_2$, NR$_1$SO$_2$R$_2$, C(R$_1$)NR$_2$, or C(R$_1$)NOR$_2$, wherein R$_1$ and R$_2$ may be independently H, alkyl, aryl or 3 to 10 membered heterocycle; NR$_1$C(O)R$_2$, NR$_1$C(O)OR$_2$, NR$_3$C(O)NR$_2$R$_1$, C(O)NR$_1$R$_2$, or OC(O)NR$_1$R$_2$, wherein R$_1$, R$_2$ and R$_3$ are each independently selected from H, alkyl, aryl or 3 to 10 membered heterocycle, or R$_1$ and R$_2$ are taken together with the atoms to which they are attached to form a 3 to 10 membered heterocycle.

Exemplary substituents of a heterocycle further include halogen (Br, Cl, I or F), cyano, nitro, oxo, amino, alkyl (e.g., CH$_3$, C$_2$H$_5$, isopropyl, etc.); alkoxy (e.g., OCH$_3$, OC$_2$H$_5$, etc.); halogenated alkyl (e.g., CF$_3$, CHF$_2$, etc.); halogenated alkoxy (e.g., OCF$_3$, OC$_2$F$_5$, etc.); COOH, COO-alkyl, CO-alkyl, alkyl-S (e.g., CH$_3$S, C$_2$H$_5$S, etc); halogenated alkyl —S (e.g., CF$_3$S, C$_2$F$_5$S, etc.); benzyloxy and pyrazolyl I.

Exemplary heterocycles include, but are not limited to, azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyridinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

The terms "treatment", "treat" and "treating" refer to a therapeutic intervention that ameliorates a sign or symptom of a disease or pathological condition after it has begun to develop. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

A "prophylactic" treatment is a treatment administered to a subject who does not exhibit signs of a disease or exhibits only early signs, for the purpose of decreasing the risk of developing pathology.

"Coadminister" means that each of at least two compounds are administered during a time frame wherein the respective periods of biological activity overlap. Thus, the term includes sequential as well as coextensive administration of two or more drug compounds.

"Optional" or "optionally" means that the subsequently described event or circumstance can but need not occur, and that the description includes instances where said event or circumstance occurs and instances where it does not.

The terms "pharmaceutically acceptable salt" or "pharmacologically acceptable salt" refers to salts prepared by conventional means, and include basic salts of inorganic and organic acids, such as, without limitation, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid. "Pharmaceutically acceptable salts" of the presently disclosed compounds also include those formed from cations such as, without limitation, sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reaction of the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Descriptions of exemplary pharmaceutically acceptable salts can be found in Stahl and Wermuth, Eds., *Handbook of Pharmaceutical Salts; Properties, Selection and Use*, Wiley VCH (2008). When compounds disclosed herein include an acidic function such as a carboxy group, then suitable pharmaceutically acceptable cation pairs for the carboxy group are well known to those skilled in the art and include, without limitation, alkaline, alkaline earth, ammonium, and quaternary ammonium cations. Such salts are known to those of skill in the art. For additional examples of pharmacologically acceptable salts, see Berge et al, *J. Pharm. Sci.* 66:1 (1977).

"Saturated or unsaturated" includes substituents saturated with hydrogens, substituents completely unsaturated with hydrogens and substituents partially saturated with hydrogens.

The term "subject" includes both human and veterinary subjects.

A "therapeutically effective amount" or refers to a quantity of a specified agent sufficient to achieve a desired effect in a subject being treated with that agent. Ideally, a therapeutically effective amount of an agent is an amount sufficient to inhibit or treat the disease without causing substantial toxicity in the subject. The therapeutically effective amount of an agent will be dependent on the subject being treated, the severity of the affliction, and the manner of administration of the therapeutic composition. Methods of determining a therapeutically effective amount of the disclosed compound sufficient to achieve a desired effect in a subject will be understood by those of skill in the art in light of this disclosure.

II—The Dopamine Transporter

Presynaptic transporters are the primary mechanism by which neurotransmitters are deactivated following their physiological release from nerve terminals. MA induces DA transporter (DAT)-associated, Na+-dependent ion currents, suggesting that the drug is a transporter substrate, i.e., it substitutes for DA and is taken up into the cell by the DAT (Sonders M S et al, *J Neurosci* 17, 960-974 (1997); incorporated by reference herein). Additionally, it is a substrate for the serotonin (5-HT) transporter (SERT) and the norepinephrine (NE) transporter (NET). In rats, DAT activity decreases 1 hour after administration of a single dose of MA but recovers after 24 hours (Fleckenstein A E et al, *J Pharmacol Exp Ther* 282, 834-838 (1997); incorporated by reference herein). With repeated multiple high doses of MA, DAT activity and density are rapidly reduced and recover very slowly (Kokoshka J M et al, *Eur J Pharmacol* 361, 269-275 (1998).

Amphetamine redistributes the DA transporter (DAT) away from the cell surface (Saunders C et al, *Proc Natl Acad Sci USA* 97, 6850-6855 (2000); incorporated by reference herein), a trafficking that is paralleled temporally by the loss of DAT activity (Kahlig K M et al, *J Biol Chem* 279, 8966-8975 (2004); incorporated by reference herein) and may require intracellular amphetamine for regulation (Kahlig K M et al, *Mol Pharmacol* 70, 542-548 (2006); incorporated by reference herein). Thus, MA interferes with DA deactivation and the physiological function of the DAT.

The spatial and temporal signaling and synaptic and extra-synaptic concentrations of biogenic amine neurotransmitters are regulated in part by the DAT, SERT and NET. The transporters are members of the 12-transmembrane domain sodium-chloride dependent transporters, and are the targets of therapeutics for depression as well as for abused drugs such as cocaine and MA (Zahniser N R and Doolen S, *Pharmacol Ther* 92, 21-55 (2001); incorporated by reference herein). As reviewed by Torres (Torres G E, *J Neurochem* 97 Suppl 1, 3-10 (2006); incorporated by reference herein), interactions of the DAT with multiple proteins may be important for the assembly, targeting, trafficking or regulation of function. Evidence supports the model of the DAT functioning as an oligomeric complex, which must be targeted to specialized domains within neurons. Second messenger systems, including protein kinase A, protein kinase C, phosphatases, and arachidonic acid regulate activity. Protein kinase C downregulates DAT by increasing the rate of DAT internalization and substrates including DA and amphetamine induce internalization of DAT (Melikian H E, *Pharmacol Ther* 104, 17-27 (2004); incorporated by reference herein). The DAT interacts with PICK1 (Protein Interacting with C kinase 1), the focal adhesion protein Hic-5, synaptosome-associated protein 25 kDA (SNAP-25), synuclein, receptor for activated C kinase-1 (RACK1), syntaxin, protein phosphatase PP2A and PKC-βII.

III—VMAT2: The Vesicular Monoamine Transporter

Once taken up into the cell by the DAT, SERT or NET, MA and neurotransmitters interact with a vesicular monoamine transporter (VMAT2) in the membrane of intracellular vesicles. The VMAT2 is found in monoaminergic pre-synaptic neurons, as well as in peripheral tissues. The VMAT2 pumps cytosolic DA, serotonin (5-HT) and norepinephrine (NE) into several types of vesicles. It functions as an antiporter, with two protons being counterported for each biogenic amine molecule; the proton gradient is maintained by an ATP-dependent proton pump (reviewed in Henry J P et al, *J Exp Biol* 196, 251-262 (1994); incorporated by reference herein). Using the proton gradient, the VMAT2 in chromaffin cells can develop a monoamine concentration gradient greater than 10,000 (Liu Y and Edwards R H, *Ann Rev Neurosci* 20, 125-156 (1997); incorporated by reference herein). To put this in context, a vesicle with an internal diameter of 30 nm has a volume of $1.4 \times 10^{-20}$ liter, and one molecule in this compartment results in a concentration of ~100 μM (Wallace L J and Connell L E, *Synapse* 62, 370-378 (2008); incorporated by reference herein). In axons, VMAT2 is found in synaptic vesicles and large dense-core vesicles, while in cell bodies and dendrites the VMAT2 is found on tubulovesicular structures (Nirenberg M J et al, 92, 8773-8777 (1995); incorporated by reference herein). Because expression varies across brain regions, a recombinant cell system is a useful tool for screening drugs that interact with the VMAT2.

The cloning of VMAT2 (Erickson J D et al, *Proc Natl Acad Sci USA* 93, 5166-5171 (1992); incorporated by reference herein) revealed no sequence homology with the biogenic amine plasma membrane transporters, but some structural similarities were identified, including 12 putative transmembrane domains, glycosylation sites, and several consensus sequences for phosphorylation by kinases. The human (h)VMAT2 is abundantly expressed in monoaminergic cell bodies of brain, in the stomach, and in the adrenal medulla. The hVMAT2 has N and C terminal domains located in the cytoplasm and glycosylation sites facing the vesicle lumen. VMAT2 function is inhibited by the G-protein Gαo2 by an interaction with the first luminal domain (Brunk I et al, *J Biol Chem* 281, 33373-33385 (2006); incorporated by reference herein). By transporting neurotransmitter into vesicles, the VMAT2 participates in the regulation of cytosolic levels and vesicular stores of biogenic amines.

The VMAT2 is neuroprotective; pharmacological blockade of VMAT2 enhances 1-methyl-4-phenylpyridinium (MPP+)- and MA-induced DAergic neuronal toxicity (German D C et al, *Neuroscience* 101, 1063-1069 (2000); incorporated by reference herein), suggesting that VMAT2 protects neurons from some exogenous toxins by facilitating sequestration of the toxins within vesicles. Mice heterozygous for a null VMAT2 mutation are more sensitive to MA toxicity (Fumagalli F et al, *J Neurosci* 19, 2424-2431. (1999); incorporated by reference herein). Vocci F J and Appel N M, *Addiction* 102 Suppl 1, 96-106 (2007) (incorporated by reference herein) reviewed possible targets for MA pharmacotherapies and identified the VMAT2 as having an obligatory role in MA activity. By interfering with the ability of neuronal vesicles to transport and accumulate biogenic amines, MA alters both cytosolic and impulse-regulated extracellular concentrations of neurotransmitters.

Given the current state of the art, it is unclear how MA gains access to synaptic vesicles: by diffusion, by transport via the VMAT2, some combination of the two, or an unknown mechanism. MA is a base with a pKa of 9.8 and is therefore more than 99% protonated at physiological pH. This form is transported by the plasmalemmal transporters. However, MA is highly lipophilic in the neutral state, and can enter cells in the absence of cell-surface transporters and can enter vesicles from the cytosol across membranes (Sulzer D et al, *J Neurosci* 15, 4102-4108 (1995); incorporated by reference herein). The uncharged MA in the vesicle could then act as a weak base, bind to free protons, and dissipate the pH gradient (Sulzer D and Rayport S, *Neuron* 5, 797-808 (1990); incorporated by reference herein). With an increased pH in the vesicle, more neurotransmitter would be unprotonated and able to leave the vesicle across the membranes (Cubells J F et al, *J Neurosci* 14, 2260-2271 (1994); incorporated by reference herein).

MA requires the cell-surface transporter to release transmitter to the extracellular space, as confirmed by studies using DAT knockout animals (Jones S R et al, *J Neurosci* 18, 1979-1985 (1998); incorporated by reference herein). Consistent with this model, the amphetamine derivative fenfluramine causes efflux of neurotransmitter from chromaffin granules at concentrations above those necessary for disrupting the intragranule pH (Schuldiner S et al, *Mol Pharmacol* 44, 1227-1231 (1993); incorporated by reference herein).

In contrast, Partilla J S et al, *J Pharmacol Exp Ther* 319, 237-246 (2006); (incorporated by reference herein) concluded that MA's primary interaction is as a substrate of the VMAT2 and release is primarily via carrier-mediated exchange mechanisms. Consistent with this observation, pretreatment with reserpine results in a significant decrease in initial brain uptake of 2 stereoisomers of [$^{11}$C]MA (Inoue O et al, *Eur J Nucl Med* 17, 121-126 (1990); incorporated by reference herein).

MA interacts directly with the VMAT2, as evidenced by inhibition of [$^3$H]DTBZ binding, albeit at high concentrations (1.2 mM). As a VMAT2 substrate, MA could facilitate release of preloaded neurotransmitter via the VMAT2 in addition to its action as a weak base.

IV—VMAT2 Inhibitors

One VMAT2 inhibitor, reserpine (Methyl (3β,16β,17α, 18β,20α)-11, 17-dimethoxy-18-[(3,4,5-trimethoxybenzoyl) oxy]yohimban-16-carboxylate) binds with high-affinity to the VMAT2, but the binding is essentially irreversible. This results in depletion of biogenic amines, and requires synthesis of new storage vesicles for recovery of biogenic amine storage. The reserpine binding site of VMAT2 appears to be associated with the neurotransmitter uptake site. In experiments described below, the precursor for [³H]reserpine is synthesized and labeled.

Tetrabenazine, also known as TBZ or Xenazine ((SS,RR)-3-isobutyl-9,10-dimethoxy-1,3,4,6,7,11b-hexahydro-pyrido[2,1-a]isoquinolin-2-one), on the other hand, does bind reversibly to the VMAT2, but was developed for the treatment of schizophrenia half a century ago (Kenney C and Jankovic J, *Expert Rev Neurother* 6, 7-17 (2006); incorporated by reference herein). TBZ appears to bind to a different site on the VMAT2 than reserpine. One model of the binding sites on VMAT2 proposes that the reserpine site has high affinity for substrates and is directed toward the cytosol. After binding of substrate to the VMAT2, a conformational change results in the TBZ-binding conformation (Henry et al, 1998 supra). Dihydrotetrabenazine (DTBZ or 2-Hydroxytetrabenazine) was labeled with a radioligand and used to label VMAT2 herein. DTBZ has a hydroxyl group substituted for the ketone of TBZ and has high affinity for VMAT2.

Lobeline (2-((2R,6S)-6-((S)-2-Hydroxy-2-phenylethyl)-1-methylpiperidin-2-yl)-1-phenylethanone) a lipophilic alkaloid of Indian tobacco, interacts with both the VMAT2 and the DAT, and is being investigated as a possible therapeutic for MA abuse (reviewed in Dwoskin and Crooks, *Biochem Pharmacol* 63, 89-98 (2002). It is quite possible that lobeline and related compounds bind to the same site that reserpine binds, but currently there are no available radioligands to label that site. In transfected cells, lobeline has an affinity of 4.3 μM at VMAT2 and 5.4 μM at the DAT (Miller D K et al, *J Pharmacol Exp Ther* 310, 1035-1045 (2004); incorporated by reference herein), while in striatal preparations, lobeline has affinity of 0.88 μM at VMAT2 (Teng L et al, *J Pharmacol Exp Ther* 280, 1432-1444 (1997); incorporated by reference herein). In rats trained to lever press for intravenous MA or sucrose, pretreatment with lobeline decreased responding to both acutely, however the effect on sucrose showed tolerance over several days, while the lobeline suppression of MA-responding was robust over 7 days of testing (Harrod S B et al, *J Pharmacol Exp Ther* 298, 172-179 (2001); incorporated by reference herein).

Ketanserin is primarily considered to be a 5-HT2 receptor antagonist, however it also has high affinity for VMAT2 (reviewed in Zheng G et al, *AAPS J* 8, E682-692 (2006); incorporated by reference herein).

These drugs will be used throughout the assays described below.

V—Compounds

Disclosed herein are compounds useful for selectively inhibiting functional activity of VMAT2. These compounds can be biodiastereoselective and manifest bioenantioselectivity. Compounds disclosed herein have been shown to be potent antagonists of [³H]5HT uptake by the hVMAT2 and their potency is correlated with their reversible inhibition of [³H]reserpine binding to the hVMAT2. While [³H]DTBZ and [³H]ketanserin are available, DTBZ and ketanserin bind at a site that is not associated with hVMAT2 function.

Disclosed herein are compounds of Formula I

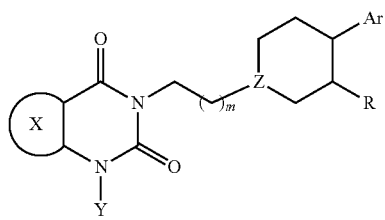

wherein X is a substituted or unsubstituted 5- or 6-membered aryl or substituted or unsubstituted 5- or 6-membered heteroaryl,
Z is N or CH,
m is 1, 2, or 3,
Ar is a substituted or unsubstituted 5- or 6-membered aryl or a substituted or unsubstituted 5- or 6-membered heteroaryl,
R is H, ethyl ester, isopropyl ester, —C(O)-alkyl (i.e., methyl ketone, ethyl ketone, etc.), or substituted or unsubstituted 5-membered heteroaryl,
Y is H, substituted or unsubstituted alkyl, substituted or unsubstituted aryl, or substituted or unsubstituted heteroaryl;
wherein the bond between the carbon atoms bearing Ar and R is a single or double bond,
or a pharmaceutically acceptable salt, solvate, hydrate, stereoisomer, mixture of stereoisomers, crystal form, isomer, or isotopomer thereof.

In some embodiments, the bond between the carbon atoms bearing Ar and R is a single bond, and the groups labeled Ar and R are in an RR configuration, an SS configuration, an SR configuration, or an RS configuration.

Additionally disclosed are compounds of Formula II:

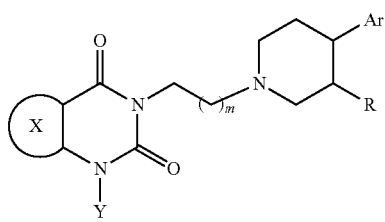

wherein Y is H, and X, m, Ar, R, and Y are defined as for Formula I. In still further examples of the compounds of Formula II, R is ethyl ester.

Additionally disclosed are compounds of Formula III:

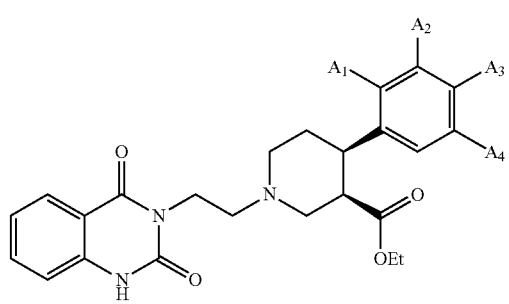

wherein $A_1$, $A_2$, $A_3$, and $A_4$, are independently H, alkyl, substituted alkyl, aryl, substituted aryl, halo, alkoxy, haloalkyl, haloalkoxy, ester, keto, hydroxyl, amino, substituted amino, amido, or nitro. In still further examples, $A_1$, $A_2$, $A_3$, and $A_4$ are independently H, methyl, ethyl, isopropyl, [1,4]dioxin-5-yl, fluoro, chloro, trifluoromethyl, amino, dimethylamino, methylamido, nitro, azo, benzyl, 2-phenyl ethyl, pyrrolyl, ethyl ester, keto, 1-hydroxyethyl, hydroxyl, methoxy, trifluoromethoxy, or tert-butoxycarbonylamino.

Additionally disclosed are compounds of Formula IV

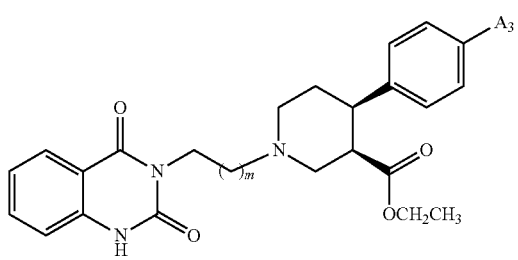

wherein $A_3$ is halo and m is 2 or 3.

Additionally disclosed are compounds of Formula V

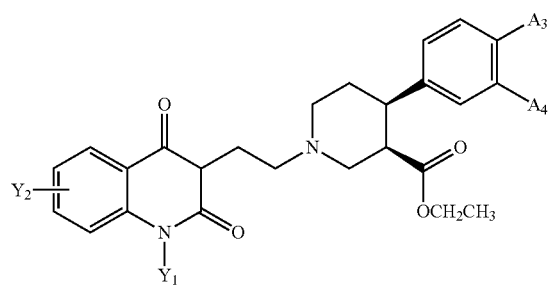

wherein $Y_1$ is H, methyl, ethyl, or 2-benzylethyl, wherein $Y_2$ is H or halo, and wherein $A_3$ and $A_4$ are independently H or halo.

Additionally disclosed are compounds of Formula VI

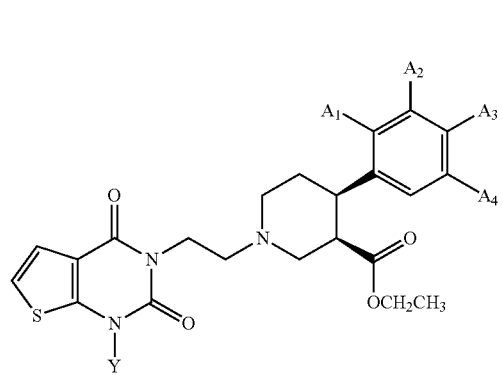

wherein $A_1$, $A_2$, $A_3$, and $A_4$ are independently H, halo, or haloalkyl and wherein Y is H or alkyl.

Certain compounds described herein may be synthesized according to Scheme 1, below. Additional compounds described herein may be synthesized using similar methods.

Scheme 1

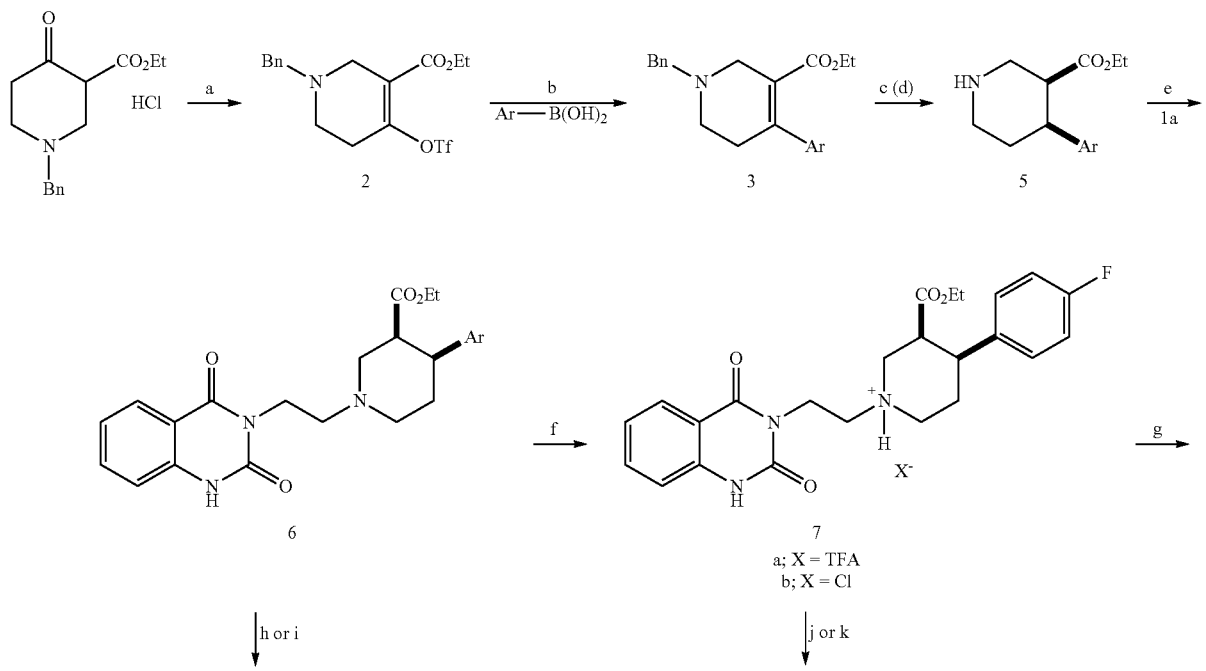

-continued

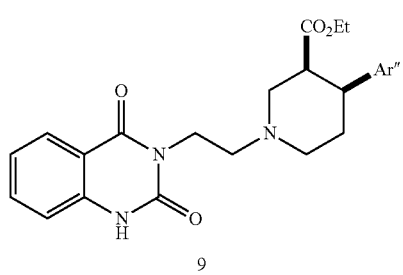

9

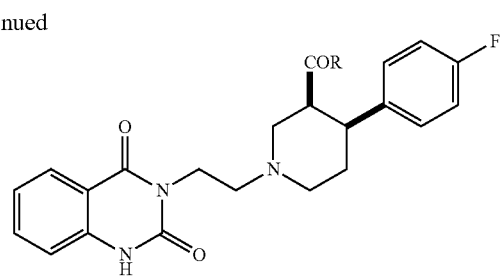

10 a; R = OMe
b; R = Oi-Pr
c; R = NHEt

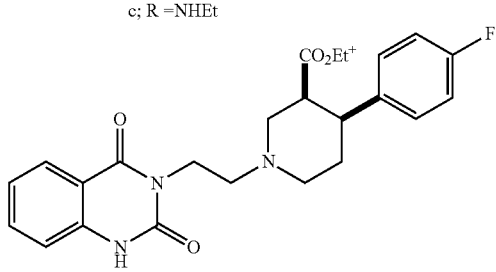

8

Reaction Conditions a through k of Scheme 1 are as follows:

(a) 1. $K_2CO_3$, DCM; 2. NaH, PhN(Tf)$_2$, DMF, 0° C., 1.5 h; (b) Pd(PPh$_3$)$_4$, LiCl, Na$_2$CO$_3$, toluene/EtOH, 85° C., 4-16 h; (c) Pd/C, H$_2$, EtOH, rt, 24-48 h; (d) i) ACE-Cl, 100° C., 2 h; ii) EtOH, reflux, 30 min; (e) 1, toluene or DMF/1,4-dioxane or CH$_3$CN, 90-110° C., 24-48 h; (f) 3 M HCl, uW, 105° C., 3 h; (g) EDCl, DMAP, EtOH*, DMF, rt, 3 h; (h) silicagel, 50° C., high-vacuum (2 mmHg), 3 d; (i) TFA, DCM, rt, 2 h; (j) EtNH$_2$, EDCl, HOBt, NMM, DMF, rt, overnight; (k) alcohol, EDCl, DMAP, NMM, DMF, rt, overnight.

Compounds 1a, 1b and 1c are shown below, and can be interchangeably used in conditions e above.

The Ar substituents are shown here:

Ar =

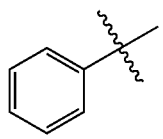
a

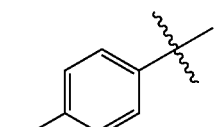
b

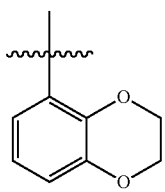
c

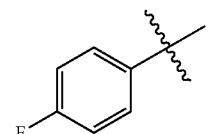
d

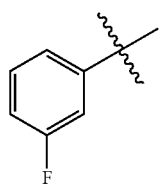
e

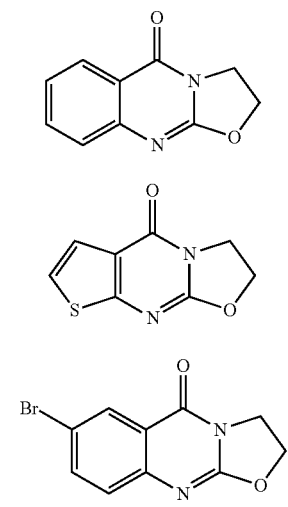

1a

1b

1c

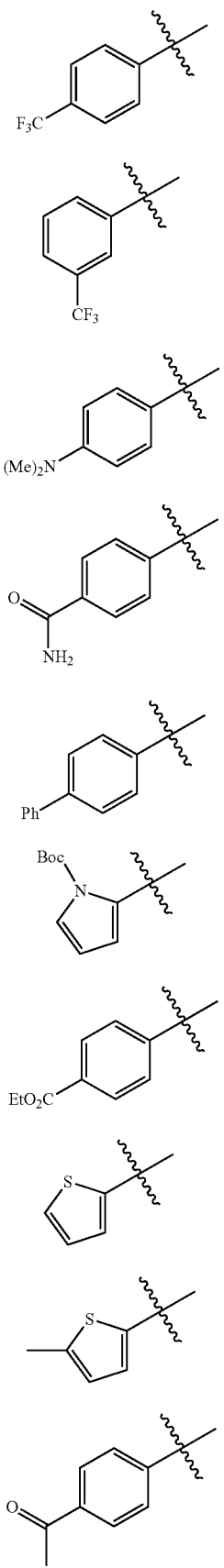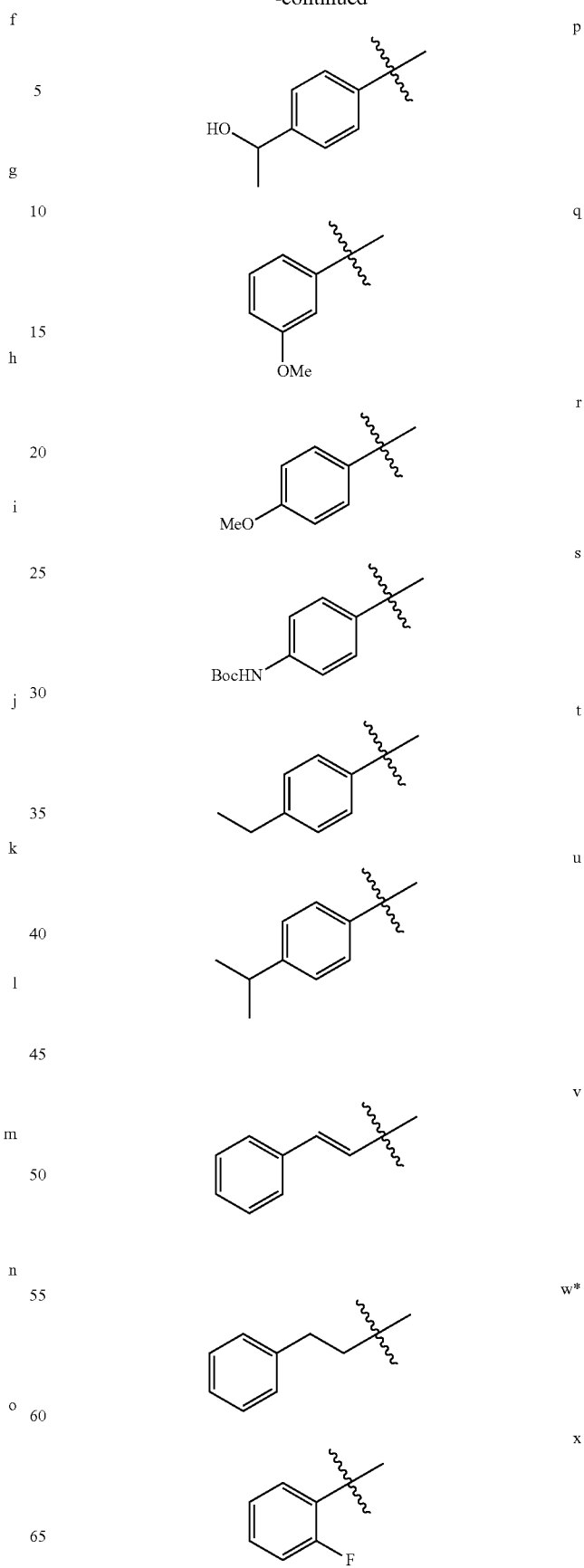

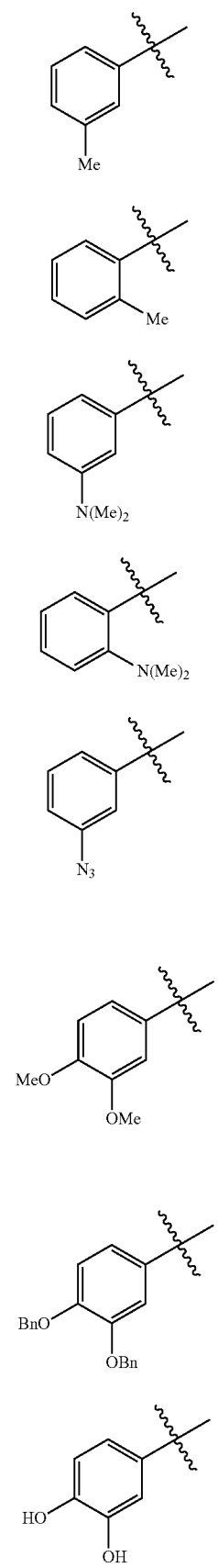
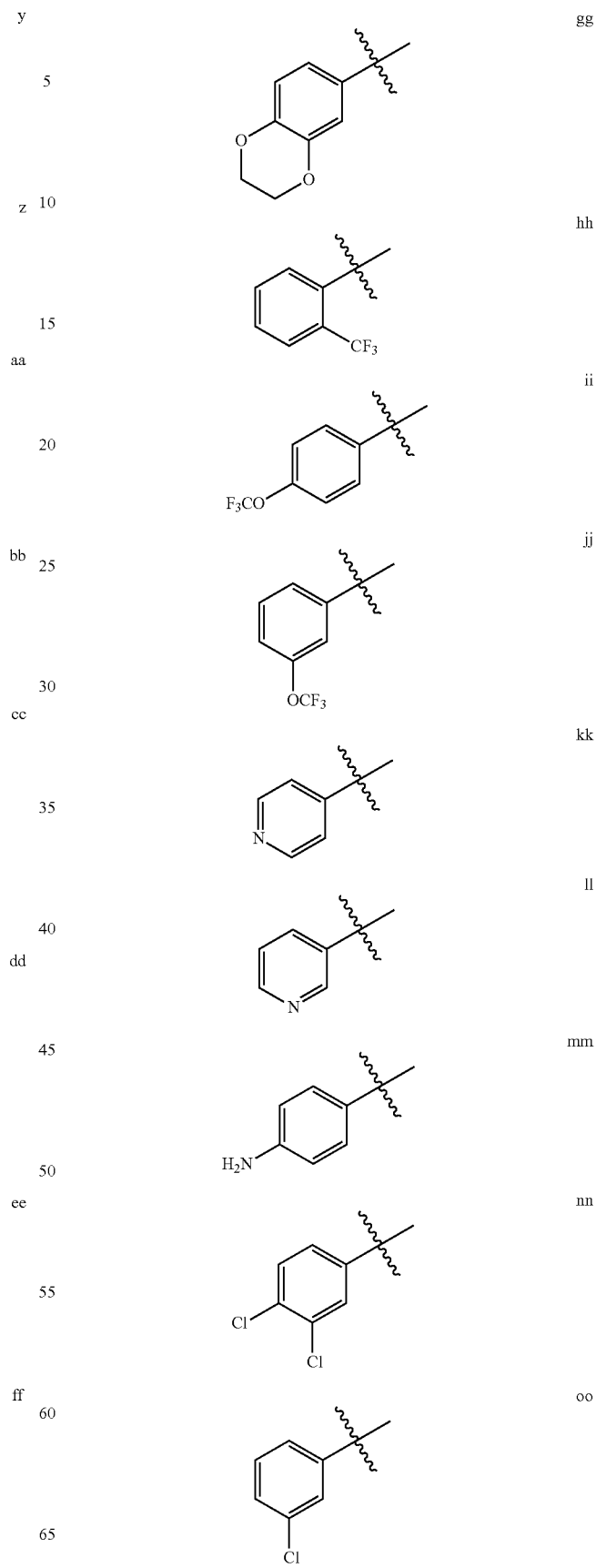

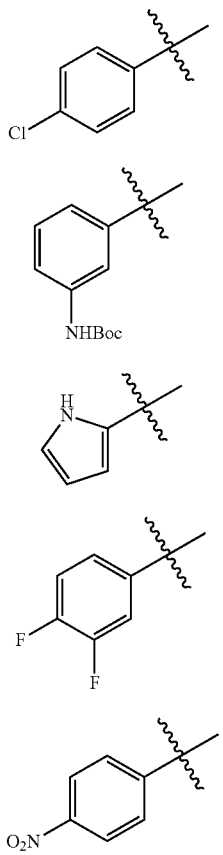

pp qq rr ss tt

The compounds described herein can be formulated in any excipient a biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresols, formalin and benzyl alcohol. In certain aspects, the pH can be modified depending upon the mode of administration. For example, a formulation having a pH of from about 5 to about 6 may be suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the compounds described herein. Any of the compounds described herein can contain combinations of two or more pharmaceutically-acceptable compounds. Examples of such compounds include, but are not limited to, hypertension agents, anti-emetics, anti-psychotic agents, chlorpromazine, and the like.

The pharmaceutical compositions can be prepared using techniques known in the art. In one aspect, the composition is prepared by admixing a compound described herein with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having nucleophilic groups, can be undertaken on the compound. Second, non-covalent entrapment of a pharmacologically active agent in a cross-linked polysaccharide is also possible. Third, electrostatic or hydrophobic interactions can facilitate retention of a pharmaceutically-acceptable compound in the compounds described herein.

It will be appreciated that the actual preferred amounts of active compound in a specified case will vary according to the specific compound being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, can determine dose according to standard recommendations (Physicians Desk Reference, Barnhart Publishing (1999)).

The pharmaceutical compositions described herein can be administered in a number of ways depending on whether local or systemic treatment is desired, and on the area to be treated. Compositions as described herein can be administered by different routes, including, without limitation, intravenous, intraperitoneal, subcutaneous, intramuscular, and oral administration. For oral administration, the compositions can be formulated into oral dosage forms such as, for example, tablets or liquid-filled capsules, or liquid preparations such as syrups, elixirs, or concentrated drops. For injection, compositions can be formulated in isotonic liquid solutions, such as in physiologically compatible buffers or carbohydrate solutions. Administration can be topically (including ophthalmically, rectally, intranasally). Formulations for topical administration can include ointments, lotions, creams, gels, drops, suppositories, sprays, liquids and powders. Conventional pharmaceutical carriers, aqueous, powder or oily bases, thickeners and the like can be necessary or desirable. Administration can also be directly into the lung by inhalation of an aerosol or dry micronized powder.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

EXAMPLES

The following examples are illustrative of disclosed methods. In light of this disclosure, those of skill in the art will recognize that variations of these examples and other examples of the disclosed method would be possible without undue experimentation.

Example 1

Biogenic Amine Transporters [$^{125}$I] RTI-55 Binding

Standard methods of assessing [$^3$H]neurotransmitter uptake and [$^{125}$I]RTI-55 binding using HEK cell lines are described in Eshleman et al, *J Pharmacol Exp Therap* 289, 877-885 (1999), which is incorporated by reference herein and were as follows:

Compounds were weighed and dissolved in DMSO to make a stock solution of 10 mM. An initial dilution to 50 µM in assay buffer or water for binding, or to 1 mM in assay buffer or water for uptake, was made. Subsequent dilutions were made with assay buffer supplemented with DMSO, maintaining a final concentration of 0.1% DMSO. Pipetting was conducted using a Biomek 2000 robotic workstation.

Cell preparation: Human embryonic kidney cells expressing the recombinant human dopamine transporter (HEK-hDAT), serotonin transporter (HEK-hSERT) or norepinephrine transporter (HEK-hNET) were used. Cells were grown to 100% confluence on 150 mm diameter tissue culture dishes and served as the tissue source. Cell membranes were prepared as follows. Medium was poured off the plate, and the plate was washed with 10 ml of calcium- and magnesium-free phosphate-buffered saline. Lysis buffer (10 ml; 2 mM HEPES with 1 mM EDTA) was added. After 10 min, lysed cells were scraped from plates, transferred into centrifuge tubes, and centrifuged at 30,000×g for 20 min. The supernatant fluid was removed, and the pellet was resuspended in 12-32 ml of sucrose (0.32 M) using a Polytron at setting 7 for 10 sec. The resuspension volume depended on the density of binding sites within a cell line and was chosen to reflect binding of 10% or less of the total radioactivity.

Assay conditions: Each assay tube contained 50 µl of membrane preparation (about 10-25 µg of protein), 25 µl of unknown or buffer (Krebs-HEPES, pH 7.4; 122 mM NaCl, 2.5 mM $CaCl_2$, 1.2 mM $MgSO_4$, 10 µM pargyline, 100 µM tropolone, 0.2% glucose and 0.02% ascorbic acid, buffered with 25 mM HEPES), 25 µl of [$^{125}$I]RTI-55 (40-80 µM final concentration) and additional buffer sufficient to bring the final volume to 250 µl. Membranes were preincubated with unknowns for 10 min prior to the addition of the [$^{125}$I]RTI-55. The assay tubes were incubated at 25° C. for 90 min in the dark. Binding was terminated by filtration over Whatman GF/C filters using a Tomtec Mach II or MACH III 96-well cell harvester. Filters were washed for six seconds with ice-cold saline. Scintillation fluid was added to each square and radioactivity remaining on the filters was determined using a Wallac µ- or beta-plate reader. Specific binding was defined as the difference in binding observed in the presence and absence of mazindol (5 µM, HEK-hDAT and HEK-hNET) or imipramine (5 µM, HEK-hSERT). Three or more independent competition experiments were conducted with duplicate determinations, unless the $IC_{50}$ value for a drug was greater than 10 µM, and then only two experiments were conducted. GraphPAD Prism was used to analyze the data, with $IC_{50}$ values converted to Ki values using the Cheng-Prusoff equation and $K_d$ values for [$^{125}$I]RTI-55 of 1.2, 0.98, and 12.1 nM for hDAT, hSERT and hNET, respectively.

Example 2

Biogenic Amine Transporter [$^3$H]Neurotransmitter Uptake

Compounds were tested for potency at inhibition of [$^3$H]DA (dopamine), [$^3$H]NE (norepinephrine) or [$^3$H]5-HT (serotonin) uptake if the Ki value for inhibition of [$^{125}$I] RTI-55 binding to hDAT, hNET or hSERT, respectively, was less than 10 µM.

Cell preparation: Human embryonic kidney cells expressing the recombinant human dopamine transporter (HEK-hDAT), serotonin transporter (HEK-hSERT) or norepinephrine transporter (HEK-hNET) were used. Cells were grown to confluence as described above. The medium was removed, and cells were washed with phosphate buffered saline (PBS) at room temperature. Following the addition of 3 ml Krebs Hepes buffer, the plates were warmed in a 25° C. water bath for 5 min. The cells were gently scraped and then triturated with a pipette. Cells from multiple plates were combined. One plate provided enough cells for 48 wells, which was required to generate data on two complete curves for the unknowns.

Uptake inhibition assay conditions: The assay was conducted in 96 1-ml vials. Krebs-HEPES (350 µl) and unknowns (50 µl) were added to vials and placed in a 25° C. water bath. Specific uptake was defined as the difference in uptake observed in the presence and absence of mazindol (5 µM, HEK-hDAT and HEK-hNET) or imipramine (5 µM, HEK-hSERT). Cells (50 µl) were added and preincubated with the unknowns for 10 min. The assay was initiated by the addition of [$^3$H]DA, [$^3$H]5-HT, or [$^3$H]NE (50 µl, 20 nM final concentration). Filtration through Whatman GF/C filters presoaked in 0.05% polyethylenimine was used to terminate uptake after 10 min. The $IC_{50}$ values were calculated applying the GraphPAD Prism program to each curve made up of 6 drug concentrations each. Three or more independent competition experiments were conducted with triplicate determinations, unless the $IC_{50}$ value is greater than 10 µM, and then only two experiments were conducted.

Example 3

VMAT2: [$^3$H]dihydrotetrabenazine (DHTB) and [$^3$H]Ketanserin Binding Assays

Membrane preparation for binding, uptake and release assays using HEK-hVMAT2 cells: Human embryonic kidney cells expressing the human vesicular monoamine transporter 2 (HEK-hVMAT2) were used. HEK-hVMAT2 cells were grown until confluent. The media was removed from plates, solution A [sucrose (0.32 M) with protease inhibitors] was added to the plate, and cells were scraped from plate. Cells were homogenized with 12 strokes of a glass/glass homogenizer. The homogenate was centrifuged at 800×g for 10 min. The supernatant was removed and saved, and the pellet was resuspended, homogenized and centrifuged as above. The supernatants were combined and centrifuged at 10,000×g for 20 min. The pellet was resuspended in solution A (0.75 ml). The membranes were osmotically shocked by addition of 2.625 ml ice cold water and homogenized by 5 strokes of a glass/Teflon homogenizer. The osmolarity was reestablished with addition of Tris (338 µl, 0.25M, pH 7.4 at 4° C.), sodium potassium tartrate (338 µl, 1.0 M), and MgSO$_4$ (4 µl, 0.9M). The homogenate was centrifuged at 20,000×g for 20 min.

[$^3$H]DHTB binding assay: The pellet was resuspended in sucrose (0.32M, 2.5-5 ml/plate of cells). The membrane preparation from one plate was sufficient to conduct 2-4 drug curves, and depended on the confluency of the plate. The binding assay included membrane preparation (50 µl), drug, [$^3$H]DHTB (7-10 nM), and VMAT buffer (2 mM MgSO$_4$, 25 mM Tris, 100 mM NaK tartrate, 0.5 mM EDTA, 4 mM KCl, 1.7 mM ascorbic acid, 100 µM tropolone and 10 µM pargyline, pH 7.4 at 25° C.) in a final volume of 0.25 ml. Drugs were preincubated with membranes for 10 minutes prior to the addition of [$^3$H]DHTB, and the assay was incubated in the dark for 60 min at room temp. Binding was terminated by filtration over Whatman GF/C filters using a Tomtec 96-well cell harvester. Filters were washed for six seconds with ice-cold saline. Scintillation fluid was added to each square and radioactivity remaining on the filters was determined using a Wallac µ- or beta-plate reader. Specific binding was defined as the difference in binding observed in the presence and absence of Ro4-1284 (10 µM, generously supplied by Hoffman LaRoche). Three or more independent competition experiments were conducted with duplicate determinations. GraphPAD Prism was used to analyze the data, with IC$_{50}$ values converted to K$_i$ values using the Cheng-Prusoff equation and a K$_d$ value of 38.4 nM for [$^3$H]DHTB.

Example 4

VMAT2: [$^3$H]APQ Binding Assay

Human embryonic kidney cells expressing the human vesicular monoamine transporter 2 (HEK-hVMAT2) were used. HEK-hVMAT2 cells were grown until confluent. The media was removed from plates, ice cold 25 mM Tris-HCl [with protease inhibitors] was added to the plate, and cells were scraped from the plate. Cells were homogenized with a Polytron homogenizer on setting 6 for 6 seconds. The homogenate was centrifuged at 30,900×g for 20 min. The pellet was osmotically shocked by addition of 2.625 ml ice cold water and homogenized by 5 strokes of a glass/Teflon homogenizer. The osmolarity was reestablished with addition of Tris (338 µl, 0.25M, pH 7.4 at 4° C.), sucrose (0.32M), sodium potassium tartrate (338 µl, 1.0 M), and MgSO$_4$ (4 µl, 0.9M). The homogenate is centrifuged at 30,900×g for 20 min.

[$^3$H]APQ binding assay: The membrane preparation from one plate was sufficient to conduct 2-4 drug curves, and depended on the confluency of the plate. The binding assay included membrane preparation (50 µl), drug, [$^3$H]APQ (40-50 nM), and VMAT buffer (2 mM MgSO$_4$, 25 mM Tris, 100 mM NaK tartrate, sucrose (0.32 M), 0.5 mM EDTA, 4 mM KCl, 1.7 mM ascorbic acid, 100 µM tropolone and 10 µM pargyline, pH 7.4 at 4° C.) in a final volume of 0.25 ml. Drugs were pre-incubated with membranes for 10 minutes prior to the addition of [$^3$H]APQ, and the assay was incubated in the dark for 60 min at 4° C. Binding was terminated by filtration over Whatman GF/C filters using a Tomtec 96-well cell harvester. Filters were washed for six seconds with ice-cold Tris-HCl (25 mM). Scintillation fluid was added to each square and radioactivity remaining on the filters was determined using a Wallac µ- or beta-plate reader. Specific binding was defined as the difference in binding observed in the presence and absence of 10 µM O-7443 (an analog of APQ). Three or more independent competition experiments were conducted with duplicate determinations. GraphPAD Prism was used to analyze the data, with IC$_{50}$ values converted to Ki values using the Cheng-Prusoff equation and a K$_d$ value of 93.5 nM for [$^3$H]APQ.

Example 5

Reserpine Binding Assay

Membrane preparation for binding assays using HEK-hVMAT2 cells: Human embryonic kidney cells expressing the human vesicular monoamine transporter 2 (HEK-hVMAT2) were used. HEK-hVMAT2 cells were grown until confluent. The media was removed from plates, ice cold 25 mM Tris-HCl [with protease inhibitors] was added to the plate, and cells were scraped from the plate. Cells were homogenized with a Polytron homogenizer on setting 6 for 6 seconds. The homogenate was centrifuged at 30,900×g for 20 min. The pellet was osmotically shocked by addition of 2.625 ml ice cold water and homogenized by 5 strokes of a glass/Teflon homogenizer. The osmolarity was reestablished with addition of Tris (338 µl, 0.25 M, pH 7.4 at 4° C.), sucrose (0.32 M), sodium potassium tartrate (338 µl, 1.0 M), and MgSO$_4$ (4 µl, 0.9M). The homogenate was centrifuged at 30,900×g for 20 min.

[$^3$H]Reserpine binding assay: The membrane preparation from two plates was sufficient to conduct 1 drug curve, and depended on the confluency of the plate. The binding assay included membrane preparation (100 µl), drug, [$^3$H]Reserpine (7-10 nM), and VMAT buffer (2 mM MgSO$_4$, 25 mM Tris, 100 mM NaK tartrate, sucrose (0.32M), 0.5 mM EDTA, 4 mM KCl, 1.7 mM ascorbic acid, 100 µM tropolone and 10 µM pargyline, pH 7.4 at 30° C.) in a final volume of 1 ml. Drugs were pre-incubated with membranes in 13×100 borosilicate tubes for 10 minutes prior to the addition of [$^3$H]Reserpine, and the assay was incubated in the dark for 60 min at 30° C. Binding was terminated by addition of 1 µM reserpine at 4° C. for 10 minutes. Individual samples were filtered over Whatman GF/C filters using a Millipore 12-channel membrane harvester and washed with 12 ml ice-cold Tris-HCl (25 mM). Scintillation fluid was added to each scintillation tube and radioactivity remaining on the filters was determined using a Beckman LS-6500 multi-purpose scintillation counter. Specific binding was defined as the difference in binding observed in the presence and absence of 1 µM Reserpine. Three or more independent competition experiments were conducted with duplicate determinations. GraphPAD Prism was used to analyze the data, with IC$_{50}$ values converted to Ki values using the Cheng-Prusoff equation and a K$_d$ value of 8.6 nM for [$^3$H]Reserpine.

Example 6 h5HT1A Receptors: [$^3$H]8-OH-DPAT Binding

Human embryonic kidney cells expressing the human 5HT1A receptor (HEK-h5HT1A) were used. The cells were grown to confluence in DMEM containing 10% Fetal-Clone® (abbreviated as FC—source: HyClone), 0.05% penicillin-streptomycin (pen-strep), and 300 µg/mL of Geneticin (G418). The cells were scraped from 150 mm plates into phosphate-buffered saline and centrifuged at 270×g, 1200 rpm, for 10 minutes. The cell pellet was homogenized in 50 mM Tris-HCl (pH 7.7) with a Polytron, and centrifuged at 27,000×g. The homogenization and centrifugation were repeated to wash any remaining 5HT from the growth media. The final pellet was resuspended at 0.5 mg protein/mL in assay buffer (25 mM Tris-HCl, pH 7.4, containing 100 μM ascorbic acid and 10 μM pargyline). The assay was performed in duplicate in a 96-well plate. Serial dilutions of test compounds were made using the Biomek 2000 robotics system. The reaction mixture contained unknown compound, 100 μl of cell homogenate (0.05 mg protein/well) and 100 μl of [$^3$H]8-OH-DPAT (0.5 nM final concentration, 170 Ci/mmol, Perkin Elmer) in a final volume of 1 ml. Nonspecific binding was determined with 1.0 μM dihydroergotamine. The plates were incubated at room temperature for 60 minutes and then filtered through polyethylenimine-soaked (0.05%) "A" filtermats on a Tomtec cell harvester. The filters were washed with cold 50 mM Tris buffer (pH 7.7) for 6 sec, dried, spotted with scintillation cocktail, and counted for 2 minutes after a 4 hour delay on a Wallac Betaplate 1205 liquid scintillation counter. $IC_{50}$ values were calculated with GraphPad Prism, and $IC_{50}$ values were converted to Ki values using the Cheng-Prusoff correction and a $K_d$ value of 5.02 nM for [$^3$H]8-OH-DPAT.

Example 7 h5HT2A and 2C Receptors: [$^{125}$I]DOI Binding Assays

The method was adapted from AR Knight et al, *Naunyn-Schmeideberg's Arch Pharmacol* 370, 114-123 (2004).

Method: Human embryonic kidney cells expressing the human 5HT2A receptor (HEK-h5HT2A) or human 5HT2C receptor (HEK-h5HT2C) were used. The cells were grown until confluent on 15 cm plates. Media was removed, cells were washed with phosphate-buffered saline (PBS), scraped into 2 ml PBS and frozen at −20° C. until needed. Cell suspension was thawed, 10 ml assay buffer (50 mM Tris, pH 7.4 at 37° C., with 0.1% ascorbic acid and 5 mM $CaCl_2$) was added per plate of cells, and polytronned at setting 6 for 5 sec. The homogenate was centrifuged at 15,500 rpm for 20 min. To minimize the residual 5HT concentration, the pellet was resuspended in buffer, polytronned, and centrifuged as above. The final pellet was resuspended in 2 ml buffer/plate of cells.

The binding assay included 50 μl drug, 5HT or buffer, 50 μl cell homogenate, 50 μl [$^{125}$I]DOI (∼0.1 nM) and buffer in a final volume of 250 μl. Specific binding was defined as the difference between total binding and binding in the presence of 10 μM 5HT. The reaction was incubated for 1 hour at 37° C., and terminated by filtration through Wallac A filtermats presoaked in 0.05% polyethylenimine using a Tomtec 96-well harvester. Radioactivity remaining on filters was counted in a Wallac betaplate reader. $IC_{50}$ values were calculated using GraphPad Prism. $IC_{50}$ values were converted using the Cheng-Prusoff equation. The density of 5HT2A receptors was 612±19 fmol/mg protein. The density of 5HT2C receptors was 900±170 fmol/mg protein. The $K_d$ values used in the equations were 3.624 nM and 4.18 nM for [$^{125}$I] DOI at 5HT2A and 5HT2C receptors, respectively.

Example 8

Ketanserin Analogs

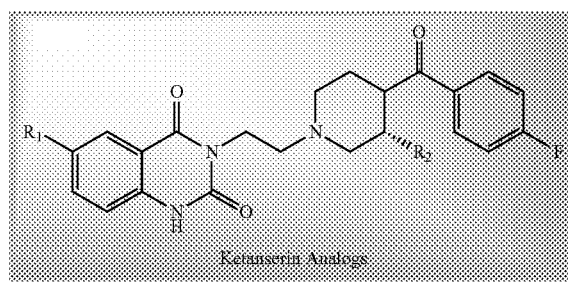

Figure 1

These compounds showed poor blocking of radioligand binding to recombinant hVMAT2 or/and manifested substantial potency at blocking radioligand binding to the 5-HT2a receptor.

TABLE 1

Binding of Ketanserin Analogs

| $R_1$ | $R_2$ | hVMAT2 [$^3$H]DTBZ Ki (nM) ± SEM | hVMAT2 5HT Uptake $IC_{50}$ (nM) ± SEM | 5-HT1A [$^3$H] 8—OH DPAT Ki(nM) ± SEM | 5-HT2A [$^{125}$I]DOI Ki (nM) ± SEM |
|---|---|---|---|---|---|
| H | H | 119 ± 3 | 142 ± 23 | >3 μM | 24.7 ± 7.6 |
| Br | H | >3 μM | >2 μM | >2 μM | 0.80 ± 0.24 |
| H | α-$CO_2$Et | 1166 ± 314 | 60 ± 10 | >10 μM | 37.3 ± 8.5 |
| H | α/β-$CH_3$ | 276 ± 24 | 333 ± 106 | >10 μM | 45.9 ± 12.4 |
| H | α-$CH_3$ | >6.4 μM | >7.3 μM | >5 μM | 19.8 ± 5.8 |

New compounds comprising a direct link between the piperidine and 4-aryl group were then generated to alter the molecular topology of the molecule. A robust synthesis was developed and 5 new compounds were prepared as shown in Table 3.

Example 9

APQ Analogs

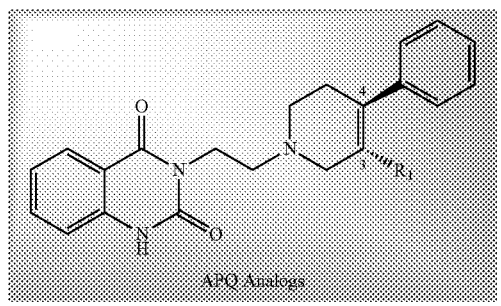

Preliminary data on these compounds indicated that a novel VMAT2 selective inhibitor could be obtained. All the compounds inhibited uptake of [$^3$H]5HT with the compound having a double bond at 3, 4 and a hydrogen at $R_1$ being especially potent. The compound having a cis ethyl ester at $R_1$ and a single bond at 3, 4 was also quite potent at inhibiting uptake, but showed no binding to the 5-HT2A receptor. This can be compared to the compound with a trans ethyl ester that inhibited 5HT uptake, but bound to the 5-HT2A receptor. Data are summarized in Table 2.

TABLE 2

Summary of Initial APQ Analog Data

| $R_1$ | 3,4-bond | hVMAT2 [$^3$H]DTBZ Ki (nM) ± SEM | hVMAT2 5HT Uptake IC$_{50}$ (nM) ± SEM | 5-HT1A [$^3$H] 8—OH DPAT Ki(nM) ± SEM | 5-HT2A [$^{125}$I]DOI Ki (nM) ± SEM |
|---|---|---|---|---|---|
| H | ene | 821 ± 197 | 3.9 ± 0.5 | 197 ± 15 | 139 ± 27 |
| H | single | 752 ± 372 | 10 ± 2.6 | >4.2 μM | 126 ± 39 |
| CO$_2$-Et | ene | 874 ± 276 | 66 ± 15 | >6.3 | 81 ± 26 |
| β-CO$_2$-Et | single | >9 μM | 17 ± 4.4 | >10.0 μM | >10.0 μM |
| α-CO$_2$-Et | single | >1.2 μM | 74 ± 16 | >10 μM | 37.3 ± 8.5 |

Example 10

Binding of Compounds of Formula III

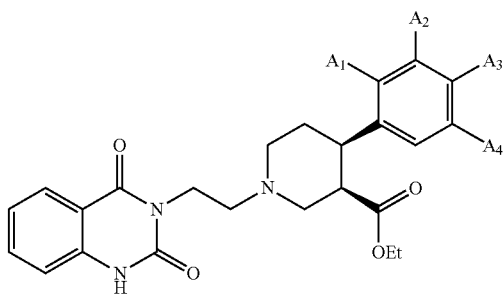

Formula III

TABLE 3

| $A_1$ | $A_2$ | $A_3$ | $A_4$ | hVMAT2 [$^3$H]DTBZ Ki (nM) ± SEM | hVMAT2 5HT Uptake IC$_{50}$ (nM) ± SEM | 5-HT1A [3H] 8-OH DPAT Ki(nM) ± SEM | 5-HT2A [125I]DOI Ki (nM) ± SEM |
|---|---|---|---|---|---|---|---|
| H | H | H | H | 1166 ± 314 | 17 ± 4.4 | >10 μM | 37.3 ± 8.5 |
| H | H | F | H | >7 μM | 32 ± 8 | >9 μM | >2 μM |
| H | H | H | F | >10 μM | 63 ± 10 | — | — |
| F | H | H | H | >10 μM | 28 ± 12 | — | — |
| H | H | F | F | >10 μM | 100 ± 19 | — | — |
| H | H | Cl | H | >10 μM | 49 ± 1 | — | — |
| H | H | H | Cl | >9 μM | 34 ± 8 | — | — |
| H | H | Cl | Cl | — | — | — | — |
| H | H | H | OCH$_3$ | >10 μM | 180 ± 54 | — | — |
| H | H | OCH$_3$ | OCH$_3$ | >10 μM | >3 μM | — | — |
| H | H | NO$_2$ | H | >10 μM | 758 ± 165 | — | — |
| H | H | NH$_2$ | H | >10 μM | 2155 ± 237 | — | — |
| N(CH$_3$)$_2$ | H | H | H | >6 μM | >2 μM | — | — |
| H | H | H | N(CH$_3$)$_2$ | >10 μM | >5 μM | >10 μM | >10 μM |
| H | H | H | N$_3$ | >7 μM | 74 ± 11 | — | — |
| CF$_3$ | H | H | H | — | 328 ± 38 | — | — |
| H | H | CF$_3$ | H | >10 μM | 416 ± 43 | >10 μM | >10 μM |
| H | H | H | CF$_3$ | >10 μM | 166 ± 6 | >10 μM | >10 μM |
| CH$_3$ | H | H | H | >5 μM | 31 ± 3 | — | — |
| H | H | CH$_3$ | H | >9 μM | 313 ± 54 | >10 μM | >10 μM |
| H | H | H | CH$_3$ | >6200 | 53 ± 10 | — | — |
| H | H | Benzyl | H | >10 μM | >10 μM | >10 μM | >10 μM |
| H | H | Isopropyl | H | 1625 ± 107 | 684 ± 249 | — | — |
| H | H | OCH$_3$ | H | >10 μM | 36 ± 11 | — | — |
| H | H | CH$_2$CH$_3$ | H | >8400 | 906 ± 14 | — | — |
| H | H | COOEt | H | >10 μM | >10 μM | >10 μM | >10 μM |
| H | H | OCF$_3$ | H | >5 μM | — | — | — |
| H | H | OH | OH | — | 333 ± 85 | — | — |
| H | H | CHOHCH$_3$ | H | >9 μM | >8 μM | >10 μM | >10 μM |
| H | H | CONH$_2$ | H | >3 μM | >10 μM | — | — |

Example 11

Binding of Optical Activity Variants of Formula III

The compound of Formula III above with $A_1$=H, $A_2$=H, $A_3$=F, and $A_4$=H is designated Compound 5d. 5d was separated into purified + and − variants. Results are shown in Table 4.

TABLE 4

| Compound | hVMAT2 [³H]DTBZ Ki (nM) ± SEM | hVMAT2 5HT Uptake IC₅₀ (nM) ± SEM | 5-HT1A [³H] 8—OH DPAT Ki(nM) ± SEM | 5-HT2A [125I]DOI Ki (nM) ± SEM |
|---|---|---|---|---|
| 5d (+/−) | >7 µM | 32 ± 8 | >9 µM | >2 µM |
| 5d+ | >10 µM | 16 ± 3.3 | >10 µM | >10 µM |
| 5d− | >10 µM | 52.9 ± 10.5 | >10 µM | >10 µM |

Example 12

Binding of Compounds of Formula IV

The following is an example of a compound of Formula IV wherein $A_3$ is F. Binding of variants in the alkyl linker is described in Table 5.

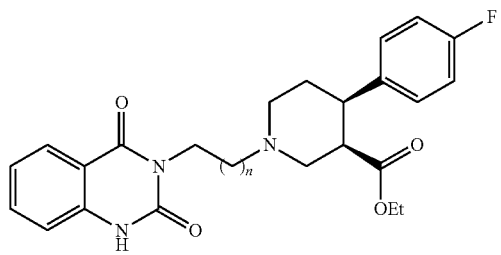

TABLE 5

| n | hVMAT2 [³H]DTBZ Ki (nM) ± SEM | hVMAT2 5HT Uptake IC₅₀ (nM) ± SEM | 5-HT1A [³H] 8—OH DPAT Ki(nM) ± SEM | 5-HT2A [125I]DOI Ki (nM) ± SEM |
|---|---|---|---|---|
| 1 | >7 µM | 32 ± 8 | >9 µM | >2 µM |
| 2 | >10 µM | 43 ± 4 | >10 µM | — |
| 3 | >10 µM | 133 ± 52 | — | — |

Example 13

Binding of Compounds of Formula V

Compounds of Formula V were synthesized. Binding of variants in $A_1$ are shown in Table 6 below.

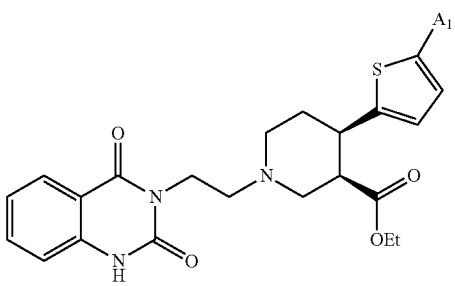

TABLE 6

| $A_1$ | hVMAT2 [³H]DTBZ Ki (nM) ± SEM | hVMAT2 5HT Uptake IC₅₀ (nM) ± SEM | 5-HT1A [³H] 8—OH DPAT Ki(nM) ± SEM | 5-HT2A [125I]DOI Ki (nM) ± SEM |
|---|---|---|---|---|
| H | >10 µM | 60 ± 26 | >9 µM | >9 µM |
| CH₃ | >8 µM | 312 ± 18 | — | — |

Example 14

Binding of Compounds of Formula VI

Binding of compounds with the structure of Formula VI wherein $A_1$ and $A_2$ are both H is shown in Table 7 below.

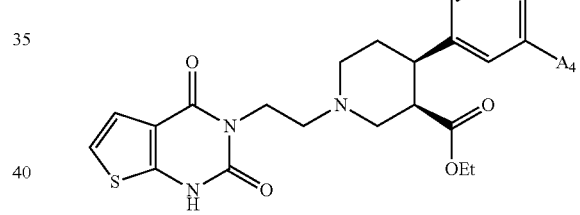

TABLE 7

| $A_3$ | $A_4$ | hVMAT2 [³H]DTBZ Ki (nM) ± SEM | hVMAT2 5HT Uptake IC₅₀ (nM) ± SEM | 5-HT1A [³H] 8—OH DPAT Ki(nM) ± SEM | 5-HT2A [125I]DOI Ki (nM) ± SEM |
|---|---|---|---|---|---|
| H | CF₃ | >10 µM | 342 ± 103 | — | — |
| CF₃ | H | >10 µM | 1471 ± 65 | — | — |
| H | F | >10 µM | 200 ± 51 | — | — |
| F | H | >10 µM | 133 ± 20 | — | — |

Example 15

Synthesis of 2H-Oxazolo[2,3-b]quinazolin-5(3H)-one (Compound 1a)

A dry 250 mL round bottom flask was charged with 3-(2-chloroethyl)-2,4-quinazolinedione (2.00 g, 8.90 mmol), KI (148 mg, 0.89 mmol), K₂CO₃ (2.46 g, 17.8 mmol), and dry acetonitrile (32 mL), then heated to 80° C. for 5 h. The mixture was concentrated, then partitioned between CH₂Cl₂ (75 mL) and H₂O (20 mL), and the layers were separated.

The aqueous layer was further extracted with CH₂Cl₂ (25 mL), and the combined organic layers were dried (MgSO₄), filtered, and concentrated to give compound 1a (1.66 g, 99%) as a white solid: 1H NMR (300 MHz, CDCl₃) δ 8.18 (dd, J=1.7, 8.0 Hz, 1H), 7.67 (ddd, J=1.7, 7.2, 8.3 Hz, 1H), 7.52 (d, J=8.3 Hz, 1H), 7.33 (ddd, J=1.1, 7.2, 8.3 Hz, 1H), 4.76 (dd, J=7.7, 8.6 Hz, 2H), 4.37 (t, J=8.0, 8.6 Hz, 2H).

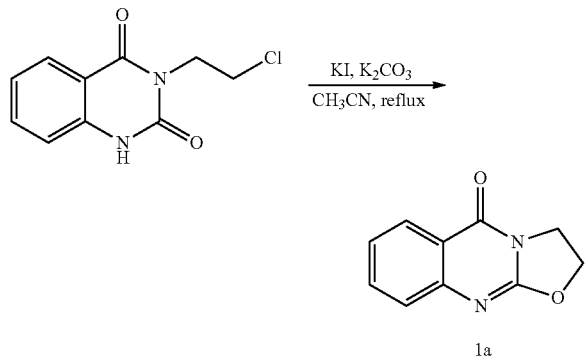

Example 16

Synthesis of 2H-Oxazolo[3,2-a]thieno[2,3-d]pyrimidin-5(3H)-one (Compound 1b)

The compound was prepared as a light yellow solid according to Sugiyama M et al, *Chem Pharm Bull* 37, 2091-2102 (1989); incorporated by reference herein.

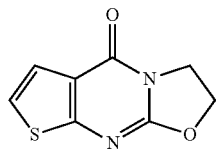

Example 17

Synthesis of 7,9-dibromo-2H-oxazolo[2,3-b]quinazolin-5(3H)-one (Compound 1c) and 7-bromo-2H-oxazolo[2,3-b]quinazolin-5(3H)-one (Compound 1d)

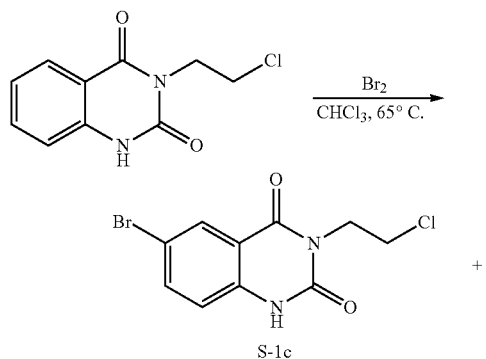

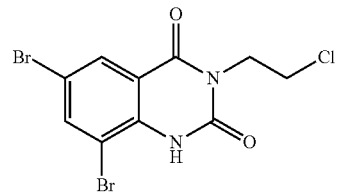

To a stirred solution of 3-(2-Chloroethyl)-2,4(1H,3H)-quinazolinedione (2.5 g, 11.1 mmol) in CHCl₃ (50 mL) at room temperature, was added Bromine (1.14 mL, 22.2 mmol). The resulting solution was heated at 65° C. for 2 days at which time another 2 equivalents of bromine was added. Heating continued for 2 more days and another 2 equivalents of bromine was added. After 3 more days of heating, 4 equivalents of bromine were added to the solution and heating continued for 3 days. The solution was then cooled to room temperature, basified with sat. Na₂CO₃ and extracted with CHCl₃ (5×50 mL). The combined organic extracts were dried over Na₂SO₄ and concentrated affording compound 1. The crude product was carried on without any further purification.

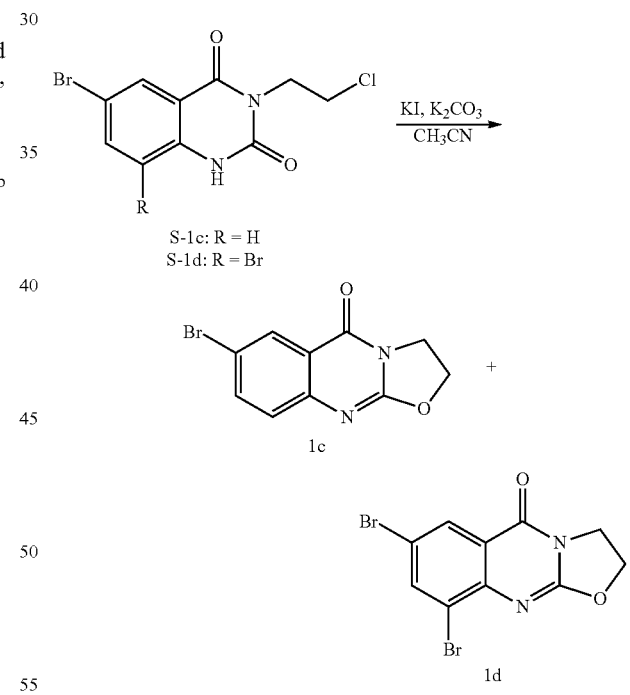

The crude reaction mixture from above was dissolved in CH₃CN (15 ml) and K₂CO₃ (1.37 g, 9.9 mmol) and KI (82 mg, 0.5 mmol) was added. The reaction mixture was heated to 80° C. overnight. The mixture was then concentrated, partitioned between CH₂Cl₂ (75 mL) and H₂O (20 mL), and the layers were separated. The aqueous layer was further extracted with CH₂Cl₂ (25 mL), and the combined organic layers were dried (Na₂SO₄), filtered, and concentrated to give the crude mixture. The compounds were separated on silica gel eluting with 10-25% EtOAc/CH₂Cl₂.

7,9-dibromo-2H-oxazolo[2,3-b]quinazolin-5(3H)-one (1c)

The title compound was isolated in 19% yield (327 mg) as an off-white solid. R$_f$=0.4 (20% EtOAc/CH$_2$Cl$_2$). $^1$H NMR (300 MHz, DMSO-d$_6$) δ 8.24 (d, J=2.48 Hz, 1H), 8.07 (d, J=2.20 Hz, 1H), 4.75 (t, J=8.26 Hz, 2H), 4.24 (t, J=8.26 Hz, 2H).

7-bromo-2H-oxazolo[2,3-b]quinazolin-5(3H)-one (1d)

The title compound was isolated in 29% yield (385 mg) as an off-white solid. R$_f$=0.2 (20% EtOAc/CH$_2$Cl$_2$). $^1$H NMR (300 MHz, DMSO-d$_6$) δ 8.08 (d, J=2.75 Hz, 1H), 7.85 (dd, J=2.48, 8.53 Hz, 1H), 7.39 (d, J=8.53 Hz, 1H), 4.70 (t, J=7.98, Hz, 2H), 4.23 (t, J=8.26 Hz, 2H).

Example 18

Synthesis of Ethyl 1-benzyl-4-(trifluoromethylsulfonyloxy)-1,2,5,6-tetrahydropyridine-3-carboxylate (Compound 2)

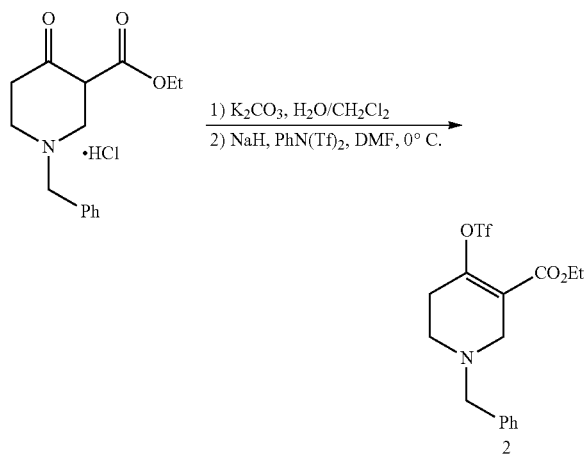

To a suspension of ethyl 1-benzyl-4-oxo-3-piperidinecarboxylate hydrochloride (3.32 g, 11.1 mmol) in H$_2$O (30 mL) was added potassium carbonate (2.76 g, 20.0 mmol), and the mixture was extracted with CH$_2$Cl$_2$ (3×40 mL). The combined organic layers were dried (Na$_2$SO$_4$), filtered, and concentrated to give the free base (100%) as an oil which was used without further purification. This keto-ester was dissolved in anhydrous DMF (20 mL), fitted with a septum, nitrogen inlet and cooled to 0° C. NaH (60% in mineral oil, 668 mg, 16.7 mmol) was added in one portion, and the solution was stirred at 0° C. for 10 min. N-phenyl-bis(trifluoromethanesulfonimide) (4.36 g, 12.2 mmol) was added in one portion, and the solution was stirred at 0° C. for 1.5 h. Water (50 mL) was then added and the resulting mixture was extracted with EtOAc (3×50 mL). The combined organic layers were washed with H$_2$O (20 mL), dried (Na$_2$SO$_4$), filtered, and concentrated. The residue was purified by flash chromatography eluting with 0-15% EtOAc/hexanes to give Compound 2 (3.60 g, 83%) as a yellow oil: $^1$H NMR (300 MHz, CDCl$_3$) δ 7.34-7.25 (comp, 5H), 4.27 (q, J=7.2 Hz, 2H), 3.67 (s, 2H), 3.42 (t, J=2.7 Hz, 2H), 2.71 (t, J=5.4 Hz, 2H), 2.53-2.49 (m, 2H), 1.31 (t, J=7.2 Hz, 3H).

Example 19

Synthesis of Ethyl 1-benzyl-4-(4-fluorophenyl)-1,2,5,6-tetrahydropyridine-3-carboxylate (Compound 3d)

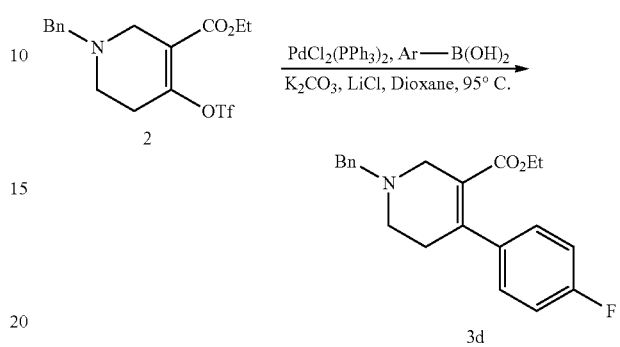

A 250 mL round bottom flask was charged with triflate 2 (2.71 g, 6.9 mmol), 4-fluorophenyl boronic acid (2.11 g, 15.1 mmol), PdCl$_2$(PPh$_3$)$_2$ (147 mg, 0.21 mmol), LiCl (875 mg, 20.6 mmol), and K$_2$CO$_3$ (5.71 g, 41.3 mmol). The flask was evacuated and back-flushed with argon three times, anhydrous dioxane (100 mL) was added, and the flask was heated to 95° C. overnight. The flask was cooled to room temperature and CHCl$_3$ (500 mL) was added. The mixture was then washed with water (2×150 mL), brine (150 mL), dried (MgSO$_4$), and concentrated. The residue was purified by flash chromatography eluting with 0-30% EtOAc/hexanes to give 3d (1.98 g, 85%): R$_f$=0.34 (20% EtOAc/hexanes); $^1$H NMR (300 MHz, CDCl$_3$) δ 7.20-7.48 (m, 5H), 7.10 (dd, J=5.5, 8.8 Hz, 2H), 6.99 (t, J=8.8 Hz, 2H), 3.91 (q, J=7.2 Hz, 2H), 3.70 (s, 2H), 3.31-3.49 (m, 2H), 2.61-2.72 (m, 2H), 2.42-2.56 (m, 2H), 0.91 (t, J=7.2 Hz, 3H).

Example 20

Synthesis of Ethyl 1-benzyl-4-(3-fluorophenyl)-1,2,5,6-tetrahydropyridine-3-carboxylate (3e)

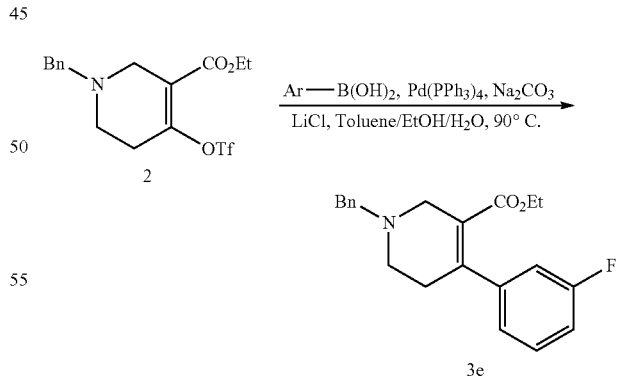

A 100 mL round bottom flask was charged with triflate 2 (800 mg, 2.0 mmol), 3-fluorophenyl boronic acid (312 mg, 2.2 mmol), LiCl (258 mg, 6.1 mmol), Na$_2$CO$_3$ (645 mg, 6.1 mmol). Pd(PPh$_3$)$_4$ (71.0 mg, 0.061 mmol). The flask was evacuated and back-flushed with argon three times; toluene (10 mL), EtOH (10 mL) and water (3 mL) were then added. The resultant mixture was heated to 85° C. for 20 h. The flask was cooled to room temperature, and EtOAc (40 mL) and water (15 mL) were added. The organic layer was separated and, the aqueous layer was extracted with EtOAc (15 mL). The combined organic layers were dried ($Na_2SO_4$) and concentrated. The residue was purified by flash chromatography eluting with 15-25% EtOAc/hexanes to give 3e (490 mg, 71%) as a light yellow oil: $R_f$=0.55 (25% EtOAc/hexanes); $^1$H NMR (300 MHz, $CDCl_3$) δ 7.40-7.22 (comp, 6H), 6.83-6.95 (comp, 3H), 3.90 (q, J=7.2 Hz, 2H), 3.69 (s, 2H), 3.37 (t, J=2.7 Hz, 2H), 2.66 (t, J=5.4 Hz, 2H), 2.49 (m, 2H) 0.89 (t, J=7.2 Hz, 3H).

Example 21

Synthesis of Ethyl 1-benzyl-4-phenyl-1,2,5,6-tetrahydropyridine-3-carboxylate (Compound 3a)

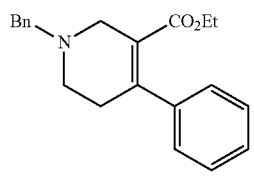 [SMILES: CCOC(=O)C1=C(c2ccccc2)CCN(Cc2ccccc2)C1]

Compound 3a was prepared from 2 and phenylboronic acid in 67% yield using the method of Example 19 or Example 20, described above. $^1$H NMR (300 MHz, $CDCl_3$) δ 7.39-7.22 (comp, 8H), 7.18-7.13 (m, 2H), 3.86 (q, J=7.2 Hz, 2H), 3.70 (s, 2H), 3.39 (t, J=2.7 Hz, 2H), 2.65 (t, J=5.4 Hz, 2H), 2.56-2.50 (m, 2H), 0.84 (t, J=7.2 Hz, 3H).

Example 22

Synthesis of Ethyl 1-benzyl-4-(p-tolyl)-1,2,5,6-tetrahydropyridine-3-carboxylate (3b)

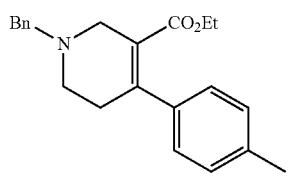 [SMILES: CCOC(=O)C1=C(c2ccc(C)cc2)CCN(Cc2ccccc2)C1]

Compound 3b was prepared from 2 and 4-methylphenylboronic acid in 81% yield using the method of Example 19 or Example 20, described above. $^1$H NMR (300 MHz, $CDCl_3$) δ 7.40-7.25 (comp, 5H), 7.11 (d, J=7.5 Hz, 2H), 7.03 (d, J=7.5 Hz, 2H), 3.90 (q, J=7.2 Hz, 2H), 3.68 (s, 2H), 3.38 (t, J=3.0 Hz, 2H), 2.64 (t, J=2.4 Hz, 2H), 2.55-2.47 (m, 2H), 2.33 (s, 3H), 0.89 (t, J=7.2 Hz, 3H).

Example 23

Synthesis of Ethyl 1-benzyl-4-(2,3-dihydrobenzo[b][1,4]dioxin-5-yl)-1,2,5,6-tetrahydropyridine-3-carboxylate (Compound 3c)

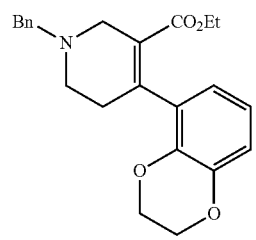 [SMILES: CCOC(=O)C1=C(c2cccc3c2OCCO3)CCN(Cc2ccccc2)C1]

Compound 3c was prepared from 2 and (2,3-dihydrobenzo[b][1,4]dioxin-5-yl) boronic acid in 81% yield using the method of Example 19 or Example 20, described above. $^1$H NMR (300 MHz, $CDCl_3$) δ 7.39-7.22 (comp, 5H), 6.78 (d, J=8.1 Hz, 1H), 6.68 (d, J=2.1 Hz, 1H), 6.63 (dd, J=1.8, 8.1 Hz, 1H), 4.24 (s, 4H), 3.94 (q, J=6.9 Hz, 2H), 3.67 (s, 2H), 3.36 (t, J=2.4 Hz, 2H), 2.62 (t, J=2.1 Hz, 2H), 2.50-2.45 (m, 2H), 0.96 (t, J=6.9 Hz, 3H).

Example 24

Synthesis of Ethyl 1-benzyl-4-(4-(trifluoromethyl)phenyl)-1,2,5,6-tetrahydropyridine-3-carboxylate (Compound 3f)

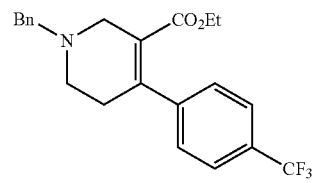

Compound 3f was prepared from 2 and 4-trifluoromethylphenyl boronic acid in 82% yield using the method of Example 19 or Example 20, described above. $^1$H NMR (300 MHz, $CDCl_3$) δ 7.57 (d, J=8.1 Hz, 2H), 7.39-7.27 (comp, 5H), 7.23 (d, J=8.1 Hz, 2H), 3.87 (q, J=7.2 Hz, 2H), 3.70 (s, 2H), 3.40 (t, J=2.7 Hz, 2H), 2.66 (t, J=5.4 Hz, 2H), 2.52-2.47 (m, 2H), 0.84 (t, J=7.2 Hz, 3H).

Example 25

Synthesis of Ethyl 1-benzyl-4-(3-(trifluoromethyl)phenyl)-1,2,5,6-tetrahydropyridine-3-carboxylate (Compound 3g)

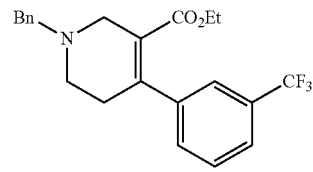

Compound 3g was prepared from 2 and 3-trifluoromethylphenyl boronic acid in 74% yield using the method of Example 19 or Example 20, described above. $^1$H NMR (300 MHz, CDCl$_3$) δ 7.55-7.24 (comp, 9H), 3.86 (q, J=7.2 Hz, 2H), 3.69 (s, 2H), 3.39 (t, J=2.7 Hz, 2H), 2.66 (t, J=5.4 Hz, 2H), 2.54-2.48 (m, 2H), 0.82 (t, J=7.2 Hz, 3H).

Example 26

Synthesis of Ethyl 1-benzyl-4-(4-(dimethylamino)phenyl)-1,2,5,6-tetrahydropyridine-3-carboxylate (Compound 3h)

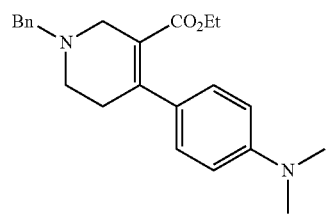

Compound 3h was prepared from 2 and 4-N,N-dimethylaminophenyl boronic acid in 67% yield using the method of Example 19 or Example 20, described above. $^1$H NMR (300 MHz, CDCl$_3$) δ 7.39-7.28 (comp, 5H), 7.05 (d, J=9.0 Hz, 2H), 6.64 (d, J=9.0 Hz, 2H), 3.96 (q, J=7.2 Hz, 2H), 3.67 (s, 2H), 3.38 (t, J=2.4 Hz, 2H), 2.94 (s, 6H), 2.63 (t, J=5.1 Hz, 2H), 2.55-2.48 (m, 2H), 0.95 (t, J=7.2 Hz, 3H).

Example 27

Synthesis of Ethyl 1-benzyl-4-(4-carbamoylphenyl)-1,2,5,6-tetrahydropyridine-3-carboxylate (Compound 3i)

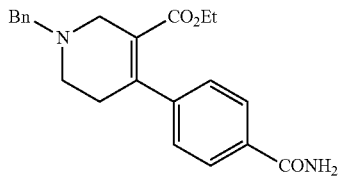 [SMILES: CCOC(=O)C1=C(c2ccc(C(N)=O)cc2)CCN(Cc2ccccc2)C1]

Compound 3i was prepared from 2 and 4-aminocarbonylphenyl boronic acid as a light yellow solid (134 mg, 82%) using the method of Example 19 or Example 20, described above. mp=184.0-186.0° C.; $^1$H NMR (300 MHz, CDCl$_3$) δ 7.76 (d, J=7.8 Hz, 2H), 7.39-7.30 (comp, 5H), 7.23 (d, J=7.8 Hz, 2H), 3.89 (q, J=7.2 Hz, 2H), 3.69 (s, 2H), 3.39 (t, J=2.7 Hz, 2H), 2.66 (t, J=5.4 Hz, 2H), 2.52-2.49 (m, 2H), 0.88 (t, J=7.2 Hz, 3H).

Example 28

Synthesis of Ethyl 4-([1,1'-biphenyl]-4-yl)-1-benzyl-1,2,5,6-tetrahydropyridine-3-carboxylate (Compound 3j)

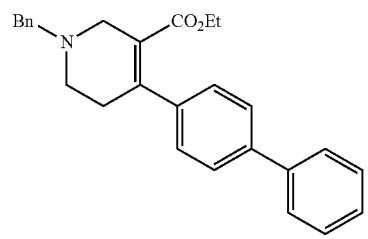 [SMILES: CCOC(=O)C1=C(c2ccc(-c3ccccc3)cc2)CCN(Cc2ccccc2)C1]

Compound 3j was prepared from 2 and 4-N,N-dimethylaminolphenyl boronic acid in 80% yield using the method of Example 19 or Example 20, described above: $^1$H NMR (300 MHz, CDCl$_3$) δ 7.61-7.19 (comp, 14H), 3.91 (q, J=7.2 Hz, 2H), 3.70 (s, 2H), 3.41 (t, J=2.7 Hz, 2H), 2.68 (t, J=5.1 Hz, 2H), 2.60-2.52 (m, 2H), 0.87 (t, J=7.2 Hz, 3H).

Example 29

Synthesis of Ethyl 1-benzyl-4-(1-(tert-butoxycarbonyl)-1H-pyrrol-2-yl)-1,2,5,6-tetra hydropyridine-3-carboxylate (Compound 3k)

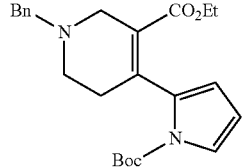

Compound 3k was prepared from 2 and N-Boc-2-pyrroleboronic acid as a yellow oil (300 mg, 67%) using the method of Example 19 or Example 20, described above: R$_f$=0.43 (15% EtOAc/hexanes); $^1$H NMR (300 MHz, CDCl$_3$) δ 7.38-7.27 (comp, 5H), 7.26-7.22 (m, 1H), 6.12 (t, J=3.3 Hz, 1H), 5.92 (dd, J=2.1, 3.3 Hz, 1H), 3.89 (q, J=7.2 Hz, 2H), 7.65 (br. s, 2H), 3.48 (br. s, 1H), 3.25 (br. s, 1H), 2.61 (br. s, 2H), 2.47 (br. s, 2H), 1.53 (s, 9H), 0.96 (t, J=7.2 Hz, 3H).

Example 30

Synthesis of Ethyl 1-benzyl-4-(4-(ethoxycarbonyl)phenyl)-1,2,5,6-tetrahydropyridine-3-carboxylate (Compound 3l)

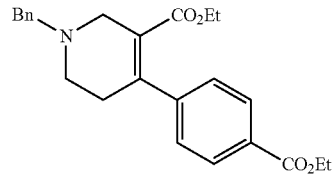 [SMILES: CCOC(=O)C1=C(c2ccc(C(=O)OCC)cc2)CCN(Cc2ccccc2)C1]

Compound 3l was prepared from 2 and 4-ethoxycarbonyllphenylboronic acid in 50% yield using the method of Example 19 or Example 20, described above: $^1$H NMR (300 MHz, CDCl$_3$) δ 7.98 (d, J=8.4 Hz, 2H), 7.39-7.25 (comp, 5H), 7.21 (d, J=8.4 Hz, 2H), 4.36 (q, J=7.2 Hz, 2H), 3.87 (q, J=7.2 Hz, 2H), 3.69 (s, 2H), 3.39 (t, J=2.7 Hz, 2H), 2.66 (t, J=5.4 Hz, 2H), 2.53-2.45 (m, 2H), 1.38 (t, J=7.2 Hz, 3H), 0.86 (t, J=7.2 Hz, 3H).

Example 31

Synthesis of Ethyl 1-benzyl-4-(thiophen-2-yl)-1,2,5,6-tetrahydropyridine-3-carboxylate (3m)

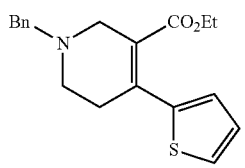

Compound 3m was prepared from 2 and 2-thienylboronic acid as a yellow oil (123 mg, 88%) using the method of Example 19 or Example 20, described above: R$_f$=0.33 (25% EtOAc/hexanes); $^1$H NMR (300 MHz, CDCl$_3$) δ 7.38-7.27 (comp, 5H), 7.26-7.24 (M, 1H), 6.97-6.93 (comp, 2H), 4.03 (q, J=7.2 Hz, 2H), 3.66 (s, 2H), 3.36 (t, J=2.7 Hz, 2H), 2.67 (t, J=5.4 Hz, 2H), 2.60-2.54 (m, 2H), 1.05 (t, J=7.2 Hz, 3H).

Example 32

Synthesis of Ethyl 1-benzyl-4-(5-methylthiophen-2-yl)-1,2,5,6-tetrahydropyridine-3-carboxylate (Compound 3n)

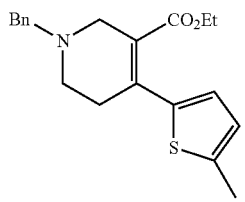

Compound 3n was prepared from 2 and 5-methyl-2-thienylboronic acid as a yellow oil (1.07 g, 86%) using the method of Example 19 or Example 20, described above: $^1$H NMR (300 MHz, CDCl$_3$) δ 7.38-7.25 (comp, 5H), 6.73 (d, J=3.6 Hz, 1H), 6.60 (m, 1H), 4.07 (q, J=7.2 Hz, 2H), 3.65 (s, 2H), 3.34 (t, J=2.7 Hz, 2H), 2.64 (t, J=5.1 Hz, 2H), 2.45 (s, 3H), 1.10 (t, J=7.2 Hz, 3H).

Example 33

Synthesis of Ethyl 4-(4-acetylphenyl)-1-benzyl-1,2,5,6-tetrahydropyridine-3-carboxylate (Compound 3p)

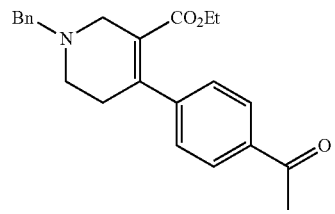 [SMILES: CCOC(=O)C1=C(c2ccc(C(C)=O)cc2)CCN(Cc2ccccc2)C1]

Compound 3p was prepared from 2 and 4-acetylphenylboronic acid in 77% yield using the method of Example 19 or Example 20, described above: $^1$H NMR (300 MHz, CDCl$_3$) δ 7.91 (d, J=6.6 Hz, 2H), 7.40-7.25 (comp, 5H), 7.24 (d, J=6.6 Hz, 2H), 3.89 (q, J=7.2 Hz, 2H), 3.69 (s, 2H), 3.39 (t, J=2.4 Hz, 2H), 2.66 (t, J=5.7 Hz, 2H), 2.59 (s, 3H), 2.53-2.47 (m, 2H), 0.88 (t, J=7.2 Hz, 3H).

Example 34

Synthesis of Ethyl 1-benzyl-4-(3-methoxyphenyl)-1,2,5,6-tetrahydropyridine-3-carboxylate (Compound 3q)

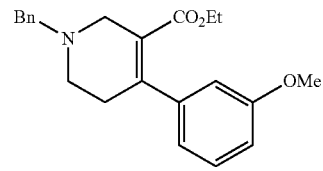 [SMILES: CCOC(=O)C1=C(c2cccc(OC)c2)CCN(Cc2ccccc2)C1]

Compound 3q was prepared from 2 and 3-methoxyphenylboronic acid as a yellow oil (1.10 g, 95%) using the method of Example 19 or Example 20, described above. R$_f$=0.18 (15% EtOAc/hexanes); $^1$H NMR (300 MHz, CDCl$_3$) δ 7.39-7.27 (m, 5H), 7.21 (t, J=7.8 Hz, 1H), 6.79 (m, 1H), 6.74-6.68 (m, 2H), 3.90 (q, J=7.2 Hz, 2H), 3.78 (s, 3H), 3.69 (2, 2H), 3.38 (t, J=2.7 Hz, 2H), 2.54-2.50 (m, 2H), 0.87 (t, J=7.2 Hz, 3H).

Example 35

Synthesis of Ethyl 1-benzyl-4-(4-methoxyphenyl)-1,2,5,6-tetrahydropyridine-3-carboxylate (Compound 3r)

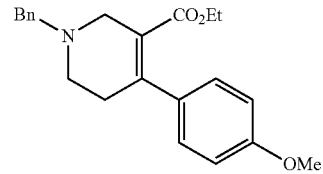 [SMILES: CCOC(=O)C1=C(c2ccc(OC)cc2)CCN(Cc2ccccc2)C1]

Compound 3r was prepared from 2 and 4-methoxyphenylboronic acid as a yellow oil (497 mg, 92%) using the method of Example 19 or Example 20, described above. $R_f$=0.18 (15% EtOAc/hexanes); $^1$H NMR (300 MHz, CDCl$_3$) δ 7.38-7.25 (m, 5H), 7.09 (d, J=8.7 Hz, 2H), 6.84 (d, J=8.7 Hz, 2H), 3.94 (q, J=7.8 Hz, 2H), 3.80 (s, 3H), 3.67 (s, 2H), 3.36 (t, J=2.4 Hz, 2H), 2.64 (t, J=5.4 Hz, 2H), 2.53-2.49 (m, 2H), 0.92 (t, J=7.8 Hz, 3H).

Example 36

Synthesis of Ethyl 1-benzyl-4-(4-((tert-butoxycarbonyl)amino)phenyl)-1,2,5,6-tetrahydropyridine-3-carboxylate (Compound 3s)

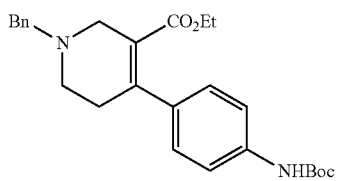 [SMILES: CCOC(=O)C1=C(c2ccc(NC(=O)OC(C)(C)C)cc2)CCN(Cc2ccccc2)C1]

Compound 3s was prepared from 2 and 3-(N-Boc-amino)phenylboronic acid as a light yellow solid (720 mg, 94%) using the method of Example 19 or Example 20, described above. mp=150.0-151.1° C.; $R_f$=0.10 (15% EtOAc/hexanes); $^1$H NMR (300 MHz, CDCl$_3$) δ 7.38-7.26 (m, 7H), 7.08 (d, J=8.7 Hz, 2H), 6.45 (br. s, 1H), 3.90 (q, J=7.2 Hz, 2H), 3.67 (s, 2H), 3.37 (t, J=2.4 Hz, 2H), 2.63 (t, J=5.4 Hz, 2H), 2.51-2.47 (m, 2H), 1.47 (s, 9H), 0.92 (t, J=7.2 Hz, 3H).

Example 37

Synthesis of Ethyl 1-benzyl-4-(4-ethylphenyl)-1,2,5,6-tetrahydropyridine-3-carboxylate (Compound 3t)

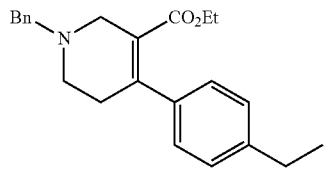 [SMILES: CCOC(=O)C1=C(c2ccc(CC)cc2)CCN(Cc2ccccc2)C1]

Compound 3t was prepared from 2 and 4-ethylphenylboronic acid as a light yellow oil (445 mg, 94%) using the method of Example 19 or Example 20, described above. $R_f$=0.20 (15% EtOAc/hexanes); $^1$H NMR (300 MHz, CDCl$_3$) δ 7.39-7.26 (m, 5H), 7.13 (d, J=7.8 Hz, 2H), 7.05 (d, J=7.8 Hz, 2H), 3.88 (q, J=7.2 Hz, 2H), 3.69 (s, 2H), 3.38 (t, J=2.4 Hz, 2H), 2.67-2.60 (m, 4H), 2.54-2.49 (m, 2H), 1.23 (t, J=7.5 Hz, 3H), 0.85 (t, J=7.2 Hz, 3H).

Example 38

Synthesis of Ethyl 1-benzyl-4-(4-isopropylphenyl)-1,2,5,6-tetrahydropyridine-3-carboxylate (Compound 3u)

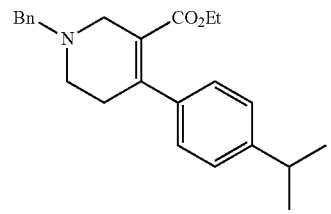 [SMILES: CCOC(=O)C1=C(c2ccc(C(C)C)cc2)CCN(Cc2ccccc2)C1]

Compound 3u was prepared from 2 and 4-isopropylphenylboronic acid as a light yellow oil (344 mg, 94%) using the method of Example 19 or Example 20, described above; $R_f$=0.25 (15% EtOAc/hexanes); $^1$H NMR (300 MHz, CDCl$_3$) δ 7.40-7.26 (m, 5H), 7.15 (d, J=8.4 Hz, 2H), 7.06 (d, J=8.4 Hz, 2H), 3.84 (q, J=7.2 Hz, 2H), 3.69 (s, 2H), 3.38 (t, J=2.4 Hz, 2H), 2.87 (hep, J=6.9 Hz, 1H), 2.65 (t, J=5.7 Hz, 2H), 2.53-2.49 (m, 2H), 1.23 (d, J=6.9 Hz, 6H), 0.80 (t, J=7.2 Hz, 3H).

Example 39

Synthesis of (E)-Ethyl 1-benzyl-4-styryl-1,2,5,6-tetrahydropyridine-3-carboxylate (Compound 3v)

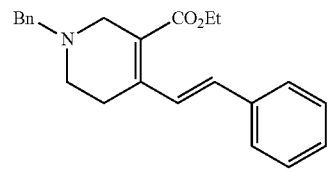 [SMILES: CCOC(=O)C1=C(/C=C/c2ccccc2)CCN(Cc2ccccc2)C1]

Compound 3v was prepared from 2 and trans-styrylboronic acid as a yellow oil (248 mg, 70%) using the method of Example 19 or Example 20, described above. $R_f$=0.20 (15% EtOAc/hexanes); $^1$H NMR (300 MHz, CDCl$_3$) δ 8.09 (d, J=16.2 Hz, 1H), 7.48-7.44 (2H), 7.39-7.23 (m, 8H), 6.77 (d, J=16.2 Hz, 2H), 4.23 (q, J=7.2 Hz, 2H), 3.65 (s, 2H), 3.40 (s, 2H), 2.62 (s, 2H), 1.32 (t, J=7.2 Hz, 3H).

Example 40

Synthesis of Ethyl 1-benzyl-4-(2-fluorophenyl)-1,2,5,6-tetrahydropyridine-3-carboxylate (Compound 3x)

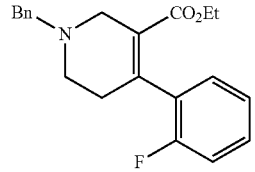

Compound 3x was prepared from 2 and 2-fluorophenylboronic acid as a yellow oil (570 mg, 91%) using the method of Example 19 or Example 20, described above. R$_f$=0.21 (15% EtOAc/hexanes); $^1$H NMR (300 MHz, CDCl$_3$) δ 7.39-7.21 (m, 6 H), 7.10-6.95 (3H), 3.90 (q, J=7.2 Hz, 2H), 3.70 (s, 2H), 3.42 (t, J=3.0 Hz, 2H), 2.65 (t, J=5.4 Hz, 2H), 2.52-2.48 (m, 2H), 0.87 (t, J=7.2 Hz, 3H).

Example 41

Synthesis of Ethyl 1-benzyl-4-(m-tolyl)-1,2,5,6-tetrahydropyridine-3-carboxylate (Compound 3y)

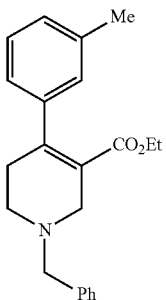

Compound 3y was prepared using the method of Example 19 or Example 20, described above in 61% yield from 2 and m-tolyl boronic acid. $^1$H NMR (300 MHz, CDCl$_3$) δ 7.43-7.26 (m, 5H), 7.20 (t, J=7.6 Hz, 1H), 7.08 (d, J=7.7 Hz, 1H), 6.99-6.91 (m, 2H), 3.90 (q, J=7.2 Hz, 2H), 3.69 (s, 2H), 3.39 (t, J=2.5 Hz, 2H), 2.65 (t, J=5.5, Hz, 2H), 2.52 (dq, J=5.5, 2.8 Hz, 2H), 2.33 (s, 3H), 0.86 (t, J=7.0 Hz, 3H).

Example 42

Synthesis of Ethyl 1-benzyl-4-(o-tolyl)-1,2,5,6-tetrahydropyridine-3-carboxylate (Compound 3z)

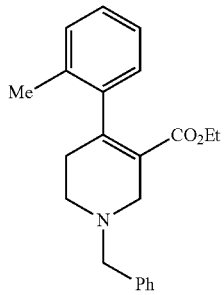 [SMILES: CCOC(=O)C1=C(c2ccccc2C)CCN(Cc2ccccc2)C1]

Compound 3z was prepared using the method of Example 19 or Example 20, described above, in 91% yield from 2 and o-tolyl boronic acid. $^1$H NMR (300 MHz, CDCl$_3$) δ 7.44-7.26 (comp., 5H), 7.19-7.07 (m, 3H), 7.00-6.88 (m, 1H), 3.84 (qd, J=1.2, 7.1 Hz, 2H), 3.78-3.63 (m, 2H), 3.50 (d, J=16.5 Hz, 1H), 3.31 (d, J=16.8 Hz, 1H), 2.79-2.64 (m, 1H), 2.64-2.48 (m, 1H), 2.40 (tt, J=2.86, 5.4 Hz, 2H), 2.19 (s, 3H), 0.80 (t, J=7.2 Hz, 3H).

Example 43

Synthesis of Ethyl 1-benzyl-4-(3-(dimethylamino)phenyl)-1,2,5,6-tetrahydropyridine-3-carboxylate (Compound 3aa)

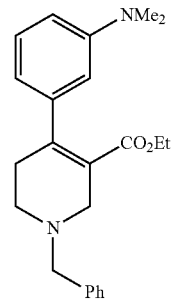 [SMILES: CCOC(=O)C1=C(c2cccc(N(C)C)c2)CCN(Cc2ccccc2)C1]

Compound 3aa was prepared using the method of Example 19 or Example 20, described above, in 99% yield from 2 and 3-(N,N-Dimethylamino)phenyl boronic acid. $^1$H NMR (300 MHz, CDCl$_3$) δ 7.40-7.14 (comp., 6H), 6.67-6.62 (m, 1H), 6.54-6.49 (m, 2H), 3.89 (q, J=7.2 Hz, 2H), 3.68 (s, 2H), 3.38 (t, J=2.6 Hz, 2H), 2.91 (s, 6H), 2.68-2.61 (m, 2H), 2.54 (td, J=2.6, 5.2 Hz, 2H), 0.87 (t, J=7.0 Hz, 3H).

Example 44

Synthesis of Ethyl 1-benzyl-4-(2-(dimethylamino)phenyl)-1,2,5,6-tetrahydropyridine-3-carboxylate (Compound 3bb)

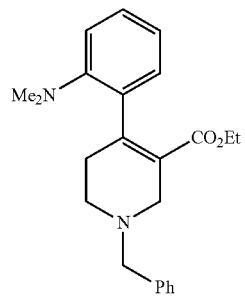 [SMILES: CCOC(=O)C1=C(c2ccccc2N(C)C)CCN(Cc2ccccc2)C1]

Compound 3bb was prepared using the method of Example 19 or Example 20, described above, in 52% yield from 2 and 2-(N,N-Dimethylamino)phenylboronic acid. $^1$H NMR (300 MHz, CDCl$_3$) δ 7.41-7.25 (comp., 5H), 7.16 (t, J=7.6 Hz, 1H), 6.64 (dd, J=7.4, 2.5 Hz, 1H), 6.55-6.48 (m, 2H), 3.89 (qd, J=7.2, 1.1 Hz, 2H), 3.68 (s, 2H), 3.37 (br. s., 2H), 2.91 (s, 5H), 2.65 (t, J=5.8 Hz, 2H), 2.53 (br. s., 2H), 0.86 (td, J=7.2, 1.1 Hz, 3H).

Example 45

Synthesis of Ethyl 1-benzyl-4-(3,4-dimethoxyphenyl)-1,2,5,6-tetrahydropyridine-3-carboxylate (Compound 3dd)

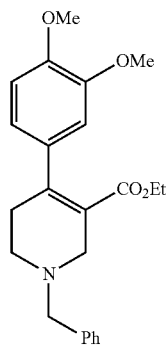

Compound 3dd was prepared using the method of Example 19 or Example 20, described above in 93% yield from 2 and 3,4-Dimethoxyphenylboronic acid. $^1$H NMR (300 MHz, CDCl$_3$) δ 7.42-7.26 (comp., 5H), 6.87-6.78 (m, 1H), 6.75-6.66 (m, 2H), 3.92 (q, J=7.2 Hz, 2H), 3.87 (s, 3H), 3.84 (s, 4H), 3.68 (s, 2H), 3.40-3.33 (m, 2H), 2.69-2.59 (m, 2H), 2.52 (dt, J=2.8, 5.4 Hz, 2H), 0.92 (t, J=7.2 Hz, 3H).

Example 46

Synthesis of Ethyl 1-benzyl-4-(3,4-bis(benzyloxy)phenyl)-1,2,5,6-tetrahydropyridine-3-carboxylate (Compound 3ff)

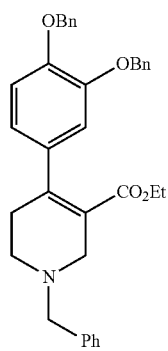 [SMILES: CCOC(=O)C1=C(c2ccc(OCc3ccccc3)c(OCc3ccccc3)c2)CCN(Cc2ccccc2)C1]

Compound 3ff was prepared using the method of Example 19 or Example 20, described above in 87% yield from 2 and 2-[3,4-bis(benzyloxy)phenyl]-4,4,5,5-tetramethyl-1,3,2-dioxaborolane. $^1$H NMR (300 MHz, CDCl3) δ 7.47-7.27 (comp., 15H), 6.87 (d, J=8.3 Hz, 1H), 6.78 (d, J=2.2 Hz, 1H), 6.68 (dd, J=1.9, 8.3 Hz, 1H), 5.13 (d, J=12.1 Hz, 4H), 3.81 (q, J=7.2 Hz, 2H), 3.67 (s, 2H), 3.38-3.29 (m, 2H), 2.67-2.57 (m, 2H), 2.45 (dt, J=2.6, 5.6 Hz, 2H), 0.82 (t, J=7.2 Hz, 3H).

Example 47

Synthesis of Ethyl 1-benzyl-4-(2,3-dihydrobenzo[b][1,4]dioxin-6-yl)-1,2,5,6-tetrahydropyridine-3-carboxylate (Compound 3gg)

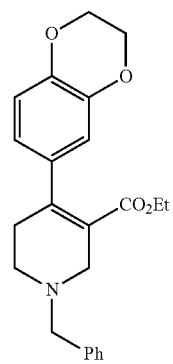 [SMILES: CCOC(=O)C1=C(c2ccc3c(c2)OCCO3)CCN(Cc2ccccc2)C1]

Compound 3gg was prepared using the method of Example 19 or Example 20, described above in 99% yield from 2 and 1,4-Benzodioxane-6-boronic acid. $^1$H NMR (300 MHz, CDCl$_3$) δ 7.41-7.26 (comp., 5H), 6.79 (d, J=8.3 Hz, 1H), 6.68 (d, J=2.2 Hz, 1H), 6.66-6.59 (m, 1H), 4.24 (s, 4H), 3.95 (q, J=7.2 Hz, 2H), 3.67 (s, 2H), 3.36 (t, J=2.6 Hz, 2H), 2.68-6.58 (m, 2H), 2.53-2.41 (m, 2H), 0.96 (t, J=7.2 Hz, 3H).

Example 48

Synthesis of Ethyl 1-benzyl-4-(2-(trifluoromethyl)phenyl)-1,2,5,6-tetrahydropyridine-3-carboxylate (Compound 3hh)

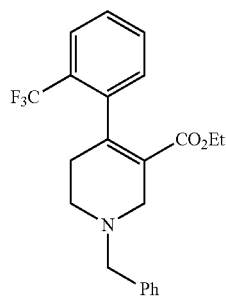 [SMILES: CCOC(=O)C1=C(c2ccccc2C(F)(F)F)CCN(Cc2ccccc2)C1]

Compound 3hh was prepared using the method of Example 19 or Example 20, described above in 80% yield from 2 and (2-Trifluoromethyl)phenyl boronic acid. $^1$H NMR (300 MHz, CDCl$_3$) δ 7.63 (d, J=8.0 Hz, 1H), 7.49 (d, J=7.71 Hz, 1H), 7.42-7.27 (m, 6H), 7.17 (d, J=7.7 Hz, 1H), 3.87-3.73 (m, 3H), 3.68-3.50 (m, 2H), 3.27 (dd, J=2.8, 16.5 Hz, 1H), 2.54-2.38 (m, 3H), 0.78 (t, J=7.0 Hz, 3H).

Example 49

Synthesis of Ethyl 1-benzyl-4-(4-(trifluoromethoxy)phenyl)-1,2,5,6-tetrahydropyridine-3-carboxylate (Compound 3ii)

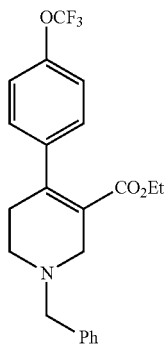

Compound 3ii was prepared using the method of Example 19 or Example 20, described above in 86% yield from 2 and 4-Trifluoromethoxyphenylboronic acid. ¹H NMR (300 MHz, CDCl₃) δ 7.42-7.26 (comp., 5H), 7.16 (s, 4H), 3.88 (q, J=7.2 Hz, 2H), 3.69 (s, 2H), 3.38 (t, J=2.5 Hz, 2H), 2.65 (t, J=5.8 Hz, 2H), 2.53-2.46 (m, 2H), 0.84 (t, J=7.2 Hz, 3H).

Example 50

Synthesis of Ethyl 1-benzyl-4-(3-(trifluoromethoxy)phenyl)-1,2,5,6-tetrahydropyridine-3-carboxylate (Compound 3jj)

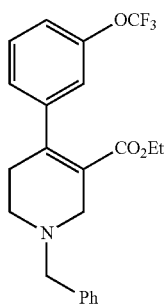

Compound 3jj was prepared using the method of Example 19 or Example 20, described above in 99% yield from 2 and 3-Trifluoromethoxyphenyl boronic acid. ¹H NMR (300 MHz, CDCl₃) δ 7.40-7.26 (comp., 6H), 7.16-7.05 (comp., 2H), 7.02 (br. s., 1H), 3.87 (q, J=7.2 Hz, 2H), 3.69 (s, 2H), 3.39 (t, J=2.5 Hz, 2H), 2.65 (t, J=5.8 Hz, 2H), 2.50 (dq, J=5.5, 2.8 Hz, 2H), 0.84 (t, J=7.2 Hz, 3H).

Example 51

Synthesis of Ethyl 1-benzyl-1,2,5,6-tetrahydro-[4,4'-bipyridine]-3-carboxylate (Compound 3kk)

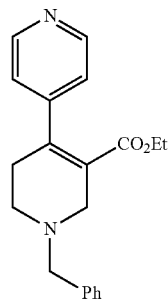 [SMILES: CCOC(=O)C1=C(c2ccncc2)CCN(Cc2ccccc2)C1]

Compound 3kk was prepared in 99% yield using the method of Example 19 or Example 20, described above from 2 and 4-Pyridinylboronic acid. ¹H NMR (300 MHz, CDCl₃) δ 8.57-8.51 (m, 2H), 7.40-7.27 (m, 5H), 7.09-7.03 (m, 2H), 3.90 (q, J=7.2 Hz, 2H), 3.69 (s, 2H), 3.39 (t, J=2.7 Hz, 2H), 2.66 (t, J=5.8 Hz, 2H), 2.47 (septet J=2.7 Hz, 2H), 0.88 (t, J=7.2 Hz, 3H).

Example 52

Synthesis of Ethyl 1'-benzyl-1',2',5',6'-tetrahydro-[3,4'-bipyridine]-3'-carboxylate (Compound 3ll)

Compound 3ll was prepared in 88% yield using the method of Example 19 or Example 20, described above from 2 and 3-Pyridinylboronic acid. ¹H NMR (300 MHz, CDCl₃) δ 8.51 (dd, J=1.6, 4.7 Hz, 1H), 8.39 (d, J=1.4 Hz, 1H), 7.47 (dt, J=1.9, 7.8 Hz, 1H), 7.41-7.21 (m, 6H), 3.90 (q, J=7.2 Hz, 2H), 3.70 (s, 2H), 3.41 (t, J=2.7 Hz, 2H), 2.66 (t, J=5.8 Hz, 2H), 2.56-2.44 (m, 2H), 0.88 (t, J=7.2 Hz, 3H).

Example 53

Synthesis of Ethyl 1-benzyl-4-(3,4-dichlorophenyl)-1,2,5,6-tetrahydropyridine-3-carboxylate (Compound 3nn)

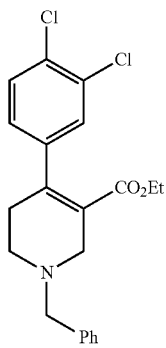

Compound 3nn was prepared using the method of Example 19 or Example 20, described above in 99% yield from 2 and 3,4-dichlorophenylboronic acid. $^1$H NMR (300 MHz, CDCl$_3$) δ 7.26-7.41 (m, 6H), 7.24 (d, J=1.9 Hz, 1H), 6.98 (dd, J=8.3, 2.2 Hz, 1H), 3.94 (q, J=7.1 Hz, 2H), 3.68 (s, 2H), 3.37 (t, J=2.8 Hz, 2H), 2.60-2.66 (m, 2H), 2.42-2.49 (m, 2H), 0.95 (t, J=7.0 Hz, 3H).

Example 54

Synthesis of Ethyl 1-benzyl-4-(3-((tert-butoxycarbonyl)amino)phenyl)-1,2,5,6-tetrahydropyridine-3-carboxylate (Compound 3qq)

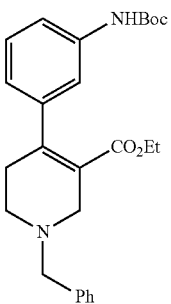 [SMILES: CCOC(=O)C1=C(c2cccc(NC(=O)OC(C)(C)C)c2)CCN(Cc2ccccc2)C1]

Compound 3qq was prepared using the method of Example 19 or Example 20, described above in 96% yield from 2 and 3-(N-Boc-amino)phenylboronic acid. $^1$H NMR (300 MHz, CDCl$_3$) δ 7.42-7.26 (m, 5H), 7.23-7.16 (m, 3H), 6.81 (dt, J=2.55, 5.37 Hz, 1H), 6.42 (s, 1H), 4.11 (q, J=7.06 Hz, 0.5H), 3.90 (q, J=7.15 Hz, 2H), 3.67 (s, 2H), 3.38-3.32 (m, 2H), 2.67-2.57 (m, 2H), 2.50 (dq, J=2.83, 5.54 Hz, 2H), 1.50 (s, 9H), 1.25 (t, J=7.15 Hz, 1H), 0.89 (t, J=7.15 Hz, 3H). (Exists as rotomers; seen especially in the ester).

Example 55

Synthesis of Ethyl 1-benzyl-4-(3,4-difluorophenyl)-1,2,5,6-tetrahydropyridine-3-carboxylate (Compound 3ss)

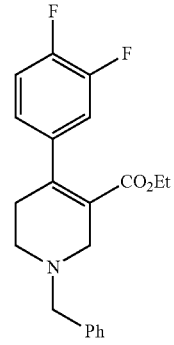 [SMILES: CCOC(=O)C1=C(c2ccc(F)c(F)c2)CCN(Cc2ccccc2)C1]

Compound 3ss was prepared using the method of Example 19 or Example 20, described above in 89% yield from 2 and 3,4-difluorophenylboronic acid. $^1$H NMR (300 MHz, CDCl$_3$) δ 7.43-7.25 (m, 5H), 7.09 (dt, J=8.36, 10.25 Hz, 1H), 7.02-6.90 (m, 1H), 6.89-6.80 (m, 1H), 3.93 (q, J=7.15 Hz, 2H), 3.68 (s, 2H), 3.36 (t, J=2.75 Hz, 2H), 2.64 (t, J=5.64 Hz, 2H), 2.46 (tt, J=2.75, 5.64 Hz, 2H), 0.95 (t, J=7.15 Hz, 3H).

Example 56

Synthesis of Ethyl 1-benzyl-4-(3,4-difluorophenyl)-1,2,5,6-tetrahydropyridine-3-carboxylate (Compound 3tt)

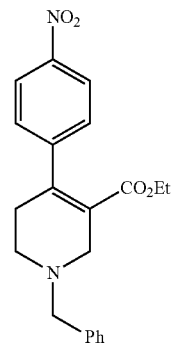 [SMILES: CCOC(=O)C1=C(c2ccc([N+](=O)[O-])cc2)CCN(Cc2ccccc2)C1]

Compound 3tt was prepared using the method of Example 19 or Example 20, described above in 89% yield from 2 and 4-nitrophenylboronic acid. $^1$H NMR (300 MHz, CDCl$_3$) δ 7.43-7.26 (m, 5H), 7.23 (d, J=7.43 Hz, 1H), 7.14-6.96 (m, 3H), 3.90 (q, J=7.15 Hz, 2H), 3.70 (s, 2H), 3.42 (t, J=2.75 Hz, 2H), 2.71-2.59 (m, 2H), 2.55-2.43 (m, 2H), 0.88 (t, J=7.15 Hz, 3H).

Example 57

Synthesis of 1-benzyl-4-(4-fluorophenyl)-1,2,3,6-tetrahydropyridine (Compound 14)

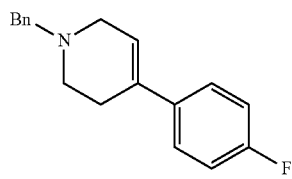 [SMILES: Fc1ccc(C2=CCN(Cc3ccccc3)CC2)cc1]

Compound 14 was prepared from 13 and 4-fluorophenyl boronic acid as a yellow oil (1.00 g, 76%) using the method of Example 19 or Example 20, described above: $R_f$=0.48 (20% EtOAc/Hexanes); $^1$H NMR (300 MHz, CDCl$_3$) δ 7.19-7.52 (m, 7H), 6.99 (t, J=8.8 Hz, 2H), 5.95-6.08 (m, 1H), 3.64 (s, 2H), 3.16 (q, J=2.8 Hz, 2H), 2.71 (t, J=5.8 Hz, 2H), 2.44-2.61 (m, 2H).

Example 58

General Procedure used in Reduction and Debenzylation of Compounds

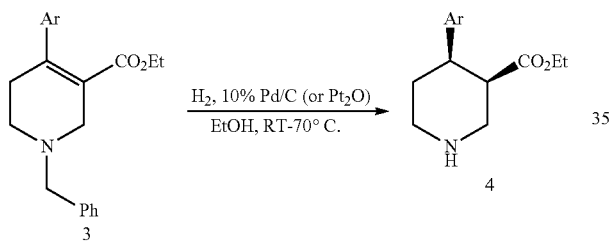

To a 50 mL round bottom flask was added 10% Pd/C (225 mg, 0.10 mmol, 50% wet) followed by the addition of a solution of 3 (350 mg, 1 mmol) in EtOH (10 mL). The flask was evacuated and back-flushed with H$_2$ three times, and the reaction mixture was stirred under a static atmosphere of H$_2$ at room temperature (unless otherwise noted) for 24-72 hrs. The suspension was filtered through a pad of celite, washing with EtOH. The combined filtrate and washings were concentrated and purified by flash chromatography eluting with 0-10% MeOH/EtOAc (1% Et$_3$N) to give pure 4.

Example 59

Synthesis of (±) syn-ethyl 4-phenylpiperidine-3-carboxylate (Compound 4a)

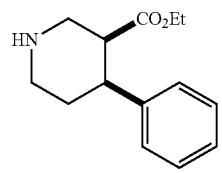

Compound 4a was prepared from 3a in 73% yield using the method of Example 58 above. $^1$H NMR (300 MHz, CDCl$_3$) δ 7.31-7.17 (comb, 5H), 3.86 (q, J=7.2 Hz, 2H), 3.37-3.27 (comp, 2H), 3.16-2.95 (comp, 2H), 2.78-2.68 (comp, 2H), 2.36 (dq, J=4.5, 12.6 Hz, 1H), 1.67 (dd, J=3.0, 12.9 Hz, 1H), 0.92 (t, J=7.2 Hz, 3H).

Example 60

Synthesis of (±) syn-ethyl 4-(p-tolyl)piperidine-3-carboxylate (Compound 4b)

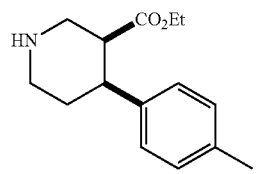

Compound 4b was prepared from 3b in 68% yield using the method of Example 58 above. $^1$H NMR (300 MHz, CDCl$_3$) δ 7.11-7.03 (comp, 4H), 3.87 (q, J=7.2 Hz, 2H), 3.35-3.27 (comp, 2H), 3.02-2.91 (comp, 2H), 2.76-2.68 (comp, 2H), 2.40-2.19 (comp, 4H), 1.67-1.58 (m, 1H), 0.94 (t, J=7.2 Hz, 3H).

Example 61

Synthesis of (±) syn-ethyl 4-(2,3-dihydrobenzo[b][1,4]dioxin-5-yl)piperidine-3-carboxylate

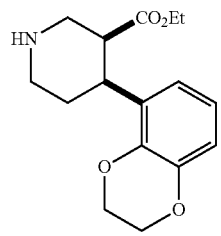

Compound 4c was prepared from 3c in 25% yield using the method of Example 58 above. $^1$H NMR (300 MHz, CDCl$_3$) δ 6.77 (d, J=8.1 Hz, 1H), 6.69 (d, J=2.1 Hz, 1H), 6.66 (dd, J=2.1, 7.8 Hz, 1H), 4.22 (s, 4H), 4.00-3.85 (m, 2H), 3.33-3.26 (comp, 2H), 2.96-2.87 (comp, 2H), 2.74-2.65 (comp, 2H), 2.25 (dq, J=4.2, 12.6 Hz, 1H), 1.61 (dd, J=3.0, 13.2 Hz, 1H), 1.00 (t, J=7.2 Hz, 3H).

Example 62

Synthesis of (±) syn-ethyl 4-(4-fluorophenyl)piperidine-3-carboxylate (Compound 4d)

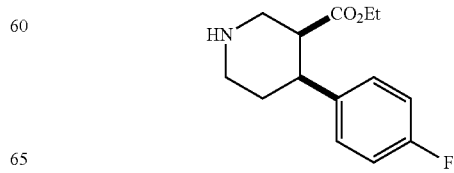

Compound 4d was prepared from 3d as a yellow oil (751 mg, 58%) using the method of Example 58 above. $R_f$=0.21 (10% MeOH/CH$_2$Cl$_2$); $^1$H NMR (300 MHz, CDCl$_3$) δ 7.14 (dd, J=5.5, 8.8 Hz, 2H), 6.96 (t, J=8.8 Hz, 2H), 3.87 (q, J=7.2 Hz, 2H), 3.24-3.40 (m, 2H), 2.88-3.05 (m, 2H), 2.63-2.79 (m, 2H), 2.30 (qd, J=4.4, 12.9 Hz, 1H), 1.64 (dq, J=2.8, 12.9 Hz, 1H), 0.94 (t, J=7.2 Hz, 3H).

Example 63

Synthesis of (±) syn-ethyl 4-(3-fluorophenyl)piperidine-3-carboxylate (Compound 4e)

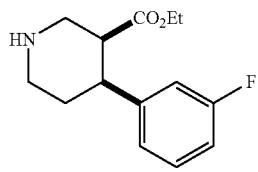

Compound 4e was prepared from 3e as a yellow oil (247 mg, 67%) using the method of Example 58 above. $R_f$=0.05 (10% MeOH/CH$_2$Cl$_2$); $^1$H NMR (300 MHz, CDCl$_3$) δ 7.28-7.21 (m, 1H), 6.97 (d, J=7.8 Hz, 1H), 6.93-6.86 (m, 2H), 3.89 (dq, J=1.8, 6.9 Hz, 2H), 3.38-3.28 (comp, 2H), 3.61-2.93 (comp, 2H), 2.77-2.68 (comp, 2H), 2.30 (dq, J=4.5, 12.9 Hz, 1H), 1.67 (dq, J=2.7, 13.2 Hz, 1H).

Example 64

Synthesis of (±) syn-ethyl 4-(4-(trifluoromethyl)phenyl)piperidine-3-carboxylate (Compound 4f)

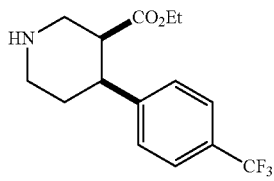

Compound 4f was prepared from 3f in 92% yield using the method of Example 58 above. $^1$H NMR (300 MHz, CDCl$_3$) δ 7.54 (d, J=7.8 Hz, 2H), 7.32 (d, J=7.8 Hz, 2H), 3.87 (q, J=7.2 Hz, 2H), 3.40-3.30 (comp, 2H), 3.22-3.04 (m, 1H), 2.98 (dd, J=3.9, 13.8 Hz, 1H), 2.79-2.70 (comp, 2H), 2.36 (dq, J=4.2, 12.6 Hz, 1H), 1.84-1.75 (m, 1H), 0.92 (t, J=7.2 Hz, 3H).

Example 65

Synthesis of (±) syn-ethyl 4-(3-(trifluoromethyl)phenyl)piperidine-3-carboxylate (Compound 4g)

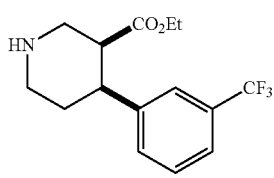

Compound 4g was prepared from 3g in 74% yield using the method of Example 58 above. $^1$H NMR (300 MHz, CDCl$_3$) δ 7.49-7.38 (comp, 4H), 3.86 (q, J=6.9 Hz, 2H), 3.40-3.30 (comp, 2H), 3.08 (dt, J=3.6, 12.9 Hz, 1H), 2.98 (dd, J=3.6, 13.8 Hz, 1H), 2.80-2.69 (comp, 2H), 2.34 (dq, J=3.9, 12.9 Hz, 1H), 1.68 (dd, J=3.0, 13.2 Hz, 1H), 0.91 (t, J=6.9 Hz, 3H).

Example 66

Synthesis of (±) syn-ethyl 4-(4-(dimethylamino)phenyl)piperidine-3-carboxylate (Compound 4h)

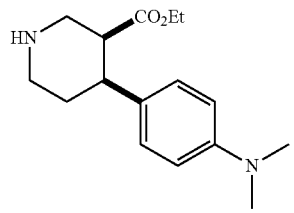

Compound 4h was prepared from 3h in 50% yield using the method of Example 58 above. $^1$H NMR (300 MHz, CDCl$_3$) δ 7.05 (d, J=8.7 Hz, 2H), 6.68 (d, J=8.7 Hz, 2H), 3.90 (q, J=6.9 Hz, 2H), 3.33-3.29 (comp, 2H), 2.96-2.82 (comp, 8H), 2.72-2.67 (comp, 2H), 2.30 (dq, J=4.2, 13.2 Hz, 1H), 1.64 (dd, J=2.7, 13.2 Hz, 1H), 0.98 (t, J=6.9 Hz, 3H).

Example 67

Synthesis of (±) syn-ethyl 4-(4-carbamoylphenyl)piperidine-3-carboxylate (Compound 4i)

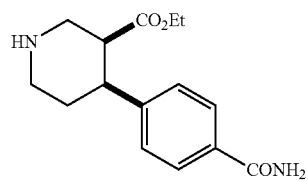

Compound 4i was prepared from 3i as a white solid (193 mg, 68%) using the method of Example 58 above except stirring at 45° C.: $R_f$=0.10 (10% MeOH/CH$_2$Cl$_2$); $^1$H NMR (300 MHz, CDCl$_3$) δ 7.73 (d, J=8.1 Hz, 2H), 7.23 (d, J=8.1 Hz, 2H), 6.05 (br. s, 1H), 5.53 (br. s, 1H), 3.91-3.75 (m, 2H), 3.36-3.26 (comp, 2H), 3.07 (dt, J=4.2, 12.6 Hz, 1H), 2.95 (dd, J=3.9, 14.1 Hz, 1H), 2.81-2.67 (comp, 2H), 2.32 (dq, J=4.2, 12.9 Hz, 1H), 1.70 (dq, J=2.7, 13.2 Hz, 1H), 0.89 (t, J=7.2 Hz, 3H).

Example 68

Synthesis of (±) syn-ethyl 4-([1,1'-biphenyl]-4-yl)piperidine-3-carboxylate (Compound 4j)

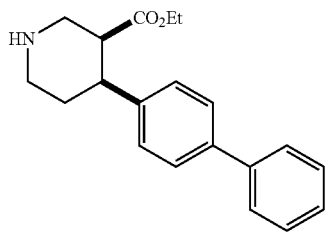

Compound 4j was prepared from 3j in 70% yield using the method of Example 58 above. $^1$H NMR (300 MHz, CDCl$_3$) δ 7.59-7.50 (comp, 4H), 7.54-7.39 (m, 2H), 7.36-7.24 (comp, 3H), 3.89 (q, J=7.2 Hz, 2H), 3.39-3.31 (comp, 2H), 3.11-2.96 (comp, 2H), 2.82-2.71 (comp, 2H), 2.38 (dq, J=3.9, 12.9 Hz, 1H), 2.25 (br. s, 1H), 1.74-1.67 (m, 1H), 0.92 (t, J=7.2 Hz, 3H).

Example 69

Synthesis of (±) syn-ethyl 4-(1-(tert-butoxycarbonyl)-1H-pyrrol-2-yl)piperidine-3-carboxylate (Compound 4k)

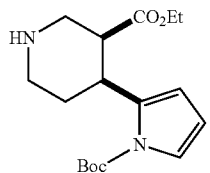

Compound 4k was prepared from 3k as a colorless oil (166 mg, 38%) using the method of Example 58 above. R$_f$=0.25 (10% MeOH/CH$_2$Cl$_2$); $^1$H NMR (300 MHz, CDCl$_3$) δ 7.19 (dd, J=1.8, 3.3 Hz, 1H), 6.04 (t, J=3.3 Hz, 1H), 5.95-5.92 (m, 1H), 3.88-3.79 (m, 2H), 3.72 (dt, J=1.8, 12.9 Hz, 1H), 3.30-3.22 (m, 2H), 3.06-3.02 (m, 1H), 2.91 (dd, J=3.6, 14.1 Hz, 1H), 2.76-2.68 (m, 1H), 2.09 (dq, J=3.9, 12.6 Hz, 1H), 1.72-1.64 (m, 1H), 1.58 (s, 9H), 0.98 (t, J=7.2 Hz, 3H).

Example 70

Synthesis of (±) syn-ethyl 4-(4-(ethoxycarbonyl)phenyl)piperidine-3-carboxylate (Compound 4l)

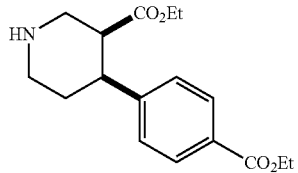

Compound 4l was prepared from 3l in 51% yield using the method of Example 58 above. $^1$H NMR (300 MHz, CDCl$_3$) δ 7.96 (d, J=8.7 Hz, 2H), 7.26 (d, J=8.7 Hz, 2H), 3.35 (q, J=7.2 Hz, 2H), 3.95-3.79 (m, 2H), 3.39-3.29 (comp, 2H), 3.11-2.95 (comp, 2H), 2.81-2.69 (comp, 2H), 2.36 (dq, J=3.9, 12.6 Hz, 1H), 1.68 (dd, J=2.7, 13.2 Hz, 1H), 1.37 (t, J=7.2 Hz, 3H), 0.94 (t, J=7.2 Hz, 3H).

Example 71

Synthesis of (±) syn-ethyl 4-(thiophen-2-yl)piperidine-3-carboxylate (Compound 4m)

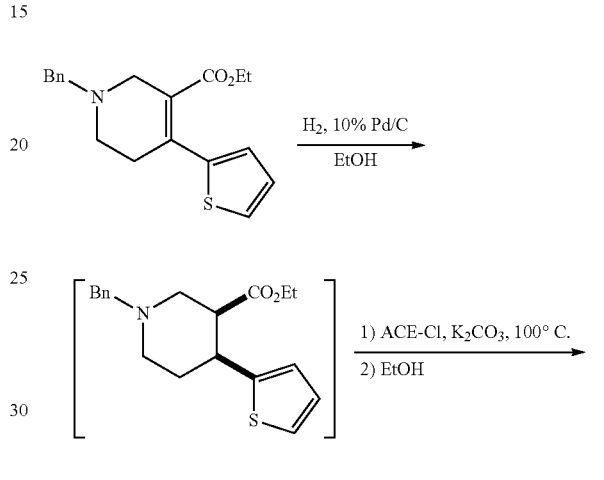

The olefin was reduced according to the method of Example 58 above and was prepared from 3m as a yellow oil (342 mg, 45%). R$_f$=0.22 (25% EtOAc/hexanes); $^1$H NMR (300 MHz, CDCl$_3$) δ 7.32-7.24 (comp, 5H), 7.13 (dd, J=1.5, 4.8 Hz, 1H), 6.93-6.87 (comp, 2H), 4.05-3.95 (m, 2H), 3.55 (dd, J=13.5, 55.8 Hz, 2H), 3.36 (br. s, 1H), 3.02-2.97 (m, 2H), 2.84 (br. s, 1H), 2.58-2.35 (comp, 3H), 2.04-1.97 (m, 1H), 1.07 (t, J=7.2 Hz, 3H).

Debenzylation was performed according to the following procedure: A round bottom flask was charged with 4a (342 mg, 1.04 mmol), then α-chloroethyl chloroformate (ACE-Cl, 1.05 mL, 14.1 mmol) was added under nitrogen by syringe in one portion, and the reaction mixture stirred for 2.5 h at 100° C. Volatiles were removed in vacuo and the residue was treated with anhydrous EtOH (20 mL). The flask was then heated to reflux for 20 min and concentrated in vacuo. The solid residue was purified by flash chromatography using 0-10% MeOH/CH$_2$Cl$_2$ (1% Et$_3$N) to give 4m (219 mg, 87%) as a yellow oil: R$_f$=0.18 (10% MeOH/CH$_2$Cl$_2$, 1% Et$_3$N); $^1$H NMR (300 MHz, CDCl$_3$) δ 7.14 (dd, J=1.2, 5.1 Hz, 1H), 6.91 (dd, J=3.6, 5.1 Hz, 1H), 6.82 (d, J=3.6 Hz, 1H), 3.96 (q, J=6.9 Hz, 2H), 3.39-3.21 (comp, 3H), 2.97 (dd, J=3.9, 13.8 Hz, 1H), 2.85 (dd, J=3.6, 7.8 Hz, 1H), 2.74 (ddd, J=3.3, 11.4, 16.8 Hz, 1H), 2.35-2.21 (m, 1H), 1.88-1.81 (m, 1H), 1.04 (t, J=6.9 Hz, 3H).

Example 72

Synthesis of (±) syn-ethyl 4-(5-methylthiophen-2-yl)piperidine-3-carboxylate (Compound 4n)

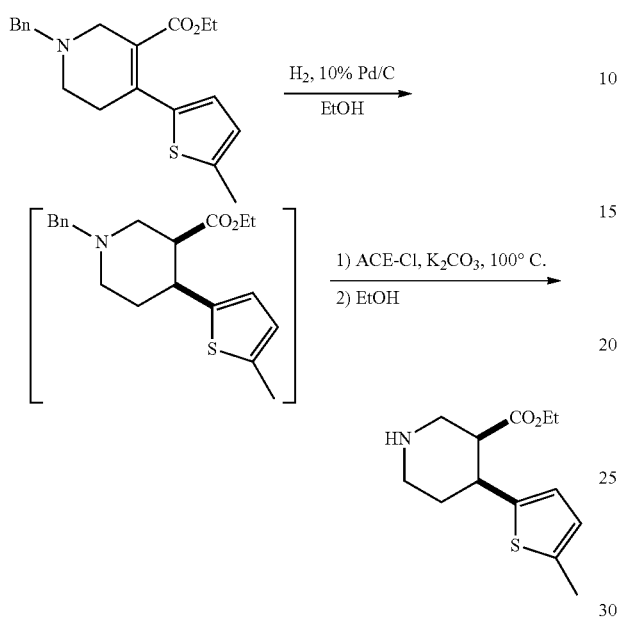

The olefin was reduced according to the method of Example 52 above and prepared as a colorless oil (501 mg, 47%). $^1$H NMR (300 MHz, CDCl$_3$) δ 7.33-7.22 (comp, 5H), 6.63 (d, J=3.6 Hz, 1H), 6.54-6.52 (m, 1H), 4.07-3.95 (m, 2H), 3.53 (dd, J=13.5, 56.4 Hz, 2H), 3.29 (br. s, 1H), 2.97-2.92 (m, 2H), 2.81 (br. s, 1H), 2.54 (br. s, 1H), 2.43-2.34 (comp, 5H), 1.99-1.93 (m, 1H), 1.10 (t, J=7.2 Hz, 3H).

Compound 4n was prepared as a yellow oil (400 mg, 100%) using the procedure described in Example 71 above. R$_f$=0.22 (10% MeOH/CH$_2$Cl$_2$); $^1$H NMR (300 MHz, CDCl$_3$) δ 6.60 (d, J=3.6 Hz, 1H), 6.55 (dd, J=1.2, 3.3 Hz, 1H), 4.11-4.05 (m, 2H), 3.69 (dd, J=5.1, 10.5 Hz, 1H), 3.41 (d, J=6.0 Hz, 2H), 3.38-3.16 (comp, 3H), 2.42 (s, 3H), 2.32-2.19 (m, 2H), 1.11 (t, J=7.2 Hz, 3H).

Example 73

Synthesis of (±) syn-ethyl 4-(4-(1-hydroxyethyl)phenyl)piperidine-3-carboxylate (Compound 4p)

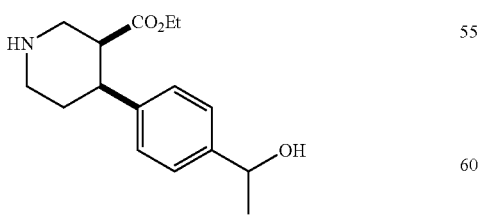

Compound 4p was prepared from 3p in 41% yield using the method of Example 58 above. $^1$H NMR (300 MHz, CDCl$_3$) δ 7.29 (d, J=8.1 Hz, 2H), 7.19 (d, J=8.1 Hz, 2H), 4.87 (q, J=6.3 Hz, 1H), 3.88 (q, J=6.9 Hz, 2H), 3.36-3.28 (comp, 2H), 3.16-2.93 (comp, 2H), 2.77-2.67 (comp, 2H), 2.34 (dq, J=4.2, 12.9 Hz, 1H), 1.70-1.63 (m, 1H), 1.46 (d, J=6.3 Hz, 3H), 0.93 (t, J=6.9 Hz, 3H).

Example 74

Synthesis of (±) syn-Ethyl 4-(3-methoxyphenyl)piperidine-3-carboxylate (Compound 4q)

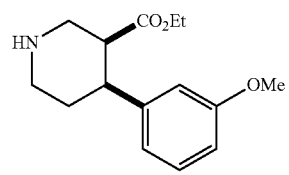

Compound 4q was prepared from 3q as a light yellow oil (839 mg, 100%) using the method of Example 58 above. $^1$H NMR (300 MHz, CDCl$_3$) δ 7.23-7.18 (m, 1H), 6.79-6.72 (m, 3H), 3.89 (q, J=7.2 Hz, 2H), 3.78 (s, 3H), 3.48 (br. s, 1H), 3.39-3.33 (m, 2H), 3.07-2.98 (m, 2H), 2.84-2.75 (m, 2H), 2.33 (dq, J=12.9, 4.2 Hz, 1H), 1.71 (dd, J=13.2, 2.4 Hz, 1H), 0.94 (t, J=7.2 Hz, 3H).

Example 75

Synthesis of (±) syn-Ethyl 4-(4-methoxyphenyl)piperidine-3-carboxylate (Compound 4r)

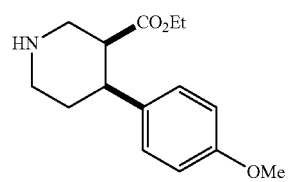

Compound 4r was prepared from 3r as a yellow waxy solid (361 mg, 96%) using the method of Example 58 above. R$_f$=0.07 (10% MeOH/CH$_2$Cl$_2$); $^1$H NMR (300 MHz, CDCl$_3$) δ 7.10 (d, J=8.7 Hz, 2H), 6.82 (d, J=8.7 Hz, 2H), 3.87 (q, J=7.2 Hz, 2H), 3.78 (s, 3H), 3.35-3.27 (m, 2H), 3.01-2.92 (m, 2H), 2.77-2.66 (m, 2H), 2.30 (dq, J=12.9, 4.5 Hz, 1H), 1.63 (dd, J=13.2, 2.4 Hz, 1H), 0.94 (t, J=7.2 Hz, 3H).

Example 76

Synthesis of (±) syn-Ethyl 4-(3-((tert-butoxycarbonyl)amino)phenyl)piperidine-3-carboxylate (Compound 4s)

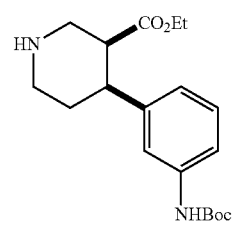

Compound 4s was prepared from 3s as an off-white solid (307 mg, 60%) using the method of Example 58 above. mp=154.5-156.5° C.; R$_f$=0.05 (10% MeOH/CH$_2$Cl$_2$); $^1$H NMR (300 MHz, CDCl$_3$) δ 7.28-7.16 (m, 3H), 6.86 (m, 1H), 6.45 (br. s, 1H), 3.90 (q, J=7.2 Hz, 2H), 3.35-3.27 (m, 2H), 3.02-2.92 (m, 2H), 2.79-2.67 (m, 2H), 2.32 (dq, J=12.6, 4.5 Hz, 1H), 1.92 (br. s, 1H), 1.63 (d, J=12.6 Hz, 1H), 1.51 (s, 9H), 0.97 (t, J=7.2 Hz, 3H).

Example 77

Synthesis of (±)-syn-Ethyl 4-(ethyl)piperidine-3-carboxylate (Compound 4t)

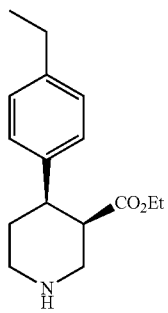 [SMILES: CCOC(=O)[C@H]1CNCC[C@H]1c1ccc(CC)cc1]

Compound 4t was prepared according to the method of Example 58 above from 3t in 95% yield using 10% Pd/C at 1 atm of H$_2$ for 18 hours. $^1$H NMR (300 MHz, CDCl$_3$) δ 7.19-7.00 (comp., 4H), 3.87 (qt, J=1.10, 6.88 Hz, 2H), 3.41-3.26 (m, 2H), 3.07-2.92 (m, 2H), 2.82-2.69 (m, 2H), 2.61 (q, J=7.71 Hz, 2H), 2.52-2.41 (m, 1H), 2.40-2.23 (m, 1H), 1.72-1.62 (m, 1H), 1.20 (t, J=7.57 Hz, 3H), 0.92 (t, J=7.15 Hz, 3H).

Example 78

Synthesis of (±)-syn-Ethyl 4-(isopropyl)piperidine-3-carboxylate (Compound 4u)

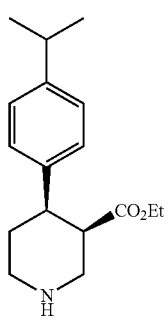 [SMILES: CCOC(=O)[C@H]1CNCC[C@H]1c1ccc(C(C)C)cc1]

Compound 4u was prepared according to the method of Example 58 above from 3u in 95% yield using 10% Pd/C at 1 atm of H$_2$ for 18 hours. $^1$H NMR (300 MHz, CDCl$_3$) δ 7.15 (d, J=8.26 Hz, 2H), 7.10 (d, J=8.53 Hz, 2H), 3.98-3.75 (m, 2H), 3.40-3.21 (m, 2H), 3.06-2.67 (m, 5H), 2.32 (qd, J=4.27, 12.80 Hz, 1H), 1.70 (dq, J=2.20, 13.76 Hz, 1H), 1.22 (d, J=6.88 Hz, 6H), 0.88 (t, J=7.15 Hz, 3H).

Example 79

Synthesis of (±)-syn-Ethyl 4-phenethylpiperidine-3-carboxylate (Compound 4v)

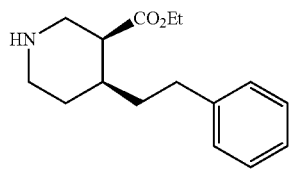 [SMILES: CCOC(=O)[C@@H]1CNCC[C@@H]1CCc1ccccc1]

Compound 4v was prepared according to the method of Example 58 above and isolated as a yellow oil from 3v in 39% yield using 10% Pd/C at 1 atm of H$_2$ and 45° C. for 18 hours. $^1$H NMR (300 MHz, CDCl$_3$) δ 7.33-7.26 (m, 2H), 7.22-7.10 (m, 3H), 4.25-4.06 (m, 2H), 3.25 (dd, 4H), 3.14 (dt, J=3.61, 13.42 Hz, 1H), 2.84 (dd, J=3.71, 13.62 Hz, 1H), 2.73-2.57 (m, 6H), 1.91-1.70 (m, 1H), 1.70-1.50 (m, 4H), 1.27 (t, J=7.15 Hz, 3H).

Example 80

Synthesis of (±)-syn-Ethyl 4-(3-fluorophenyl)piperidine-3-carboxylate (Compound 4x)

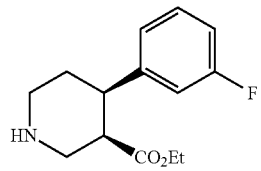 [SMILES: CCOC(=O)[C@H]1CNCC[C@H]1c1cccc(F)c1]

Compound 4x was isolated as a yellow oil in 42% yield from 3x according to method of Example 58 above. $^1$H NMR (300 MHz, CDCl$_3$) δ 7.24-7.13 (m, 2H), 7.10-6.95 (m, 2H), 3.85 (q, J=7.15 Hz, 2H), 3.42-3.27 (m, 3H), 2.99 (dd, J=3.71, 13.90 Hz, 1H), 2.88 (t, J=4.27 Hz, 1H), 2.78 (ddd, J=2.89, 12.18, 13.55 Hz, 1H), 2.34 (qd, J=4.27, 12.80 Hz, 1H), 1.59 (dq, J=3.11, 12.97 Hz, 1H), 0.90 (t, J=7.15 Hz, 3H).

Example 81

Synthesis of (±)-syn-Ethyl 4-(m-tolyl)piperidine-3-carboxylate (Compound 4y)

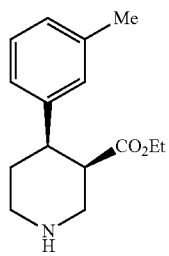 [SMILES: CCOC(=O)[C@H]1CNCC[C@H]1c1cccc(C)c1]

Compound 4y was prepared according to the method of Example 58 from 3y in 95% yield using 10% Pd/C at 1 atm of $H_2$ for 18 hours. $^1$H NMR (300 MHz, CDCl$_3$) δ 7.16 (t, J=8.0, 1H), 7.03-6.92 (m, 3H), 4.93 (br. s., 1H), 3.88 (q, J=7.0 Hz, 2H), 3.44-3.31 (m, 2H), 3.13-3.01 m, 2H), 2.91-2.79 (m, 2H), 2.43-2.31 (m, 1H), 2.30 (s, 3H), 1.83-1.70 (m, 1H), 0.92 (t, J=7.2 Hz, 3H).

Example 82

Synthesis of (±)-syn-Ethyl 4-(o-tolyl)piperidine-3-carboxylate (Compound 4z)

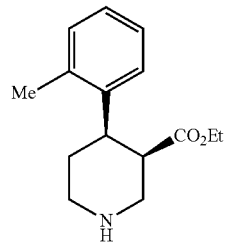 [SMILES: CCOC(=O)[C@H]1CNCC[C@H]1c1ccccc1C]

Compound 4z was prepared according to the method of Example 58 from 3z in 37% yield using Pt$_2$O at 3 atm of $H_2$ for 5 days. $^1$H NMR (300 MHz, CDCl$_3$) δ 7.22-7.09 (m, 3H), 7.04-6.98 (m, 1H), 4.01-3.83 (m, 2H), 3.78-3.65 (m, 2H), 3.54-3.42 (m, 2H), 3.28 (td, J=12.3, 3.2 Hz, 1H), 3.14 (q, J=3.8 Hz, 1H), 2.58 (tq, J=3.9, 2.8 Hz, 1H), 2.37 (s, 3H), 2.02 (dd, J=14.4, 3.2 Hz, 1H), 0.89 (t, J=7.2 Hz, 3H).

Example 83

Synthesis of (±)-syn-Ethyl 4-(3-(dimethylamino)phenyl)piperidine-3-carboxylate (Compound 4aa)

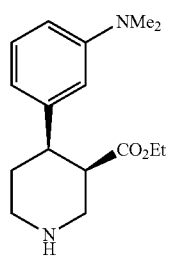

Compound 4aa was prepared according to the method of Example 58 above from 3aa in 33% yield using Pt$_2$O at 1 atm of $H_2$ for 4 days. $^1$H NMR (300 MHz, CDCl$_3$) δ 7.15 (t, J=8.1 Hz, 1H), 6.66-6.58 (m, 1H), 6.52-6.44 (m, 2H), 3.99 (m, 2H), 3.62 (dt, J=4.4, 3.6 Hz, 2H), 3.44 (dd, J=13.5, 3.3 Hz, 1H), 3.35 (s, 6H), 2.40-2.57 (m, 1H), 2.08-2.21 (m, 1H), 0.98 (t, J=7.2 Hz, 3H).

Example 84

Synthesis of (±)-syn-Ethyl 4-(2-(dimethylamino)phenyl)piperidine-3-carboxylate (Compound 4bb)

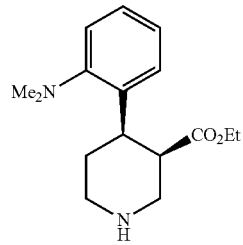 [SMILES: CCOC(=O)[C@H]1CNCC[C@H]1c1ccccc1N(C)C]

Compound 4bb was prepared according to the method of Example 58 above from 3bb in 78% yield using 10% Pd/C at 3 atm of $H_2$ for 2 days. $^1$H NMR (300 MHz, CDCl$_3$) δ 7.25-7.11 (m, 2H), 7.11-6.90 (m, 2H), 3.96-3.75 (m, 2H), 3.75-3.62 (m, 2H), 3.58 (d, J=13.2 Hz, 1H), 3.44-3.21 (m, 2H), 3.13 (td, J=12.7, 2.8 Hz, 1H), 2.61 (s, 6H), 2.46 (dd, J=13.5, 3.3 Hz, 1H), 1.84 (dd, J=14.2, 2.9 Hz, 1H), 0.82 (t, J=7.2 Hz, 3H).

Example 85

Synthesis of Ethyl 4-(3,4-dichlorophenyl)piperidine-3-carboxylate (Compound 4cc)

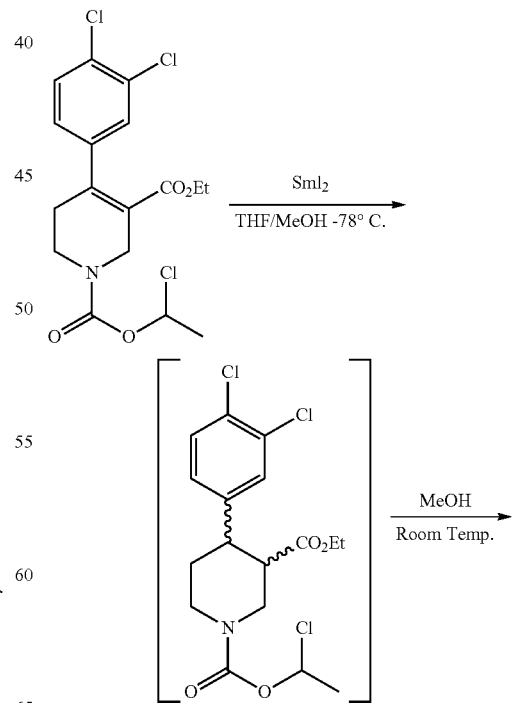

-continued

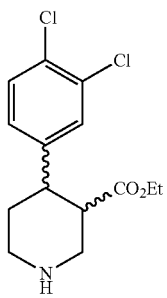

A dry 50-mL round bottom flask was charged with SM (200 mg, 0.49 mmol) and dry THF (5 mL). The solution was cooled to −78° C. MeOH (1 mL) was then added to the chilled solution immediately followed by SmI2 (19.6 mL, 1.97 mmol, 0.1 M in THF). The reaction mixture turned blue and was stirred for 1.5 hours. The mixture was quenched by the addition of water (10 mL) and warmed to room temperature at which time the reaction mixture turned yellow. The mixture was diluted with EtOAc and washed with saturated NaHCO$_3$ solution. The aqueous layer was further extracted with EtOAc. The combined extracts were then washed with brine, dried over Na$_2$SO$_4$, concentrated and purified via silica gel chromatography (10-100% EtOAc/Hexanes). The reduced intermediate was obtained as a pale yellow oil (140 mg) in 70% yield. $^1$H NMR (300 MHz, CDCl$_3$) δ ppm 7.38 (dd, J=14.6, 8.3 Hz, 1H), 7.29-7.21 (m, 1H), 7.05-6.92 (m, 1H), 6.68-6.51 (m, 1H), 4.42-4.25 (m, 1H), 3.96 (dq, J=18.1, 7.2 Hz, 2H), 3.70 (t, J=5.8 Hz, 3H), 2.93 (td, J=11.9, 4.0 Hz, 1H), 2.49 (br. s., 1H), 1.89-1.78 (m, 3H), 1.08-0.93 (m, 3H).

The product (a mixture of diasteromers) was dissolved in methanol (1 mL) and stirred overnight. The solvent was then removed under reduced pressure to afford the pure title compound in quantitative yield. $^1$H NMR (300 MHz, CDCl$_3$) δ ppm 7.47-7.35 (m, 2H), 7.33 (d, J=1.9 Hz, 1H), 7.12 (dd, J=8.5, 2.2 Hz, 1H), 7.04 (dd, J=8.3, 2.2 Hz, 1H), 4.02 (q, J=7.2 Hz, 2H), 3.92 (qd, J=7.1, 1.8 Hz, 1H), 3.83-3.56 (m, 3H), 3.51-3.12 (m, 4H), 3.10-2.89 (m, 2H), 2.58-2.24 (m, 1H), 2.19-1.92 (m, 1H), 0.99 (q, J=7.2 Hz, 6H).

Example 86

Synthesis of (±)-syn-ethyl 4-(3,4-dimethoxyphenyl)piperidine-3-carboxylate (Compound 4dd)

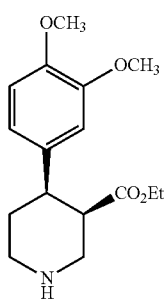

Compound 4dd was prepared according to the method of Example 58 above from 3dd in 30% yield using 10% Pd/C at 1 atm of H$_2$ for 5 days. $^1$H NMR (300 MHz, CDCl$_3$) δ 6.84-6.77 (m, 1H), 6.72-6.64 (m, 2H), 4.07-3.90 (m, 2H), 3.85 (s, 6H), 3.70-3.57 (m, 2H), 3.45 (dd, J=13.5, 3.6 Hz, 1H), 3.35-3.12 (m, 2H), 2.61-2.38 (m, 1H), 2.20-2.05 (m, 1H), 0.98 (t, J=7.2 Hz, 3H).

Example 87

Synthesis of (±)-syn-Ethyl 4-(3,4-dihydroxyphenyl)piperidine-3-carboxylate (Compound 4ff)

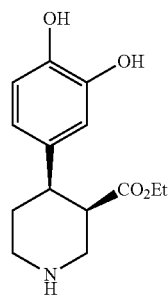 [SMILES: CCOC(=O)[C@H]1CNCC[C@H]1c1ccc(O)c(O)c1]

Compound 4ff was prepared according to the method of Example 58 above from 3ff in 86% yield using 10% Pd/C at 1 atm of H$_2$ for 20 hrs. $^1$H NMR (300 MHz, MeOD) δ 6.67 (d, J=8.3 Hz, 1H), 6.63 (d, J=2.2 Hz, 1H), 6.51 (dd, J=7.8, 2.1 Hz, 1H), 3.98-3.81 (m, 2H), 3.24 (s, 1H), 3.07-2.89 (m, 2H), 2.84-2.65 (m, 2H), 2.28 (dd, J=13.1, 4.0 Hz, 1H), 1.67 (dd, J=13.5, 3.0 Hz, 1H), 0.96 (t, J=7.2 Hz, 3H).

Example 88

Synthesis of (±)-syn-Ethyl 4-(2,3-dihydrobenzo[b][1,4]dioxin-6-yl)piperidine-3-carboxylate (Compound 4gg)

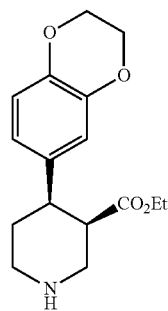 [SMILES: CCOC(=O)[C@H]1CNCC[C@H]1c1ccc2c(c1)OCCO2]

Compound 4gg was prepared according to the method of Example 58 above from 3gg using 10% Pd/C at 1 atm of H$_2$ for 20 hrs. $^1$H NMR (300 MHz, CDCl$_3$) δ 6.79 (d, J=8.3 Hz, 1H), 6.67-6.59 (m, 2H), 4.23 (s, 4H), 4.02 (q, J=6.9 Hz, 2H), 3.67-3.54 (m, 2H), 3.41 (dd, J=13.5, 3.6 Hz, 1H), 3.29-3.19 (m, 2H), 3.19-3.10 (m, 1H), 2.49-2.31-2.49 (m, 1H), 2.17-2.02 (m, 1H), 1.01 (t, J=7.2 Hz, 3H).

Example 89

Synthesis of (±)-syn-Ethyl 4-(2-(trifluoromethyl)phenyl)-1,2,5,6-tetrahydropyridine-3-carboxylate (Compound 4hh)

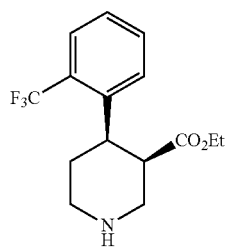 [SMILES: CCOC(=O)[C@H]1CNCC[C@H]1c1ccccc1C(F)(F)F]

Compound 4hh was prepared according to the method of Example 58 above from 3hh using 10% Pd/C at 1 atm of $H_2$ for 24 hrs. $^1$H NMR (300 MHz, CDCl$_3$) δ 7.66 (d, J=7.2 Hz, 1H), 7.55 (t, J=7.3 Hz, 1H), 7.44 (t, J=7.7 Hz, 1H), 7.25 (d, J=7.7 Hz, 1H), 4.13 (d, J=17.6 Hz, 1H), 3.88 (q, J=7.2 Hz, 3H), 3.64-3.52 (m, 1H), 3.17 (ddd, J=12.5, 10.5, 4.8 Hz, 1H), 2.60 (d, J=18.4 Hz, 1H), 0.82 (t, J=7.2 Hz, 3H).

Example 90

Synthesis of (±)-syn-Ethyl 4-(4-(trifluoromethoxy)phenyl)piperidine-3-carboxylate (Compound 4ii)

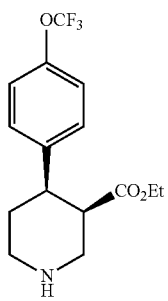

Compound 4ii was prepared according to the method of Example 58 above from 3ii in 97% yield using 10% Pd/C at 1 atm of $H_2$ for 24 hours. $^1$H NMR (300 MHz, CDCl3) δ 7.25-7.09 (m, 5H), 6.18 (br. s., 1H), 3.90 (q, J=7.2 Hz, 2H), 3.57-3.41 (m, 2H), 3.28-3.14 (m, 2H), 2.89-3.04 (m, 2H), 2.39 (m, 1H), 1.89 (dd, J=13.8, 3.0 Hz, 1H), 0.91 (t, J=7.2 Hz, 3H).

Example 91

Synthesis of (±)-syn-Ethyl 4-(3-(trifluoromethoxy)phenyl)piperidine-3-carboxylate (Compound 4jj)

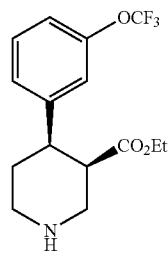 [SMILES: CCOC(=O)[C@H]1CNCC[C@H]1c1cccc(OC(F)(F)F)c1]

Compound 4jj was prepared according to the method of Example 58 above from 3jj in 74% yield using 10% Pd/C at 1 atm of $H_2$ for 24 hrs. $^1$H NMR (300 MHz, CDCl$_3$) δ 7.31 (t, J=7.7 Hz, 1H), 7.17-7.01 (m, 3H), 3.87 (q, J=7.2 Hz, 2H), 3.33 (t, J=13.8 Hz, 2H), 3.05 (dt, J=12.8, 4.3 Hz, 1H), 2.97 (dd, J=13.8, 3.6 Hz, 1H), 2.81-2.65 (m, 2H), 2.30 (qd, J=12.7, 4.3 Hz, 1H), 1.69 (dd, J=13.5, 2.8 Hz, 1H), 0.93 (t, J=7.2 Hz, 3H).

Example 92

Synthesis of (±)-syn-Ethyl 4-(pyridin-4-yl)piperidine-3-carboxylate (Compound 4kk)

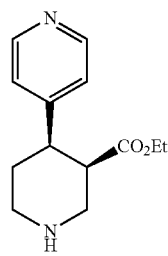 [SMILES: CCOC(=O)[C@H]1CNCC[C@H]1c1ccncc1]

Compound 4kk was prepared according to the method of Example 58 above from 3kk in 81% yield using 10% Pd/C at 1 atm of $H_2$ and 65° C. for 24 hours. $^1$H NMR (300 MHz, CDCl$_3$) δ 8.58-8.53 (m, 2H), 7.12 (d, J=6.1 Hz, 2H), 3.95 (qd, J=7.2, 2.2 Hz, 2H), 3.71-3.53 (m, 3H), 3.42 (dd, J=13.8, 3.6 Hz, 1H), 3.37-3.27 (m, 1H), 2.48-2.35 (m, 1H), 2.11 (dd, J=14.4, 4.0 Hz, 1H), 0.94 (t, J=7.2 Hz, 3H).

Example 93

Synthesis of (±)-syn-Ethyl 4-(pyridin-3-yl)piperidine-3-carboxylate (Compound 4ll)

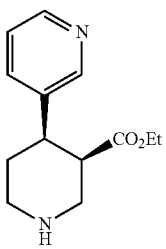 [SMILES: CCOC(=O)[C@H]1CNCC[C@H]1c1cccnc1]

Compound 4ll was prepared according to the method of Example 58 above from 3ll in 69% yield using 10% Pd/C at 1 atm of $H_2$ and 65° C. for 24 hours. $^1$H NMR (300 MHz, CDCl$_3$) δ 8.51-8.40 (m, 2H), 7.53 (dt, J=8.0, 1.7 Hz, 1H), 7.25-7.18 (m, 1H), 3.90 (q, J=7.2 Hz, 2H), 3.45-3.30 (m, 2H), 3.13-2.97 (m, 2H), 2.85-2.72 (m, 2H), 2.38 (qd, J=12.7, 4.3 Hz, 1H), 1.71 (dd, J=13.2, 2.8 Hz, 1H), 0.96 (t, J=7.2 Hz, 3H).

Example 94

Synthesis of (±)-syn-Ethyl 4-(3-((tert-butoxycarbonyl)amino)phenyl)piperidine-3-carboxylate (Compound 4qq)

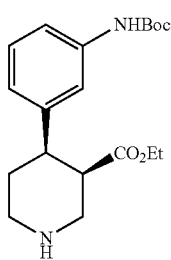 [SMILES: CCOC(=O)[C@H]1CNCC[C@H]1c1cccc(NC(=O)OC(C)(C)C)c1]

Compound 4qq was prepared according to the method of Example 58 above from 3qq in 60% yield using 10% Pd/C at 1 atm of $H_2$ and 50° C. for 24 hours. $^1$H NMR (300 MHz, CDCl$_3$) δ 7.24-7.09 (m, 2H), 6.84 (d, J=7.15 Hz, 1H), 3.89 (q, J=7.15 Hz, 2H), 3.39-3.23 (m, 2H), 3.06-2.89 (m, 2H), 2.84-2.64 (m, 2H), 2.32 (qd, J=4.27, 12.70 Hz, 1H), 1.73-1.63 (m, 1H), 1.50 (s, 9H), 0.95 (t, J=7.15 Hz, 3H).

Example 95

Synthesis of (±)-syn-Ethyl 4-(3,4-difluorophenyl)piperidine-3-carboxylate (Compound 4ss)

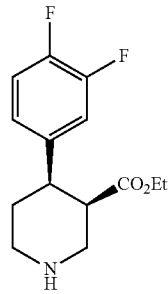 [SMILES: CCOC(=O)[C@H]1CNCC[C@H]1c1ccc(F)c(F)c1]

Compound 4ss was prepared according to the method of Example 58 above from 3ss in 60% yield using 10% Pd/C at 1 atm of $H_2$ and 50° C. for 24 hours. $^1$H NMR (300 MHz, CDCl$_3$) δ 7.13-6.96 (m, 2H), 6.95-6.86 (m, 1H), 3.92 (q, J=7.15 Hz, 2H), 3.43-3.25 (m, 2H), 3.03-2.92 (m, 2H), 2.80-2.70 (m, 2H), 2.28 (qd, J=4.40, 12.66 Hz, 1H), 2.17 (br. s., 2H), 1.65 (dq, J=3.03, 12.66 Hz, 1H), 1.00 (t, J=7.15 Hz, 3H).

Example 96

Synthesis of (±)-syn-Ethyl 4-(4-nitrophenyl)piperidine-3-carboxylate (Compound 4tt)

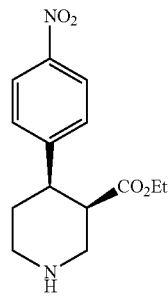 [SMILES: CCOC(=O)[C@H]1CNCC[C@H]1c1ccc([N+](=O)[O-])cc1]

Compound 4tt was prepared according to the methods of Examples 58 and 71, above. $^1$H NMR (300 MHz, CDCl$_3$) δ 8.21 (dt, J=2.20, 8.81 Hz, 2H), 7.31 (dt, J=2.20, 8.81 Hz, 2H), 3.95 (q, J=7.15 Hz, 2H), 3.85 (t, J=2.61 Hz, 2H), 3.22 (t, J=5.92 Hz, 2H), 2.65-2.45 (m, 2H), 0.95 (t, J=7.02 Hz, 3H).

Example 97

Synthesis of 4-(4-fluorophenyl)piperidine (Compound 15)

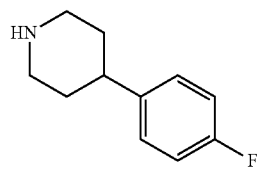 [SMILES: Fc1ccc(C2CCNCC2)cc1]

Compound 15 is referenced in Sakamuria S et al, Bioorg Med Chem Lett 11, 495-500 (2001); incorporated by reference herein. Compound 15 was prepared from 14 as a waxy white solid (167 mg, 56%) using the method of Example 58 above. $^1$H NMR (300 MHz, CDCl$_3$) δ 7.16 (dd, J=5.2, 8.8 Hz, 2H), 6.97 (t, J=8.8 Hz, 2H), 3.82 (br. s, 1H), 3.16-3.33 (m, 2H), 2.76 (dt, J=2.2, 12.1 Hz, 2H), 2.61 (tt, J=3.9, 12.10 Hz, 1H), 1.77-1.91 (m, 2H), 1.70 (dt, J=3.9, 12.4 Hz, 2H).

Example 98

General Procedure for Synthesis of APQs

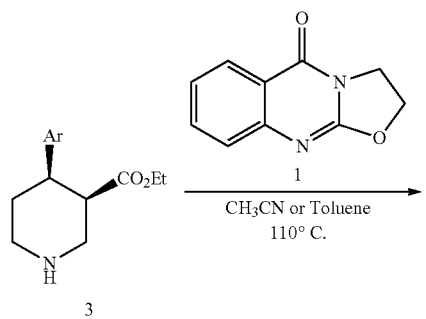

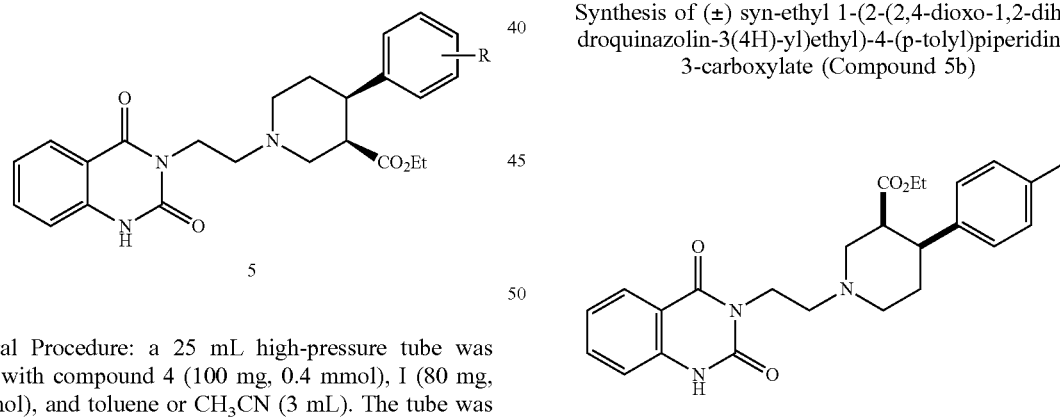

General Procedure: a 25 mL high-pressure tube was charged with compound 4 (100 mg, 0.4 mmol), I (80 mg, 0.42 mmol), and toluene or CH$_3$CN (3 mL). The tube was sealed and heated to 110° C. for 2 days. The reaction mixture was concentrated and the residue was purified by flash chromatography eluting with 0-100% CH$_2$Cl$_2$/EtOAc [R$_f$=0.3 (50% CH$_2$Cl$_2$/EtOAc)] to give compounds of series 5 as an off-white solid.

The ligands 5 were then converted to their hydrochloride salts prior to biological testing. Compounds were dissolved in CHCl$_3$ (1 ml) and 1 N HCl (2 eq) was then added and the solution was stirred for 5 minutes. The solvent was removed under reduced pressure and the crude solid was dissolved in water. After filtration and removal of the solvent by lyophilization, pure salts could be obtained in good yields.

Example 99

Synthesis of (±) syn-ethyl 1-(2-(2,4-dioxo-1,2-dihydroquinazolin-3(4H)-yl)ethyl)-4-phenylpiperidine-3-carboxylate (Compound 5a)

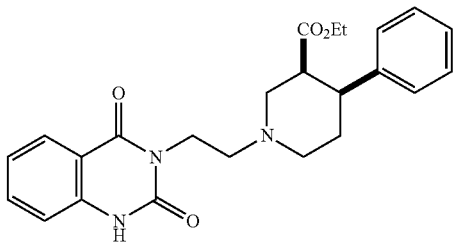 [SMILES: CCOC(=O)[C@@H]1CN(CCn2c(=O)[nH]c3ccccc3c2=O)CC[C@@H]1c1ccccc1]

Compound 5a was prepared from 4a and 1a as a white solid (59%) using the method of Example 98 above. mp=169.0-170.0° C.; R$_f$=0.33 (75% EtOAc/CH$_2$Cl$_2$); $^1$H NMR (300 MHz, CDCl$_3$) δ 9.93 (br. s, 1H), 8.11 (dd, J=1.2, 8.1 Hz, 1H), 7.58 (dt, J=1.5, 7.2 Hz, 1H), 7.31-7.12 (comp, 6H), 7.07 (d, J=8.4 Hz, 1H), 4.34-4.26 (m, 1H), 4.22-4.10 (m, 1H), 3.74 (dq, J=1.8, 7.2 Hz, 2H), 2.38 (dd, J=2.7, 8.4 Hz, 1H), 3.22 (d, J=10.8 Hz, 1H), 2.98 (d, J=3.9 Hz, 1H), 2.85 (m, 1H), 2.71 (t, J=6.9 Hz, 2H), 2.60 (dd, J=3.3, 11.1 Hz, 1H), 2.28 (dt, J=2.7, 10.8 Hz, 1H), 1.82 (dd, J=3.3, 12.6 Hz, 1H), 0.92 (t, J=7.2 Hz, 3H); $^{13}$C NMR (75 MHz, CDCl$_3$) δ 172.2, 162.4, 151.6, 143.4, 138.6, 135.0, 128.5, 128.0, 127.7, 126.1, 123.4, 114.9, 114.7, 59.7, 56.9, 55.4, 53.8, 46.5, 42.1, 38.3, 26.8, 14.0; Anal. Calcd for C$_{24}$H$_{27}$N$_3$O$_4$: C, 68.39; H, 6.46; N, 9.97. Found: C, 68.23; H, 6.44; N, 9.90; MS (APCl, [M+H]$^+$, m/z) 422.2.

Example 100

Synthesis of (±) syn-ethyl 1-(2-(2,4-dioxo-1,2-dihydroquinazolin-3(4H)-yl)ethyl)-4-(p-tolyl)piperidine-3-carboxylate (Compound 5b)

Compound 5b was prepared from 4b and 1a as an off-white solid (78%) using the method of Example 98 above. mp=212.5-213.0° C.; R$_f$=0.37 (75% EtOAc/CH$_2$Cl$_2$); $^1$H NMR (300 MHz, CDCl$_3$) δ 10.46 (br. s, 1H), 8.11 (d, J=7.8 Hz, 1H), 7.58 (dt, J=1.5, 6.6 Hz, 1H), 7.21 (t, J=6.6 Hz, 1H), 7.15-7.05 (comp, 5H), 4.36-4.25 (m, 1H), 4.24-4.13 (m, 1H), 3.82-3.70 (m, 2H), 3.37 (dd, J=3.0, 11.1 Hz, 1H), 3.20 (d, J=10.8 Hz, 1H), 2.96 (d, J=3.3 Hz, 1H), 2.87-2.77 (m, 1H), 2.71 (t, J=7.5 Hz, 2H), 2.66-2.50 (comp, 2H), 2.32-2.17 (comp, 4H), 1.84-1.77 (m, 1H), 0.94 (t, J=7.2 Hz, 3H); Anal. Calcd for C$_{27}$H$_{31}$N$_3$O$_6$: C, 68.95; H, 6.71; N, 9.65. Found: C, 68.90; H, 6.79; N, 9.65; MS (APCl, [M+H]$^+$, m/z) 436.2.

Example 101

Synthesis of (±) syn-ethyl 4-(2,3-dihydrobenzo[b][1,4]dioxin-5-yl)-1-(2-(2,4-dioxo-1,2-dihydro-quinazolin-3(4H)-yl)ethyl)piperidine-3-carboxylate (Compound 5c)

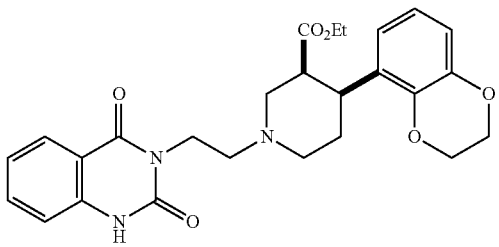 [SMILES: CCOC(=O)[C@@H]1CN(CCn2c(=O)[nH]c3ccccc3c2=O)CC[C@@H]1c1cccc2c1OCCO2]

Compound 5c was prepared from 4c and 1a as a white solid (61%) using the method of Example 98 above. mp=197.0-198.0° C.; $R_f$=0.20 (70% EtOAc/CH$_2$Cl$_2$); $^1$H NMR (300 MHz, CDCl$_3$) δ 9.53 (br. s, 1H), 8.10 (dd, J=1.5, 7.8 Hz, 1H), 7.58 (dt, J=1.5, 6.9 Hz, 1H), 7.21 (t, J=7.2 Hz, 1H), 7.04 (d, J=7.8 Hz, 1H), 6.77-6.72 (comp, 3H), 4.30-4.10 (comp, 6H), 3.77 (q, J=7.2 Hz, 2H), 3.34 (dd, J=2.4, 10.5 Hz, 1H), 3.18 (d, J=11.1 Hz, 1H), 2.91 (d, J=3.6 Hz, 1H), 2.78-2.67 (comp, 3H), 2.58-2.46 (comp, 2H), 2.25 (t, J=8.4 Hz, 1H), 1.77 (dd, J=2.7, 12.9 Hz, 1H), 0.97 (t, J=7.2 Hz, 3H); Anal. Calcd for C$_{26}$H$_{29}$N$_3$O$_6$: C, 65.12; H, 6.10; N, 8.76. Found: C, 64.83; H, 6.02; N, 8.54; MS (APCl, [M+H]$^+$, m/z) 480.1.

| hVMAT2 [$^3$H]DTBZ Ki (nM) ± SEM | hVMAT2 5HT Uptake IC$_{50}$ (nM) ± SEM | 5-HT1A [$^3$H] 8—OH DPAT Ki(nM) ± SEM | 5-HT2A [$^{125}$I]DOI Ki (nM) ± SEM |
|---|---|---|---|
| >9 μM | 156 ± 42 | ND | ND |

Example 102

Synthesis of (±) syn-ethyl 1-(2-(2,4-dioxo-1,2-dihydroquinazolin-3(4H)-yl)ethyl)-4-(4-fluoro phenyl)piperidine-3-carboxylate (Compound 5d)

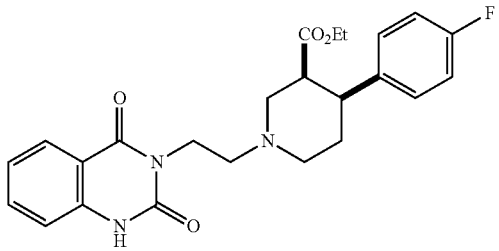 [SMILES: CCOC(=O)[C@@H]1CN(CCn2c(=O)[nH]c3ccccc3c2=O)CC[C@@H]1c1ccc(F)cc1]

Compound 5d was prepared from 4d and 1a as an off-white solid (40%) using the method of Example 98 above (Note: the product can also be purified by recrystallization in EtOAc): mp=173.0-175.0° C.; $^1$H NMR (300 MHz, CDCl$_3$) δ 10.29 (br. s., 1H), 8.11 (d, J=8.3 Hz, 1H), 7.59 (t, J=7.7 Hz, 1H), 7.15-7.25 (m, 3H), 7.10 (d, J=8.3 Hz, 1H), 6.92 (t, J=8.8 Hz, 2H), 4.24-4.40 (m, 1H), 4.09-4.24 (m, 1H), 3.75 (q, J=6.9 Hz, 2H), 3.38 (d, J=11.0 Hz, 1H), 3.22 (d, J=11.0 Hz, 1H), 2.88-3.01 (m, 1H), 2.77-2.88 (m, 1H), 2.66-2.77 (m, 2H), 2.57 (dd, J=2.5, 11.0 Hz, 2H), 2.26 (td, J=2.5, 11.0 Hz, 1H), 1.69-1.93 (m, 1H), 0.93 (t, J=7.2 Hz, 3H); $^{13}$C NMR (75 MHz, DMSO-d$_6$) δ 171.8, 162.6, 162.4, 159.4, 150.7, 140.2, 140.0, 135.4, 129.7, 129.6, 127.9, 122.9, 115.6, 115.0, 114.7, 114.3, 59.5, 57.2, 55.3, 53.9, 46.0, 40.9, 37.9, 26.5, 14.3; Anal. Calcd for C$_{24}$H$_{26}$N$_3$O$_4$F: C, 65.59; H, 5.96; N, 9.56; F, 4.32. Found: C, 65.51; H, 5.93; N, 9.49; F, 4.41; MS (APCl, [M+H]$^+$, m/z) 440.2.

Example 103

Synthesis of (±)-syn-Ethyl 1-(2-(2,4-dioxo-1,2-dihydroquinazolin-3(4H)-yl)ethyl)-4-(4-fluoro phenyl)piperidine-3-carboxylate (Compound 5e)

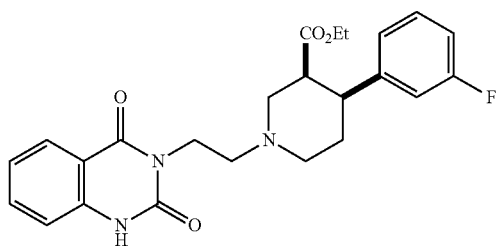 [SMILES: CCOC(=O)[C@@H]1CN(CCn2c(=O)[nH]c3ccccc3c2=O)CC[C@@H]1c1cccc(F)c1]

Compound 5e was prepared from 4e and 1a as an off-white solid (40%) using the method of Example 98 above mp=170.6-171.4° C.; $^1$H NMR (300 MHz, CDCl$_3$) δ 9.91 (s, 1H), 8.12 (dd, J=1.65, 7.98 Hz, 1H), 7.59 (td, J=1.65, 7.71 Hz, 1H), 7.25-7.14 (m, 2H), 7.08 (d, J=7.98 Hz, 1H), 7.01 (d, J=7.71 Hz, 1H), 6.96 (dt, J=2.17, 10.53 Hz, 1H), 6.89-6.79 (m, 1H), 4.38-4.23 (m, 1H), 4.22-4.09 (m, 1H), 3.75 (q, J=7.15 Hz, 2H), 3.39 (dd, J=2.34, 11.14 Hz, 1H), 3.23 (d, J=11.28 Hz, 1H), 3.00-2.92 (m, 1H), 2.83 (dt, J=4.16, 11.76 Hz, 3H), 2.71 (t, J=6.74 Hz, 2H), 2.63-2.49 (m, 2H), 2.39-2.19 (m, 1H), 1.81 (dd, J=3.58, 12.93 Hz, 1H), 0.93 (t, J=7.15 Hz, 3H); $^{13}$C NMR (75 MHz, CDCl$_3$) δ 171.9, 164.4, 162.4, 161.1, 151.8, 146.2, 146.1, 138.7, 135.0, 129.4, 129.3, 128.5, 123.4, 123.2, 123.2, 114.9, 114.8, 114.7, 114.5, 113.1, 112.8, 59.9, 56.9, 55.4, 53.7, 46.3, 41.8, 38.3, 26.7, 14.0.; Anal. (C$_{24}$H$_{26}$N$_3$O$_4$F) C, H, N, F. MS (APCl, [M+H]$^+$, m/z) 440.2.

Example 104

Synthesis of (±) syn-ethyl 1-(2-(2,4-dioxo-1,2-dihydroquinazolin-3(4H)-yl)ethyl)-4-(4-(trifluoromethyl)phenyl)piperidine-3-carboxylate (Compound 5f)

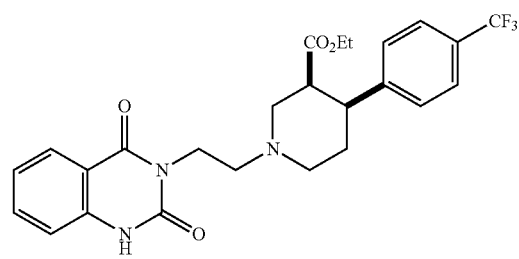 [SMILES: CCOC(=O)[C@@H]1CN(CCn2c(=O)[nH]c3ccccc3c2=O)CC[C@@H]1c1ccc(C(F)(F)F)cc1]

Compound 5f was prepared from 4f and 1a as an off-white solid (40%) using the method of Example 98 above. mp=211.5-212.0° C.; $R_f$=0.40 (75% EtOAc/hexanes, 1% i-Pr—NH$_2$); $^1$H NMR (300 MHz, CDCl$_3$) δ 9.02 (br. s, 1H), 8.02 (d, J=8.1 Hz, 1H), 7.58 (t, J=7.8 Hz, 1H), 7.50 (d, J=8.1 Hz, 2H), 7.37 (d, J=8.1 Hz, 2H), 7.27-7.20 (m, 1H), 7.03 (d, J=7.8 Hz, 1H), 4.33-4.24 (m, 1H), 4.17-4.09 (m, 1H), 3.70 (q, J=7.2 Hz, 2H), 3.39 (d, J=10.8 Hz, 1H), 3.26 (d, J=12.3 Hz, 1H), 3.00-2.94 (m, 1H), 2.91-2.83 (m, 1H), 2.73-2.69 (m, 2H), 2.65-2.56 (comp, 2H), 2.29-2.19 (m, 1H), 1.82 (d, J=13.2 Hz, 1H), 0.92 (t, J=7.2 Hz, 3H); Anal. Calcd for C$_{25}$H$_{26}$F$_3$N$_3$O$_4$: C, 61.34; H, 5.35; N, 8.58; F, 11.64. Found: C, 61.26; H, 5.37; N, 8.37; F, 11.55; MS (APCI, [M+H]$^+$, m/z) 490.1.

Example 105

Synthesis of (±) syn-ethyl 1-(2-(2,4-dioxo-1,2-dihydroquinazolin-3(4H)-yl)ethyl)-4-(3-(trifluoromethyl)phenyl)piperidine-3-carboxylate (Compound 5g)

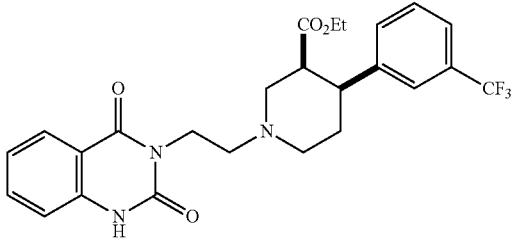 [SMILES: CCOC(=O)[C@@H]1CN(CCn2c(=O)[nH]c3ccccc3c2=O)CC[C@@H]1c1cccc(C(F)(F)F)c1]

Compound 5g was prepared from 4g and 1a as an off-white solid (45%) using the method of Example 98 above. mp=181.0-182.0° C.; $R_f$=0.40 (75% EtOAc/hexanes, 1% i-Pr—NH$_2$); $^1$H NMR (300 MHz, CDCl$_3$) δ 9.50 (br. s, 1H), 8.12 (dd, J=1.2, 8.1 Hz, 1H), 7.62-7.33 (comp, 5H), 7.19-7.23 (m, 1H), 7.05 (d, J=8.1 Hz, 1H), 4.34-4.27 (m, 1H), 4.19-4.11 (m, 1H), 3.72 (q, J=6.9 Hz, 2H), 3.41 (d, J=11.4 Hz, 1H), 3.26 (d, J=10.5 Hz, 1H), 2.98 (d, J=3.3 Hz, 1H), 2.92-2.84 (m, 1H), 2.72 (t, J=7.2 Hz, 2H), 2.65-2.54 (comp, 2H), 2.26 (dt, J=2.7, 11.1 Hz, 1H), 1.83 (dd, J=3.0, 12.9 Hz, 1H), 0.91 (t, J=7.2 Hz, 3H); Anal. Calcd for C$_{25}$H$_{26}$F$_3$N$_3$O$_4$: C, 61.34; H, 5.35; N, 8.58; F, 11.64. Found: C, 61.27; H, 5.33; N, 8.48; F, 11.75; MS (APCI, [M+H]$^+$, m/z) 490.1.

Example 106

Synthesis of (±) syn-ethyl 4-(4-(dimethylamino)phenyl)-1-(2-(2,4-dioxo-1,2-dihydroquinazolin-3(4H)-yl)ethyl)piperidine-3-carboxylate (Compound 5h)

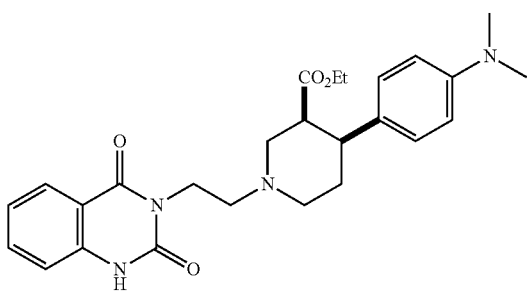 [SMILES: CCOC(=O)[C@@H]1CN(CCn2c(=O)[nH]c3ccccc3c2=O)CC[C@@H]1c1ccc(N(C)C)cc1]

Compound 5h was prepared from 4h and 1a as an off-white solid (55%) using the method of Example 98 above. mp=203.0-204.0° C.; $R_f$=0.38 (75% EtOAc/hexanes, 1% i-Pr—NH$_2$); $^1$H NMR (300 MHz, CDCl$_3$) δ 9.79 (br. s, 1H), 8.11 (dd, J=1.5, 6.6 Hz, 1H), 7.57 (dt, J=1.5, 6.9 Hz, 1H), 7.20 (t, J=7.5 Hz, 1H), 7.13 (d, J=8.7 Hz, 2H), 7.06 (d, J=8.4 Hz, 1H), 6.65 (d, J=8.7 Hz, 2H), 4.33-4.14 (m, 2H), 3.82-3.73 (m, 2H), 3.33 (dd, J=2.7, 10.8 Hz, 1H), 3.17 (d, J=10.8 Hz, 1H), 2.95-2.87 (comp, 7H), 2.83-2.65 (comp, 3H), 2.63-2.49 (comp, 2H), 2.28 (dt, J=2.4, 10.8 Hz, 1H), 1.77 (dd, J=3.0, 12.6 Hz, 1H), 0.96 (t, J=7.2 Hz, 3H); $^{13}$C NMR (75 MHz, CDCl$_3$) δ 172.5, 162.4, 151.8, 149.1, 138.7, 135.0, 131.5, 128.4, 123.3, 114.9, 114.7, 112.6, 59.7, 56.7, 55.5, 53.9, 46.6, 41.4, 40.9, 38.3, 27.3, 14.1; Anal. Calcd for C$_{26}$H$_{32}$N$_4$O$_4$: C, 66.45; H, 6.99; N, 11.92. found: C, 66.31; H, 7.01; N, 11.78; MS (APCI, [M+H]$^+$, m/z) 465.2.

Example 107

Synthesis of (±) syn-ethyl 4-(4-carbamoylphenyl)-1-(2-(2,4-dioxo-1,2-dihydroquinazolin-3(4H)-yl)ethyl)piperidine-3-carboxylate (Compound 5i)

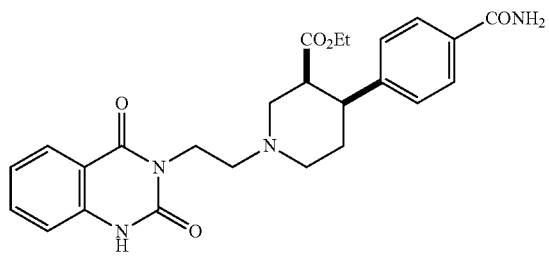 [SMILES: CCOC(=O)[C@@H]1CN(CCn2c(=O)[nH]c3ccccc3c2=O)CC[C@@H]1c1ccc(C(N)=O)cc1]

Compound 5i was prepared from 4i and 1a as a white solid (73 mg, 38%) using the method of Example 98 above except use of DMF/1,4-dioxane (2/3, Vol/Vol) as solvent (Note: the product showed a poor solubility in many organic solvents and was purified by washing with EtOAc/MeOH (1/1, Vol/Vol)): $^1$H NMR (300 MHz, DMSO-d$_6$) δ 11.41 (br. s, 1H), 7.92 (dd, J=1.2, 7.8 Hz, 1H), 7.88 (br. s, 1H), 7.75 (d, J=8.1 Hz, 2H), 7.64 (t, J=7.8 Hz, 1H), 7.33 (d, J=8.1 Hz, 2H), 7.27 (br. s, 1H), 7.21-7.15 (comp, 2H), 4.13-4.03 (m, 1H), 3.95-3.87 (m, 1H), 3.68-3.57 (m, 2H), 3.23 (d, J=11.1 Hz, 1H), 3.14-3.09 (comp, 2H), 2.87-2.82 (m, 1H), 2.58-2.39 (comp, 4H), 2.17-2.08 (m, 1H), 1.77 (d, J=9.6 Hz, 1H), 0.86 (t, J=7.2 Hz, 3H); $^{13}$C NMR (75 MHz, DMSO-d$_6$) δ 171.8, 168.4, 162.4, 150.7, 147.6, 140.0, 135.5, 132.3, 127.9, 127.6, 127.5, 123.0, 115.6, 114.3, 59.6, 57.3, 55.3, 53.8, 45.9, 41.3, 37.9, 26.3, 14.3; Anal. Calcd for C$_{25}$H$_{28}$N$_4$O$_5$: C, 64.64; H, 6.08; N, 12.06. Found: C, 64.14; H, 6.08; N, 11.97; MS (APCI, [M+H]$^+$, m/z) 465.2.

Example 108

Synthesis of (±) syn-ethyl 4-([1,1'-biphenyl]-4-yl)-1-(2-(2,4-dioxo-1,2-dihydroquinazolin-3(4H)-yl)ethyl)piperidine-3-carboxylate (Compound 5j)

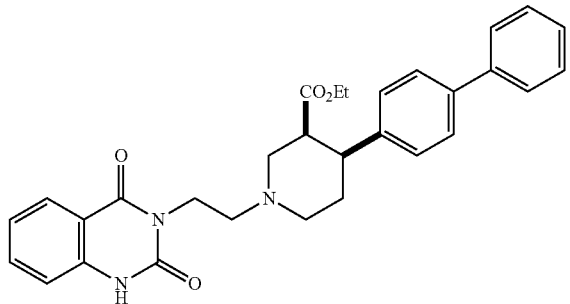 [SMILES: CCOC(=O)[C@@H]1CN(CCn2c(=O)[nH]c3ccccc3c2=O)CC[C@@H]1c1ccc(-c2ccccc2)cc1]

Compound 5j was prepared from 4j and 1a as an off-white solid (65%) using the general procedure described above. mp=219.0-220.0° C.; $R_f$=0.40 (75% EtOAc/hexanes, 1% i-Pr—NH$_2$); $^1$H NMR (300 MHz, CDCl$_3$) δ 9.77 (br. s, 1H), 8.12 (dd, J=1.2, 7.8 Hz, 1H), 7.61-7.27 (comp, 10H), 7.21 (t, J=7.8 Hz, 1H), 7.07 (d, J=7.8 Hz, 1H), 4.36-4.27 (m, 1H), 4.23-4.14 (m, 1H), 3.40 (d, J=8.7 Hz, 1H), 3.24 (d, J=11.4 Hz, 1H), 3.01 (d, J=3.6 Hz, 1H), 2.93-2.85 (m, 1H), 2.73 (t, J=6.9 Hz, 2H), 2.67-2.56 (comp, 2H), 2.30 (dt, J=2.7, 10.8 Hz, 1H), 1.85 (dd, J=3.6, 12.9 Hz, 1H), 0.94 (t, J=7.2 Hz, 3H); Anal. Calcd for C$_{27}$H$_{31}$N$_3$O$_6$: C, 68.95; H, 6.71; N, 9.65. Found: C, 68.90; H, 6.79; N, 9.65; MS (APCI, [M+H]$^+$, m/z) 498.2.

Example 109

Synthesis of (±) syn-ethyl 4-(1-(tert-butoxycarbonyl)-1H-pyrrol-2-yl)-1-(2-(2,4-dioxo-1,2-dihydroquinazolin-3(4H)-yl)ethyl)piperidine-3-carboxylate (Compound 5k)

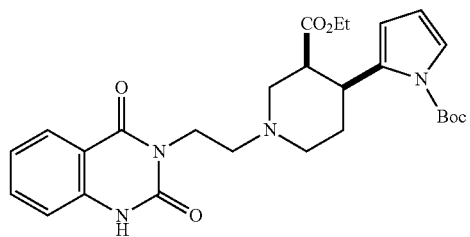 [SMILES: CCOC(=O)[C@@H]1CN(CCn2c(=O)[nH]c3ccccc3c2=O)CC[C@@H]1c1cccn1C(=O)OC(C)(C)C]

Compound 5k was prepared from 4k and 1a as a viscous yellow oil (144 mg, 58%) using the method of Example 98 above. $R_f$=0.10 (5% MeOH/CH$_2$Cl$_2$); $^1$H NMR (300 MHz, CDCl$_3$) δ 9.70 (br. s, 1H), 8.10 (d, J=7.8 Hz, 1H), 7.59 (ddd, J=1.8, 7.2, 9.0 Hz, 1H), 7.20 (t, J=7.5 Hz, 1H), 7.14 (dd, J=1.5, 3.3 Hz, 1H), 7.08 (d, J=8.1 Hz, 1H), 6.11 (br. s, 1H), 6.04 (t, J=3.3 Hz, 1H), 4.31-4.14 (m, 2H), 3.86-3.75 (m, 2H), 3.54 (m, 1H), 3.29 (dd, J=3.6, 11.4 Hz, 1H), 3.15-3.07 (comp, 2H), 2.73-2.56 (comp, 3H), 2.46 (m, 1H), 2.28 (m, 1H), 1.75 (d, J=12.6 Hz, 1H), 1.57 (s, 9H), 0.98 (t, J=7.2 Hz, 3H); $^{13}$C NMR (75 MHz, CDCl$_3$) δ 172.5, 162.4, 151.7, 149.5, 138.6, 137.0, 135.0, 128.5, 123.3, 121.0, 114.9, 114.7, 112.5, 110.0, 83.4, 59.6, 55.9, 55.5, 53.7, 44.0, 38.3, 35.6, 28.2, 27.9, 14.0.

Example 110

Synthesis of (±) syn-ethyl 1-(2-(2,4-dioxo-1,2-dihydroquinazolin-3(4H)-yl)ethyl)-4-(4-(ethoxycarbonyl)phenyl)piperidine-3-carboxylate (Compound 5l)

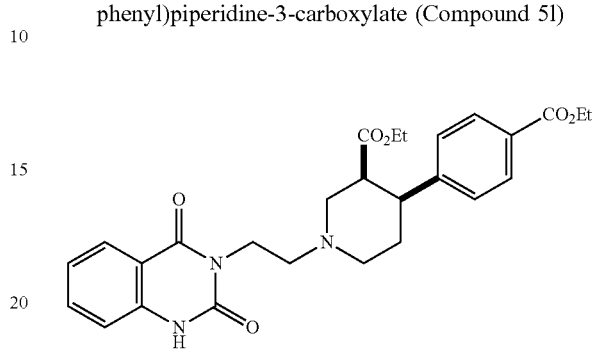

Compound 5l was prepared from 4l and 1a as an off-white solid (64%) using the method of Example 98 above. mp=213.0-213.5° C.; $R_f$=0.30 (75% EtOAc/CH$_2$Cl$_2$); $^1$H NMR (300 MHz, CDCl$_3$) δ 9.71 (br. s, 1H), 8.11 (dd, J=1.5, 8.1 Hz, 1H), 7.93 (d, J=8.4 Hz, 2H), 7.58 (dt, J=1.2, 7.2 Hz, 1H), 7.32 (d, J=8.4 Hz, 2H), 7.21 (t, J=7.2 Hz, 1H), 7.05 (d, J=8.4 Hz, 1H), 4.37-4.26 (comp, 3H), 4.20-4.11 (m, 1H), 3.72 (q, J=7.2 Hz, 2H), 3.40 (d, J=9.9 Hz, 1H), 3.24 (d, J=9.9 Hz, 1H), 2.99 (d, J=3.3 Hz, 1H), 2.82-2.75 (m, 1H), 2.71 (t, J=6.6 Hz, 2H), 2.65-2.54 (comp, 2H), 2.25 (dt, J=2.7, 11.1 Hz, 1H), 1.84 (dd, J=3.0, 12.6 Hz, 1H), 1.36 (t, J=7.2 Hz, 3H), 0.91 (t, J=7.2 Hz, 3H); Anal. Calcd for C$_{27}$H$_{31}$N$_3$O$_6$: C, 65.71; H, 6.33; N, 8.51. Found: C, 65.94; H, 6.31; N, 8.48; MS (APCI, [M+H]$^+$, m/z) 494.2.

Example 111

Synthesis of (±) syn-ethyl 1-(2-(2,4-dioxo-1,2-dihydroquinazolin-3(4H)-yl)ethyl)-4-(thiophen-2-yl)piperidine-3-carboxylate (Compound 5m)

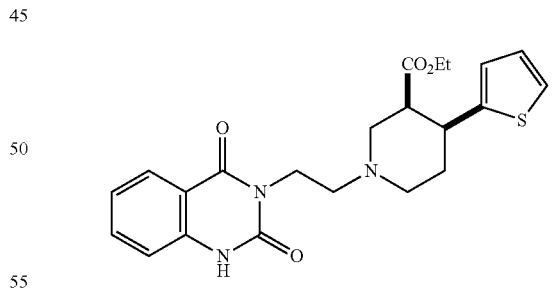

Compound 5m was prepared from 4m and 1a as an off-white solid (158 mg, 60%) using the method of Example 98 above (Note: the pure product was obtained by recrystallization in EtOAc/Et$_2$O): mp=152.2-153.5° C.; $R_f$=0.31 (10% MeOH/CH$_2$Cl$_2$); $^1$H NMR (300 MHz, CDCl$_3$) δ 10.30 (br. s, 1H), 8.10 (dd, J=1.2, 7.8 Hz, 1H), 7.59 (ddd, J=1.5, 6.6, 8.1 Hz, 1H), 7.21 (t, J=6.6 Hz, 1H), 7.13-7.07 (comp, 2H), 6.88 (dd, J=3.3, 5.1 Hz, 1H), 3.82 (d, J=3.3 Hz, 1H), 4.33-4.16 (m, 2H), 3.86 (q, J=6.9 Hz, 2H), 3.38 (br. s, 1H), 3.09 (dd, J=6.9, 10.8, Hz, 1H), 3.01-2.96 (comp, 2H), 2.83-2.71 (comp, 3H), 2.56-2.49 (m, 1H), 2.39-2.29 (m, 1H), 2.04-1.96 (m, 1H), 1.01 (t, J=6.9 Hz, 3H); $^{13}$C NMR (75 MHz, CDCl$_3$) □ 172.1, 162.4, 151.8, 146.3, 138.7, 135.1, 128.5, 126.4, 124.5, 123.4, 123.3, 115.0, 114.7, 60.1, 55.5, 54.2, 52.0, 46.5, 38.3, 37.6, 30.0, 14.0; Anal. Calcd for C$_{22}$H$_{25}$N$_3$O$_4$S: C, 61.81; H, 5.89; N, 9.83; S, 7.50. Found: C, 61.71; H, 5.79; N, 9.75; S, 7.29; MS (APCl, [M+H]$^+$, m/z) 428.1.

Example 112

(±) syn-ethyl 1-(2-(2,4-dioxo-1,2-dihydroquinazolin-3(4H)-yl)ethyl)-4-(5-methylthiophen-2-yl)piperidine-3-carboxylate (Compound 5n)

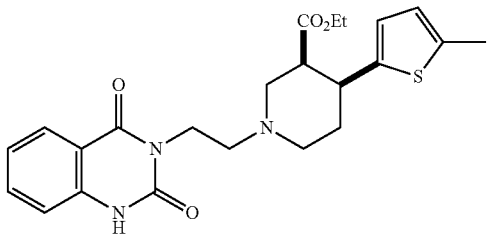 [SMILES: CCOC(=O)[C@@H]1CN(CCn2c(=O)[nH]c3ccccc3c2=O)CC[C@@H]1c1ccc(C)s1]

Compound 5n was prepared from 4n and 1a as an off-white solid (56 mg, 20%) using the method of Example 98 above. R$_f$=0.20 (80% EtOAc/hexanes, 1% MeOH, 1% Et$_3$N); $^1$H NMR (300 MHz, CDCl$_3$) δ 9.14 (br. s, 1H), 8.10 (d, J=7.8 Hz, 1H), 7.58 (m, 1H), 7.21 (t, J=7.8 Hz, 1H), 7.03 (d, J=8.4 Hz, 1H), 6.59 (d, J=3.3 Hz, 1H), 6.52 (dd, J=1.2, 3.3 Hz, 1H), 4.28-4.16 (m, 2H), 3.88 (q, J=7.2 Hz, 2H), 3.30 (br. s, 1H), 3.08-3.02 (m, 1H), 2.95-2.90 (comp, 2H), 2.79-2.69 (comp, 3H), 2.53 (br. s, 1H), 2.39 (s, 3H), 2.27 (br. s, 1H), 1.98-1.90 (m, 1H), 1.04 (t, J=7.2 Hz, 3H); $^{13}$C NMR (75 MHz, CDCl$_3$) δ 172.1, 162.3, 151.8, 143.6, 138.6, 137.6, 134.9, 128.3, 124.3, 123.3, 114.9, 114.6, 59.9, 55.5, 53.8, 51.7, 46.2, 38.2, 37.6, 30.0, 15.2, 14.0; Anal. Calcd for C$_{23}$H$_{27}$N$_3$O$_4$S: C, 62.56; H, 6.16; N, 9.52; S, 7.26. Found: C, 62.49; H, 6.12; N, 9.37; S, 7.26; MS (APCl, [M+H]$^+$, m/z) 442.2.

Example 113

Synthesis of (±) syn-ethyl 1-(2-(2,4-dioxo-1,2-dihydroquinazolin-3(4H)-yl)ethyl)-4-(4-(1-hydroxyethyl)phenyl)piperidine-3-carboxylate (Compound 5p)

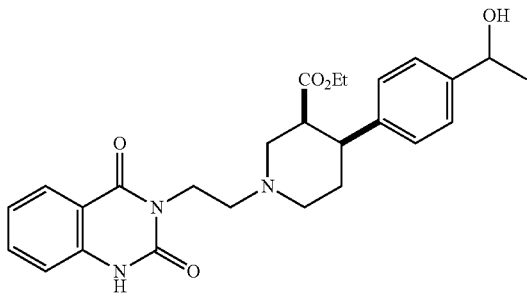 [SMILES: CCOC(=O)[C@@H]1CN(CCn2c(=O)[nH]c3ccccc3c2=O)CC[C@@H]1c1ccc(C(C)O)cc1]

Compound 5p was prepared from 4p and 1a as an off-white solid (13%) using the method of Example 98 above. mp=187.0-188.0° C.; R$_f$=0.15 (70% EtOAc/hexanes, 1% i-Pr—NH$_2$); $^1$H NMR (300 MHz, CDCl$_3$) δ 9.58 (br. s, 1H), 8.11 (d, J=7.5 Hz, 1H), 7.58 (t, J=7.8 Hz, 1H), 7.31-7.17 (comp, 5H), 7.05 (d, J=7.8 Hz, 1H), 4.89-4.81 (m, 1H), 4.33-4.23 (m, 1H), 4.21-4.09 (m, 1H), 3.73 (q, J=6.6 Hz, 2H), 3.37 (d, J=10.2 Hz, 1H), 3.21 (d, J=10.5 Hz, 1H), 2.95 (br. s, 1H), 2.87-2.78 (m, 1H), 2.70 (t, J=6.6 Hz, 2H), 2.65-2.51 (comp, 2H), 2.26 (t, J=11.1 Hz, 1H), 1.77 (d, J=3.3 Hz, 1H), 1.45 (d, J=6.3 Hz, 3H), 0.93 (t, J=6.6 Hz, 3H); $^{13}$C NMR (75 MHz, CDCl$_3$) δ 172.1, 162.4, 151.9, 143.5, 142.7, 138.7, 135.0, 128.4, 127.8, 125.1, 123.3, 115.0, 114.7, 70.3, 59.7, 56.9, 55.4, 53.8, 46.4, 41.9, 38.3, 26.9, 25.1, 14.0; Anal. Calcd for C$_{26}$H$_{31}$N$_3$O$_5$: C, 65.84; H, 6.80; N, 8.85. Found: C, 65.88; H, 6.62; N, 8.91; MS (APCl, [M+H]$^+$, m/z) 466.2.

Example 114

Synthesis of (±)-syn-Ethyl 1-(2-(2,4-dioxo-1,2-dihydroquinazolin-3(4H),-yl)ethyl)-4-(3-methoxyphenyl)piperidine-3-carboxylate (Compound 5q)

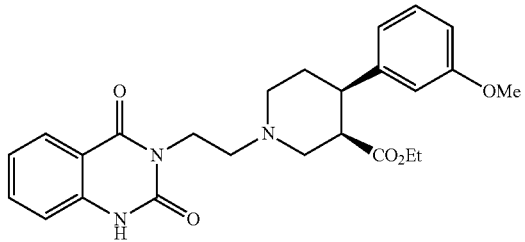 [SMILES: CCOC(=O)[C@H]1CN(CCn2c(=O)[nH]c3ccccc3c2=O)CC[C@H]1c1cccc(OC)c1]

Compound 5q was prepared in 72% yield from 1a and 4q using the method of Example 98 above. MP(HCl)=184.6-186.0° C. $^1$H NMR (300 MHz, CDCl$_3$) δ 9.75 (s, 1H), 8.11 (dd, J=1.65, 7.98 Hz, 1H), 7.63-7.53 (m, 1H), 7.24-7.13 (m, 3H), 7.06 (d, J=8.26 Hz, 1H), 6.82-6.75 (m, 8H), 4.37-4.10 (m, 2H), 3.78-3.72 (m, 2H), 3.75 (s, 3H), 3.35 (ddd, J=1.51, 3.23, 11.21 Hz, 1H), 3.20 (d, J=12.38 Hz, 1H), 2.96-2.88 (m, 1H), 2.80 (dt, J=4.13, 11.56 Hz, 1H), 2.74-2.64 (m, 2H), 2.64-2.50 (m, 2H), 2.33-2.18 (m, 1H), 1.77 (dd J=3.30, 12.38 Hz, 1H), 0.94 (t, J=7.15 Hz, 3H). $^{13}$C NMR (75 MHz, CDCl$_3$) δ 172.3, 162.4, 157.8, 151.7, 138.6, 135.5, 135.0, 128.7, 128.5, 123.3, 114.9, 114.7, 113.4, 59.7, 56.8, 55.4, 55.3, 53.8, 46.5, 41.4, 38.3, 27.1, 14.0. Anal. (C$_{27}$H$_{33}$N$_3$O$_4$; 1.2HCl; 1.3H$_2$O) C, H, N.

Example 115

Synthesis of (±)-syn-Ethyl 1-(2-(2,4-dioxo-1,2-dihydroquinazolin-3(4H),-yl)ethyl)-4-(4-methoxyphenyl)piperidine-3-carboxylate (Compound 5r)

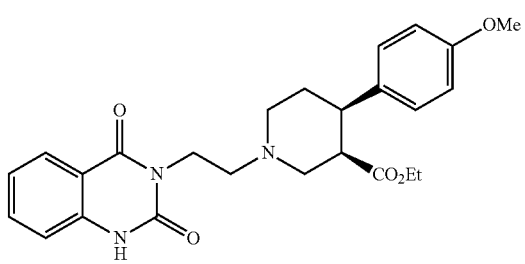 [SMILES: CCOC(=O)[C@H]1CN(CCn2c(=O)[nH]c3ccccc3c2=O)CC[C@H]1c1ccc(OC)cc1]

Compound 5r was prepared in 72% yield from 1a and 4r using the method of Example 98 above. MP(HCl)=153-154° C. MP(HCl)=168.5-170° C. $^1$H NMR (300 MHz, CDCl$_3$) δ 9.63 (s, 1H), 8.11 (d, J=8.0 Hz, 1H), 7.58 (td, J=1.6, 7.7 Hz, 1H), 7.24-7.13 (m, 3H), 7.05 (d, J=8.0 Hz, 1H), 6.79 (d, J=8.8 Hz, 2H), 4.35-4.22 (m, 1H), 4.22-4.09 (m, 1H), 3.76 (s, 3H), 3.81-3.67 (m, 2H), 3.35 (d, J=11.0 Hz, 1H), 3.20 (d, J=11.3 Hz, 1H), 2.92 (q, J=3.3 Hz, 1H), 2.86-2.75 (m, 1H), 2.75-2.65 (m, 2H), 2.57 (dd, J=3.2, 11.4 Hz, 2H), 2.32-2.20 (m, 1H), 1.83-1.72 (m, 1H), 0.94 (t, J=7.2 Hz, 3H). $^{13}$C NMR (75 MHz, CDCl$_3$) δ 172.3, 162.4, 157.8, 151.7, 138.7, 135.5, 135.0, 128.7, 128.5, 123.4, 114.9, 114.7, 113.4, 59.7, 56.8, 55.5, 55.3, 53.9, 46.6, 41.4, 38.3, 27.1, 14.0. Anal. (C$_{25}$H$_{29}$N$_3$O$_5$.1.2HCl.1.3H$_2$O) C, H, N, Cl.

Example 116

Synthesis of (±)-syn-Ethyl 4-(4-((tert-butoxycarbonyl)amino)phenyl)-1-(2-(2,4-dioxo-1,2-dihydroquinazolin-3(4H)-yl)ethyl)piperidine-3-carboxylate (Compound 5s)

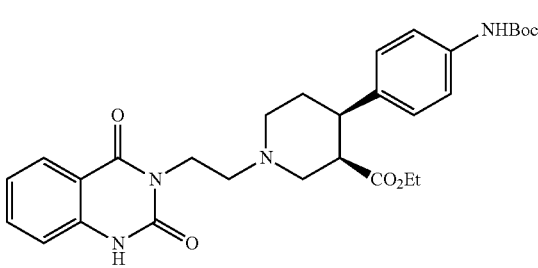 [SMILES: CCOC(=O)[C@H]1CN(CCn2c(=O)[nH]c3ccccc3c2=O)CC[C@H]1c1ccc(NC(=O)OC(C)(C)C)cc1]

Compound 5s was prepared in 93% yield from 1a and 4s using the method of Example 98 above. $^1$H NMR (300 MHz, CDCl$_3$) δ 7.98 (dd, J=1.65, 7.98 Hz, 1H), 7.56-7.41 (m, 1H), 7.30-7.20 (m, 2H), 7.20-7.04-7.20 (m, 3H), 7.00 (d, J=7.98 Hz, 1H), 4.22-3.95 (m, 2H), 3.76-3.59 (m, 2H), 3.46-3.35 (m, 4H), 3.32-3.14 (m, 2H), 3.05 (d, J=12.11 Hz, 1H), 2.86 (q, J=3.76 Hz, 1H), 2.81-2.67 (m, 1H), 2.67-2.33 (m, 4H), 2.29-2.12 (m, 1H), 1.80-1.65 (m, 1H), 1.41 (s, 9H), 0.88 (t, J=7.15 Hz, 3H).

Example 117

Synthesis of (±)-syn-Ethyl 1-(2-(2,4-dioxo-1,2-dihydroquinazolin-3(4H),-yl)ethyl)-4-(4-ethylphenyl)piperidine-3-carboxylate (Compound 5t)

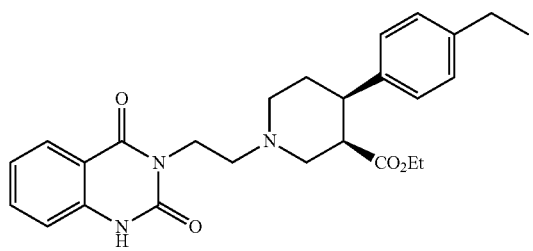 [SMILES: CCOC(=O)[C@H]1CN(CCn2c(=O)[nH]c3ccccc3c2=O)CC[C@H]1c1ccc(CC)cc1]

Compound 5t was prepared in 58% yield from 1a and 4t using the method of Example 98 above. MP(HCl)=145-146° C. $^1$H NMR (300 MHz, CDCl$_3$) δ 9.79 (s, 1H), 8.11 (dd, J=1.1, 8.0 Hz, 1H), 7.58 (tq, J=1.6, 8.0 Hz, 1H), 7.25-7.13 (m, 3H), 7.09 (d, J=2.5 Hz, 2H), 7.06 (d, J=2.7 Hz, 1H), 4.37-4.09 (m, 2H), 3.75 (qd, J=6.9, 2.2 Hz, 2H), 3.37 (dd, J=3.0, 11.3 Hz, 1H), 3.20 (d, J=11.0 Hz, 1H), 3.01-2.90 (m, 1H), 2.90-2.76 (m, 1H), 2.71 (t, J=6.5 Hz, 2H), 2.64-2.51 (m, 4H), 2.27 (td, J=2.7, 10.9 Hz, 1H), 1.80 (dd, J=3.2, 13.1 Hz, 1H), 1.19 (t, J=7.6 Hz, 3H), 0.93 (t, J=7.1 Hz, 3H). $^{13}$C NMR (75 MHz, CDCl$_3$) δ 172.3, 162.4, 151.8, 141.9, 140.6, 138.7, 135.0, 128.5, 127.7, 127.5, 123.3, 115.0, 114.7, 59.7, 56.9, 55.5, 53.9, 46.5, 41.8, 38.3, 28.5, 15.6, 14.0. Anal. (C$_{26}$H$_{31}$N$_3$O$_4$; 1.5HCl; 1.2H$_2$O) C, H, N, Cl.

Example 118

Synthesis of (±)-syn-Ethyl 1-(2-(2,4-dioxo-1,2-dihydroquinazolin-3(4H),-yl)ethyl)-4-(4-isopropylphenyl) piperidine-3-carboxylate (Compound 5u)

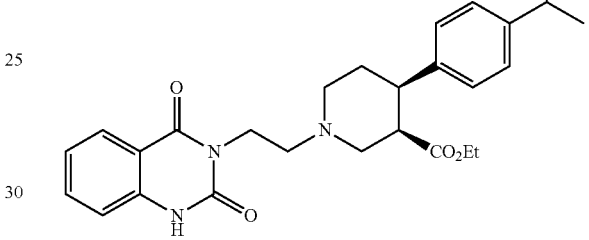

Compound 5u was prepared in 52% yield from 1a and 4u using the method of Example 98 above. MP(HCl)=153-154° C. $^1$H NMR (300 MHz, CDCl$_3$) δ 9.26 (br. s., 1H), 8.11 (d, J=7.7 Hz, 1H), 7.57 (t, J=7.4 Hz, 1H), 7.22-7.14 (m, 3H), 7.11 (d, J=8.0 Hz, 2H), 7.04 (d, J=7.7 Hz, 1H), 4.36-4.21 (m, 1H), 4.21-4.03 (m, 1H), 3.74 (q, J=7.1 Hz, 2H), 3.35 (d, J=12.4 Hz, 1H), 3.20 (d, J=9.4 Hz, 1H), 2.94 (br. s., 1H), 2.89-2.75 (m, 2H), 2.72 (t, J=6.2 Hz, 2H), 2.58 (d, J=11.8 Hz, 2H), 2.35-2.13 (m, 1H), 1.80 (d, J=11.0 Hz, 1H), 1.13-1.26 (m, J=6.6 Hz, 6H), 0.92 (t, J=6.9 Hz, 3H). $^{13}$C NMR (75 MHz, CDCl$_3$) δ 172.2, 162.3, 151.4, 146.5, 140.7, 138.5, 135.0, 128.5, 127.6, 126.1, 123.4, 114.7, 114.7, 59.7, 55.4, 53.9, 46.5, 41.9, 38.3, 33.7, 26.9, 24.1, 24.1, 14.0. Anal. (C$_{27}$H$_{33}$N$_3$O$_4$; 1.25HCl; 1.25H$_2$O) C, H, N.

Example 119

Synthesis of (±)-syn-Ethyl 1-(2-(2,4-dioxo-1,2-dihydroquinazolin-3(4H)-yl)ethyl)-4-phenethylpiperidine-3-carboxylate (Compound 5v)

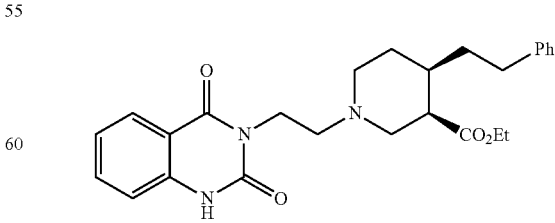

Compound 5v was prepared in 38% yield from 1a and 4v using the method of Example 98 above. MP(HCl)=140-141° C. $^1$H NMR (300 MHz, CDCl$_3$) δ 10.7 (br. s., 1H), 8.09 (dd, J=1.5, 8.1 Hz, 1H), 7.59 (ddd, J=1.6, 7.1, 8.3 Hz, 1H), 7.31-7.17 (comp., 4H), 7.17-7.06 (comp., 4H), 4.39-4.12 (broad m., 2H), 4.11-3.87 (broad m, 2H), 2.93-2.73 (broad m, 1H), 2.73-2.57 (broad m, 6H), 2.57-2.37 (broad m, 2H), 1.98-1.70 (broad m, 3H), 1.70-1.51 (m, 2H), 1.14 (t, J=7.15 Hz, 3H). $^{13}$C NMR (75 MHz, CDCl$_3$) δ 173.2, 162.4, 152.4, 142.3, 138.8, 135.0, 128.4, 128.3, 125.8, 123.3, 115.2, 114.7, 60.0, 55.7, 45.0, 38.3, 33.8, 28.1, 14.3. Anal. (C$_{26}$H$_{31}$N$_3$O$_4$; 1.5HCl; 0.25H$_2$O) C, H, N.

Example 120

Synthesis of (±)-syn-Ethyl 1-(2-(2,4-dioxo-1,2-dihydroquinazolin-3(4H)-yl)ethyl)-4-(2-fluorophenyl)piperidine-3-carboxylate (Compound 5x)

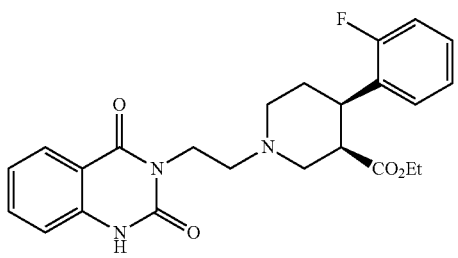 [SMILES: CCOC(=O)[C@H]1CN(CCn2c(=O)[nH]c3ccccc3c2=O)CC[C@H]1c1ccccc1F]

Compound 5x was prepared in 40% yield from 1a and 4x using the method of Example 98 above. MP=182.8-183.6° C. $^1$H NMR (300 MHz, CDCl$_3$) δ 9.98 (Br. S., 1H), 8.12 (dd, J=1.65, 7.98 Hz, 1H), 7.64-7.51 (m, 1H), 7.40-7.30 (m, 1H), 7.24-7.17 (m, 1H), 7.17-6.88 (m, 4H), 4.39-4.23 (m, 1H), 4.16 (dt, J=6.36, 12.86 Hz, 1H), 3.73 (q, J=7.15 Hz, 2H), 3.41 (d, J=10.73 Hz, 1H), 3.28 (d, J=10.46 Hz, 1H), 3.16-3.00 (m, 2H), 2.77-2.66 (m, 2H), 2.66-2.52 (m, 1H), 2.36-2.17 (m, 1H), 1.67 (d, J=11.01 Hz, 2H), 0.92 (t, J=7.15 Hz, 3H). $^{13}$C NMR (75 MHz, CDCl$_3$) δ 172.2, 162.6, 162.4, 159.4, 152.0, 138.7, 135.0, 130.2, 130.1, 129.7, 129.7, 129.7, 128.4, 127.7, 127.6, 123.6, 123.6, 123.6, 123.4, 115.0, 114.9, 114.9, 114.7, 114.6, 59.7, 57.2, 55.4, 54.1, 44.5, 38.3, 36.0, 26.0, 14.0. Anal. (C$_{24}$H$_{26}$N$_3$O$_4$F) C, H, N, F. MS (APCl, [M+H]$^+$, m/z) 440.2.

Example 121

Synthesis of (±)-syn-Ethyl 1-(2-(2,4-dioxo-1,2-dihydroquinazolin-3(4H),-yl)ethyl)-4-(m-tolyl)piperidine-3-carboxylate (Compound 5y)

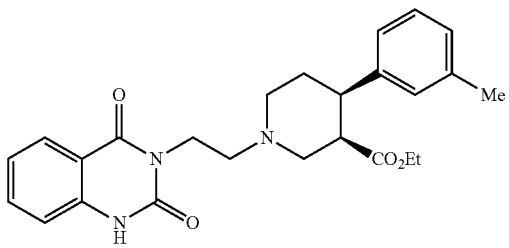 [SMILES: CCOC(=O)[C@H]1CN(CCn2c(=O)[nH]c3ccccc3c2=O)CC[C@H]1c1cccc(C)c1]

Compound 5y was prepared in 31% yield from 1a and 4y using the method of Example 98 above. MP(HCl)=148.5-150° C. $^1$H NMR (300 MHz, CDCl$_3$) δ 9.91 (br. s., 1H), 8.11 (dd, J=1.6, 8.0 Hz, 1H), 7.58 (ddd, J=1.4, 7.1, 8.3 Hz, 1H), 7.24-7.02 (m, 5H), 6.96 (d, J=7.2 Hz, 1H), 4.37-4.09 (m, 2H), 3.83-3.67 (m, 2H), 3.38 (dd, J=2.5, 11.0 Hz, 1H), 3.22 (d, J=11.8 Hz, 1H), 3.02-2.93 (m, 1H), 2.88-2.77 (m, 1H), 2.77-2.65 (m, 2H), 2.63-2.48 (m, 2H), 2.29 (s, 3H), 2.34-2.19 (m, 1H), 1.91-1.75 (m, 1H), 0.93 (t, J=7.2 Hz, 3H). $^{13}$C NMR (75 MHz, CDCl$_3$) δ 172.2, 162.4, 151.8, 143.3, 138.7, 137.4, 135.0, 128.6, 128.5, 127.9, 126.8, 124.7, 123.3, 115.0, 114.7, 59.7, 56.9, 55.5, 53.9, 46.4, 46.4, 42.1, 38.3, 21.6, 14.0. Anal. (C$_{25}$H$_{29}$N$_3$O$_4$; 1.9HCl; 0.1H$_2$O) C, H, N.

Example 122

Synthesis of (±)-syn-Ethyl 1-(2-(2,4-dioxo-1,2-dihydroquinazolin-3(4H),-yl)ethyl)-4-(o-tolyl)piperidine-3-carboxylate (Compound 5z)

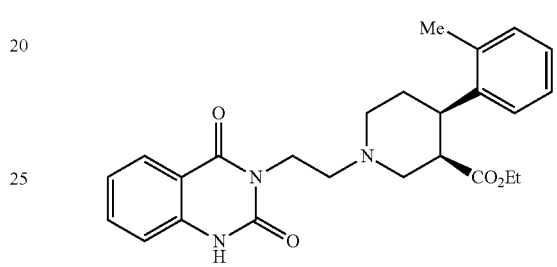

Compound 5z was prepared in 38% yield from 1a and 4z using the method of Example 98 above. MP(HCl)=174-175° C. $^1$H NMR (300 MHz, CDCl$_3$) δ 10.73 (br. s., 1H), 8.12 (dd, J=1.6, 8.0 Hz, 1H), 7.68-7.52 (m, 1H), 7.40-7.29 (m, 1H), 7.24-6.99 (m, 5H), 4.45-4.11 (m, 2H), 3.76 (dq, J=3.6, 7.1 Hz, 2H), 3.44 (d, J=11.6 Hz, 1H), 3.27 (d, J=11.6 Hz, 1H), 3.04-2.85 (m, 2H), 2.85-2.63 (m, 3H), 2.63-2.52 (m, 1H), 2.31 (s, 3H), 2.40-2.18 (m, 1H), 1.65 (d, J=14.6 Hz, 1H), 0.92 (t, J=7.2 Hz, 3H). $^{13}$C NMR (75 MHz, CDCl$_3$) δ 172.1, 162.4, 152.2, 140.9, 138.8, 135.6, 135.0, 130.2, 128.4, 128.3, 126.2, 125.7, 123.4, 115.2, 114.7, 59.7, 57.2, 55.6, 54.4, 44.0, 39.6, 38.3, 27.1, 19.4, 14.0. Anal. (C$_{25}$H$_{29}$N$_3$O$_4$; 1.6HCl; 1.0H$_2$O) C, H, N.

Example 123

Synthesis of (±)-syn-Ethyl 4-(3-(dimethylamino)phenyl)-1-(2-(2,4-dioxo-1,2-dihydroquinazolin-3(4H),-yl)ethyl) piperidine-3-carboxylate (Compound 5aa)

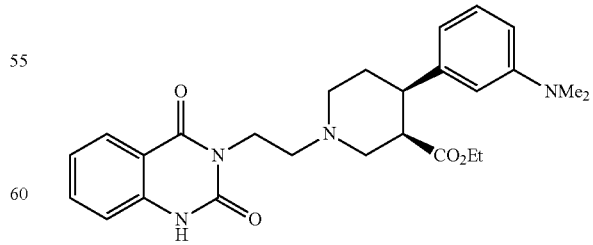

Compound 5aa was prepared in 30% yield from 1a and 4aa using the method of Example 98 above. MP(HCl)=179-180° C. $^1$H NMR (300 MHz, CDCl$_3$) δ 9.95 (s, 1H), 8.11 (dd, J=1.6, 8.0 Hz, 1H), 7.64-7.50 (m, 1H), 7.20 (t, J=7.4 Hz, 1H), 7.16-7.02 (m, 2H), 6.68-6.61 (m, 2H), 6.55 (dd, J=2.5, 7.2 Hz, 1H), 4.38-4.06 (m, 2H), 3.78 (qd, J=7.1, 2.1 Hz, 5H), 3.40 (dd, J=3.0, 12.7 Hz, 1H), 3.20 (d, J=11.01 Hz, 1H), 3.04-2.95 (m, 1H), 2.90 (s, 6H), 2.71 (dd, J=5.2, 7.7 Hz, 5H), 2.60 (dd, J=3.6, 11.3 Hz, 2H), 2.39-2.17 (m, 1H), 1.90-1.77 (m, 1H), 0.95 (t, J=7.0 Hz, 3H). $^{13}$C NMR (75 MHz, CDCl$_3$) δ 172.5, 162.5, 152.2, 150.5, 144.2, 138.9, 135.0, 128.7, 128.3, 123.3, 116.4, 115.2, 114.6, 112.5, 110.7, 59.8, 56.8, 55.6, 53.9, 46.4, 42.5, 40.8, 38.3, 27.3, 14.0. Anal. (C$_{26}$H$_{32}$N$_4$O$_4$; 3HCl; 2H$_2$O) C, H, N.

Example 124

Synthesis of (±)-syn-Ethyl 4-(2-(dimethylamino) phenyl)-1-(2-(2,4-dioxo-1,2-dihydroquinazolin-3 (4H),-yl)ethyl) piperidine-3-carboxylate (Compound 5bb)

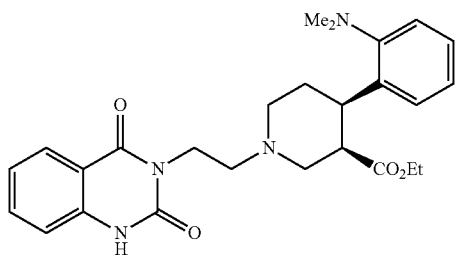 [SMILES: CCOC(=O)[C@H]1CN(CCn2c(=O)[nH]c3ccccc3c2=O)CC[C@H]1c1ccccc1N(C)C]

Compound 5bb was prepared in 48% yield from 1a and 5bb using the method of Example 98 above. MP(HCl)=208-209° C. $^1$H NMR (300 MHz, CDCl$_3$) δ 10.29 (s, 1H), 8.11 (dd, J=1.6, 8.0 Hz, 1H), 7.58 (ddd, J=1.6, 7.01, 8.3 Hz, 1H), 7.35 (d, J=7.7 Hz, 1H), 7.24-7.09 (m, 4H), 7.07-6.97 (m, 1H), 4.37-4.15 (m, 2H), 3.81-3.68 (m, 2H), 3.41 (dt, J=1.9, 8.5 Hz, 1H), 3.34-3.20 (m, 3H), 2.84-2.62 (m, 3H), 2.61 (s, 6H), 2.62-2.53 (m, 1H), 2.28 (tq, J=2.7, 11.3 Hz, 1H), 1.69-1.56 (m, 1H), 0.90 (t, J=7.2 Hz, 3H). $^{13}$C NMR (75 MHz, CDCl$_3$) δ 173.0, 162.5, 153.1, 152.2, 152.1, 139.1, 138.9, 135.0, 128.9, 128.3, 127.1, 124.3, 123.3, 121.0, 115.2, 114.7, 59.5, 57.3, 55.7, 54.6, 46.1, 46.1, 44.6, 38.3, 37.6, 26.8, 14.0. Anal. (C$_{26}$H$_{32}$N$_4$O$_4$; 2HCl; 2.75H$_2$O) C, H, N, Cl.

Example 125

Synthesis of (±)-syn-Ethyl 4-(3-azidophenyl)-1-(2-(2,4-dioxo-1,2-dihydroquinazolin-3(4H)-yl)ethyl) piperidine-3-carboxylate (Compound 5cc)

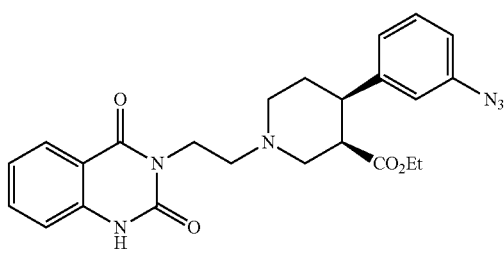 [SMILES: CCOC(=O)[C@H]1CN(CCn2c(=O)[nH]c3ccccc3c2=O)CC[C@H]1c1cccc(N=[N+]=[N-])c1]

To a cooled solution (0° C.) of 5qq (below) (70 mg, 0.16 mmol) in water (2 ml) was added conc. HCl (0.3 mL). The solution was stirred for 5 minutes at 0° C. then NaNO$_2$ was added in 1 ml of water. The cooling bath was removed and the solution was stirred for 1 hr. The reaction mixture was cooled back to 0° C. and NaN$_3$ in 1 mL of water was added to the mixture. Once again, the cooling bath was removed and the solution was stirred for 1 hr at which time the reaction was quenched by the addition of sat. NaHCO$_3$, until pH=8. The mixture was then extracted with CH$_2$Cl$_2$ (3×20 mL), dried over Na$_2$SO$_4$ and concentrated to afford pure compound 5cc in 81% yield as an off-white foam. MP(HCl)=178-179° C. $^1$H NMR (300 MHz, CDCl$_3$) δ 10.23 (br. s., 1H), 8.11 (dd, J=1.65, 7.98 Hz, 1H), 7.59 (ddd, J=1.51, 7.22, 8.32 Hz, 1H), 7.16-7.24 (m, 2H), 6.99-7.12 (m, 2H), 6.90 (t, J=2.20 Hz, 1H), 6.79-6.87 (m, 1H), 4.09-4.37 (m, 2H), 3.69-3.81 (m, 2H), 3.40 (dd, J=2.20, 11.28 Hz, 1H), 3.23 (d, J=11.28 Hz, 1H), 2.97 (q, J=4.04 Hz, 1H), 2.82 (dt, J=4.13, 11.83 Hz, 1H), 2.71 (t, J=6.88 Hz, 2H), 2.48-2.65 (m, 2H), 2.26 (td, J=2.89, 11.08 Hz, 1H), 1.81 (dd, J=3.03, 12.66 Hz, 1H), 0.95 (t, J=7.15 Hz, 3H). $^{13}$C NMR (75 MHz, CDCl$_3$) δ Anal. (C$_{26}$H$_{32}$N$_4$O$_4$; 2HCl; 2.75H$_2$O) C, H, N, Cl.

Example 126

Synthesis of (±)-syn-Ethyl 4-(3,4-dimethoxyphenyl)-1-(2-(2,4-dioxo-1,2-dihydroquinazolin-3(4H),-yl)ethyl) piperidine-3-carboxylate (Compound 5dd)

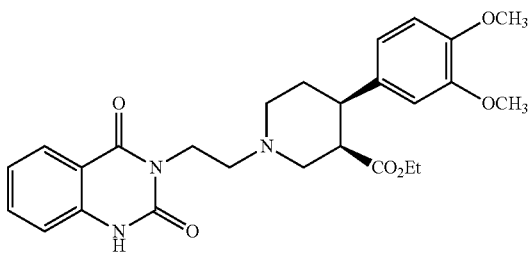 [SMILES: CCOC(=O)[C@H]1CN(CCn2c(=O)[nH]c3ccccc3c2=O)CC[C@H]1c1ccc(OC)c(OC)c1]

Compound 5dd was prepared in 48% yield from 1a and 4dd using the method of Example 98 above. MP(HCl)=154.5-155.5° C. $^1$H NMR (300 MHz, CDCl$_3$) δ 10.15 (br. s., 1H), 8.11 (d, J=8.0 Hz, 1H), 7.58 (t, J=8.0 Hz, 1H), 7.24-7.14 (t, J=7.7 Hz, 1H), 7.09 (d, J=8.3 Hz, 1H), 6.91-6.65 (m, 3H), 4.44-4.09 (m, 1H), 3.83 (s, 6H), 3.99-3.66 (m, 2H), 3.37 (d, J=9.9 Hz, 1H), 3.20 (d, J=11.3 Hz, 1H), 2.95 (br. s., 1H), 2.82 (d, J=10.5 Hz, 1H), 2.77-2.67 (m, 2H), 2.67-2.45 (m, 2H), 2.41-2.17 (m, 1H), 1.82 (d, J=10.7 Hz, 1H), 0.96 (t, J=7.02 Hz, 3H). $^{13}$C NMR (75 MHz, CDCl$_3$) ∞ 172.4, 162.4, 152.1, 148.5, 147.3, 138.8, 136.1, 135.0, 128.4, 123.4, 119.7, 115.1, 114.7, 111.3, 110.8, 59.8, 56.8, 55.9, 55.9, 55.5, 53.9, 46.5, 41.8, 38.3, 27.3, 14.1. Anal. (C$_{26}$H$_{31}$N$_3$O$_6$; 3HCl; 2H$_2$O) C, H, N.

Example 127

Synthesis of (±)-syn-Ethyl 4-(3,4-dihydroxyphenyl)-1-(2-(2,4-dioxo-1,2-dihydroquinazolin-3(4H)-yl)ethyl)piperidine-3-carboxylate (Compound 5ff)

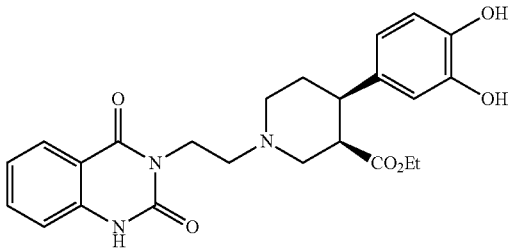 [SMILES: CCOC(=O)[C@H]1CN(CCn2c(=O)[nH]c3ccccc3c2=O)CC[C@H]1c1ccc(O)c(O)c1]

Compound 5ff was prepared in 56% yield from 1a and 4ff using the method of Example 98 above. MP(HCl)=167-168.5° C. $^1$H NMR (300 MHz, DMSO-d$_6$) δ 7.92 (dd, J=8.0, 1.7 Hz, 1H), 7.64 (td, J=7.7, 1.7 Hz, 1H), 7.24-7.12 (m, 2H), 6.65 (d, J=2.2 Hz, 1H), 6.59 (m, J=8.0 Hz, 1H), 6.50 (td, J=8.3, 1.9 Hz, 10H), 4.14-3.89 (m, 2H), 3.76-3.59 (m, 1H), 3.15 (dd, J=10.5, 3.9 Hz, 1H), 3.02 (m, J=11.0 Hz, 1H), 2.94-2.81 (m, 1H), 2.71-2.57 (m, 1H), 2.45-2.25 (m, 2H), 2.12 (t, J=9.1 Hz, 12H), 1.63 (d, J=13.5 Hz, 1H), 0.91 (t, J=7.2 Hz, 3H). $^{13}$C NMR (75 MHz, DMSO-d$_6$) δ 171.9, 162.4, 150.7, 145.0, 143.7, 140.0, 135.4, 134.9, 127.9, 123.0, 118.7, 115.6, 115.5, 114.3, 59.4, 56.8, 55.4, 54.0, 46.2, 37.9, 27.0, 14.4. Anal. ($C_{24}H_{27}N_3O_6$; 1HCl; 2.5$H_2O$) C, H, N.

Example 128

Synthesis of (±)-syn-Ethyl 4-(2,3-dihydrobenzo[b][1,4]dioxin-6-yl)-1-(2-(2,4-dioxo-1,2-dihydroquinazolin-3(4H)-yl)ethyl)piperidine-3-carboxylate (Compound 5gg)

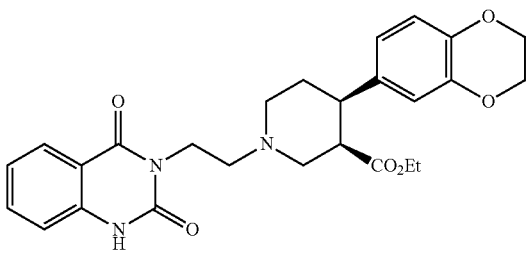 [SMILES: CCOC(=O)[C@H]1CN(CCn2c(=O)[nH]c3ccccc3c2=O)CC[C@H]1c1ccc2c(c1)OCCO2]

Compound 5gg was prepared in 46% yield from 1a and 4gg using the method of Example 98 above. MP(HCl)=178-179° C. $^1$H NMR (300 MHz, CDCl$_3$) δ 9.55 (s, 1H), 8.11 (dd, J=8.0, 1.7 Hz, 1H), 7.58 (ddd, J=8.3, 7.2, 1.7 Hz, 1H), 7.21 (dt, J=7.2, 0.8 Hz, 1H), 7.05 (d, J=8.0 Hz, 1H), 6.83-6.65 (m, 3H), 4.34-4.21 (m, 1H), 4.20 (s, 4H), 4.19-4.10 (m, 1H), 3.78 (q, J=7.1 Hz, 2H), 3.34 (dd, J=11.0, 3.3 Hz, 1H), 3.19 (d, J=11.3 Hz, 1H), 2.91 (q, J=3.6 Hz, 1H), 2.83-2.62 (m, 3H), 2.61-2.40 (m, 2H), 2.26 (td, J=10.7, 2.5 Hz, 1H), 1.77 (dd, J=12.4, 3.3 Hz, 1H), 0.97 (t, J=7.2 Hz, 3H). $^{13}$C NMR (75 MHz, CDCl$_3$) δ 172.3, 162.5, 152.2, 143.0, 141.8, 138.9, 136.7, 135.0, 128.3, 123.3, 120.6, 116.7, 116.6, 115.2, 114.6, 64.4, 59.8, 56.6, 55.5, 53.8, 46.4, 41.3, 38.2, 27.2, 14.1. Anal. ($C_{26}H_{29}N_3O_6$; 1HCl; 2.2$H_2O$) C, H, N.

Example 129

Synthesis of Ethyl 1-(2-(2,4-dioxo-1,2-dihydroquinazolin-3(4H)-yl)ethyl)-4-(2-(trifluoromethyl)phenyl)-1,2,5,6-tetrahydropyridine-3-carboxylate (Compound 5hh)

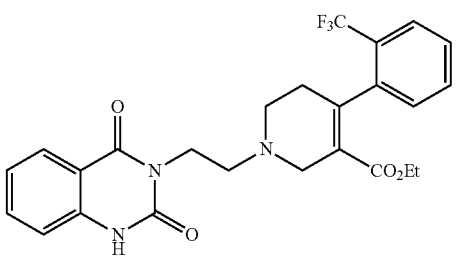 [SMILES: CCOC(=O)C1=C(c2ccccc2C(F)(F)F)CCN(CCn2c(=O)[nH]c3ccccc3c2=O)C1]

Compound 5hh was prepared in 21% yield from 1a and 4hh using the method of Example 98 above. MP(HCl)=153.5-154.5° C. $^1$H NMR (300 MHz, CDCl$_3$) δ 10.01 (br. s., 1H), 8.10 (dd, J=8.0, 1.7 Hz, 1H), 7.60 (td, J=8.0, 1.4 Hz, 2H), 7.47 (t, J=8.0 Hz, 1H), 7.35 (m, J=7.7, 7.7 Hz, 1H), 7.22 (t, J=8.3 Hz, 1H), 7.14-7.04 (m, 2H), 4.46-4.22 (m, 2H), 3.83 (q, J=7.1 Hz, 2H), 3.64 (d, J=16.8 Hz, 1H), 3.37 (dt, J=16.5, 3.0 Hz, 1H), 3.11-2.76 (m, 2H), 2.72-2.58 (m, 1H), 2.53-2.41 (m, 2H), 0.79 (t, J=7.0 Hz, 3H). $^{13}$C NMR (75 MHz, CDCl$_3$) δ 165.6, 162.6, 152.1, 145.8, 138.8, 135.1, 131.5, 128.5, 128.3, 126.9, 126.6, 126.2, 126.1, 126.0, 123.4, 115.2, 114.6, 60.1, 54.8, 52.9, 49.1, 38.1, 34.5, 13.5. Anal. ($C_{25}H_{24}F_3N_3O_4$; 1.3HCl; 1.1$H_2O$) C, H, N.

Example 130

Synthesis of (±)-syn-ethyl 1-(2-(2,4-dioxo-1,2-dihydroquinazolin-3(4H)-yl)ethyl)-4-(4-(trifluoromethoxy)phenyl)piperidine-3-carboxylate (Compound 5ii)

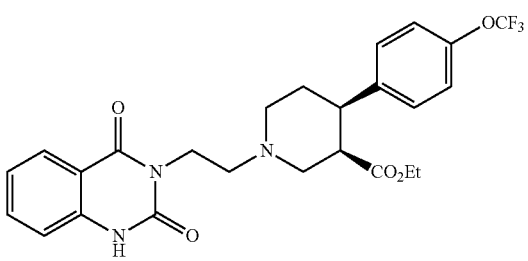 [SMILES: CCOC(=O)[C@H]1CN(CCn2c(=O)[nH]c3ccccc3c2=O)CC[C@H]1c1ccc(OC(F)(F)F)cc1]

Compound 5ii was prepared in 51% yield from 1a and 4ll using the method of Example 98 above. MP(HCl)=150-151.5° C. $^1$H NMR (300 MHz, CDCl$_3$) δ 10.02 (s, 1H), 8.16-8.04 (m, 1H), 7.59 (dt, J=8.3, 1.4 Hz, 1H), 7.32-7.17 (m, 4H), 7.09 (d, J=8.3 Hz, 3H), 4.39-4.24 (m, 1H), 4.23-4.06 (m, 1H), 3.74 (q, J=7.1 Hz, 2H), 3.39 (dd, J=10.5, 3.6 Hz, 1H), 3.23 (d, J=11.0 Hz, 1H), 3.02-2.89 (m, 1H), 2.83 (dt, J=11.8, 4.1 Hz, 1H), 2.71 (t, J=6.9 Hz, 2H), 2.58 (qd, J=11.8, 3.6 Hz, 2H), 2.25 (td, J=10.7, 2.8 Hz, 1H), 1.80 (dd, J=12.7, 2.8 Hz, 1H), 0.92 (t, J=7.2 Hz, 3H). $^{13}$C NMR (75 MHz, CDCl$_3$) δ 172.0, 162.4, 152.1, 147.5, 147.5, 142.2, 138.8, 135.0, 129.0, 128.4, 123.4, 122.3, 120.5, 118.9, 115.1, 114.7, 59.9, 56.9, 55.4, 53.8, 46.4, 41.7, 38.2, 26.8, 13.9. Anal. (C$_{25}$H$_{26}$F$_3$N$_3$O$_5$; 1.3HCl; 1.1H$_2$O) C, H, N.

Example 131

Synthesis of (±)-syn-Ethyl 1-(2-(2,4-dioxo-1,2-dihydroquinazolin-3(4H)-yl)ethyl)-4-(3-(trifluoromethoxy)phenyl)piperidine-3-carboxylate (Compound 5jj)

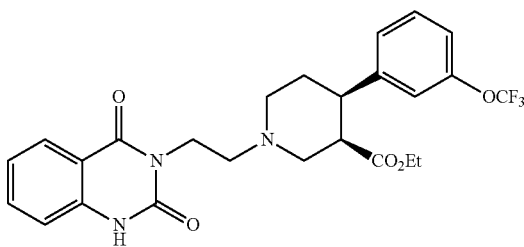 [SMILES: CCOC(=O)[C@H]1CN(CCn2c(=O)[nH]c3ccccc3c2=O)CC[C@H]1c1cccc(OC(F)(F)F)c1]

Compound 5jj was prepared in 64% yield from 1a and 4jj using the method of Example 98 above. MP(HCl)=155-156° C. $^1$H NMR (300 MHz, CDCl$_3$) δ 10.32 (br. s., 1H), 8.12 (dd, J=8.0, 1.7 Hz, 1H), 7.59 (td, J=8.3, 1.4 Hz, 1H), 7.25-7.15 (m, 2H), 7.14-7.05 (m, 2H), 7.01 (td, J=8.0, 1.1 Hz, 1H), 4.39-4.13 (m, 2H), 3.75 (q, J=7.2 Hz, 2H), 3.40 (dd, J=11.4, 2.1 Hz, 1H), 3.24 (m, J=11.0, 0.8 Hz, 1H), 2.97 (q, J=3.6 Hz, 1H), 2.85 (dt, J=11.5, 4.0 Hz, 1H), 2.72 (t, J=6.9 Hz, 2H), 2.65-2.44 (m, 2H), 2.26 (td, J=11.0, 2.2 Hz, 1H), 1.89-1.76 (m, 2H), 0.92 (t, J=7.0 Hz, 3H). $^{13}$C NMR (75 MHz, CDCl$_3$) □ 171.9, 162.4, 152.0, 149.2, 149.1, 145.9, 138.7, 135.0, 129.2, 128.4, 126.1, 123.4, 120.4, 118.5, 115.0, 114.7, 59.9, 56.9, 55.4, 53.7, 46.3, 41.8, 38.3, 26.7, 13.9. Anal. (C$_{25}$H$_{26}$F$_3$N$_3$O$_5$; 1HCl; 1.5H$_2$O) C, H, N.

Example 132

Synthesis of (±)-syn-Ethyl 1-(2-(2,4-dioxo-1,2-dihydroquinazolin-3(4H)-yl)ethyl)-4-(pyridin-4-yl)piperidine-3-carboxylate (Compound syn-5kk)

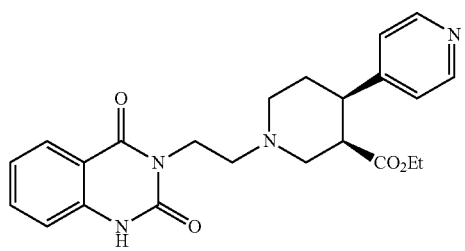 [SMILES: CCOC(=O)[C@H]1CN(CCn2c(=O)[nH]c3ccccc3c2=O)CC[C@H]1c1ccncc1]

Compound syn-5kk was prepared in 23% yield from 1a and 4kk using the method of Example 98 above. MP(HCl) =210-211° C. $^1$H NMR (300 MHz, CDCl$_3$) δ 8.48 (d, J=5.8 Hz, 2H), 8.12 (dt, J=7.8, 0.9 Hz, 1H), 7.64-7.52 (m, 1H), 7.22 (d, J=7.7 Hz, 1H), 7.18 (d, J=6.3 Hz, 2H), 7.07 (d, J=8.0 Hz, 1H), 4.40-4.23 (m, 1H), 4.23-4.04 (m, 1H), 3.71 (q, J=7.1 Hz, 2H), 3.40 (d, J=12.1 Hz, 1H), 3.25 (d, J=11.3 Hz, 1H), 3.07-2.94 (m, 1H), 2.86-2.75 (m, 1H), 2.75-2.65 (m, 2H), 2.57 (ddd, J=12.4, 11.6, 3.0 Hz, 2H), 2.24 (m, J=10.7, 10.7, 2.5 Hz, 1H), 1.84 (dd, J=13.5, 3.6 Hz, 1H), 0.91 (t, J=7.2 Hz, 3H). $^{13}$C NMR (75 MHz, CDCl$_3$) δ 171.6, 162.4, 152.7, 151.9, 149.4, 138.9, 135.0, 128.4, 123.3, 123.0, 115.0, 114.6, 60.0, 57.1, 55.3, 53.4, 45.7, 41.3, 38.2, 26.0, 13.9. Anal. (C$_{23}$H$_{26}$N$_4$O$_4$; 2HCl; 2H$_2$O) C, H, N.

Example 133

Synthesis of (±)-anti-Ethyl 1-(2-(2,4-dioxo-1,2-dihydroquinazolin-3(4H)-yl)ethyl)-4-(pyridin-4-yl)piperidine-3-carboxylate (Compound anti-5kk)

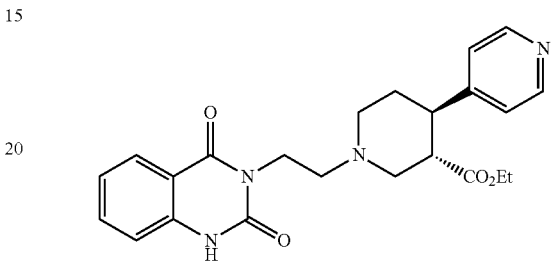

The title compound was isolated from the reaction of 1a and 4kk using the method of Example 98 above in 5% yield. $^1$H NMR (300 MHz, CDCl$_3$) δ 9.45 (s, 1H), 8.49 (dd, J=4.7, 1.4 Hz, 2H), 8.14 (dd, J=8.1, 1.5 Hz, 1H), 7.62 (ddd, J=8.3, 7.2, 1.7 Hz, 1H), 7.29-7.22 (m, 4H), 7.12 (m, J=4.4, 1.7 Hz, 2H), 7.07 (d, J=8.0 Hz, 1H), 4.36-4.18 (m, 1H), 4.13 (q, J=7.0 Hz, 1H), 3.33 (d, J=7.7 Hz, 1H), 3.22 (d, J=11.8 Hz, 1H), 2.93-2.68 (m, 3H), 2.39-2.15 (m, 4H), 1.79 (dd, J=8.4, 3.2 Hz, 2H), 1.65-1.52 (m, 4H), 0.98 (t, J=7.0 Hz, 3H). $^{13}$C NMR (75 MHz, CDCl$_3$) δ 172.8, 162.4, 152.7, 151.5, 149.9, 138.6, 135.2, 128.6, 123.5, 123.0, 114.8, 114.7, 60.5, 58.9, 56.3, 55.3, 53.5, 48.3, 44.6, 38.3, 32.7, 30.7, 23.5, 23.2, 22.3, 14.7, 14.0. Purity determined by LC/MS.

Example 134

Synthesis of (±)-syn-Ethyl 4-(4-aminophenyl)-1-(2-(2,4-dioxo-1,2-dihydroquinazolin-3(4H),-yl)ethyl) piperidine-3-carboxylate (Compound 5mm)

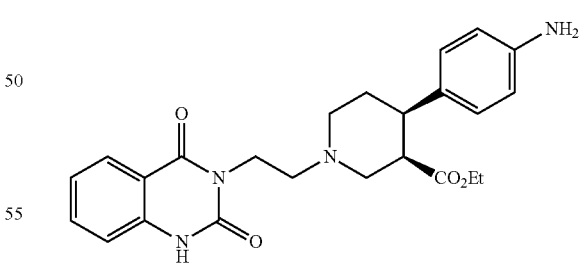

The title compound was prepared in 93% yield from 5s (above) by the following procedure: A flask containing magnetic stir bar and carbamate 5s was cooled to 0° C. and charged with trifluoroacetic acid (TFA). The flask was removed from the ice-bath and stirred for 30 min at 0° C., before concentrating to remove excess TFA. The residue was placed under high vacuum overnight to provide the pure product. MP(HCl)=263.5-265° C. $^1$H NMR (300 MHz, DMSO-d$_6$) δ 11.40 (s, 1H), 7.91 (dd, J=1.1, 8.0 Hz, 1H), 7.65 (dt, J=7.7, 1.4 Hz, 1H), 7.11-7.26 (m, 2H), 6.90 (d, J=8.26 Hz, 2H), 6.43 (d, J=8.53 Hz, 2H), 4.15-3.98 (m, 1H), 3.98-3.86 (m, 1H), 3.79-3.58 (m, 2H), 3.14 (dd, J=2.2, 11.8 Hz, 1H), 3.02 (d, J=11.3 Hz, 1H), 2.86 (d, J=3.6 Hz, 1H), 2.69-2.57 (m, 1H), 2.45-2.29 (m, 2H), 2.19-2.06 (m, 1H), 1.61 (dd, J=2.7, 12.1 Hz, 1H), 0.90 (t, J=7.0 Hz, 3H). $^{13}$C NMR (75 MHz, DMSO-$d_6$) δ 172.0, 162.4, 150.7, 147.0, 140.0, 135.4, 131.0, 128.4, 127.9, 123.0, 115.6, 114.3, 114.0, 59.4, 56.8, 55.4, 54.0, 46.3, 37.9, 27.0, 14.4. Anal. ($C_{24}H_{28}N_4O_4$; 2.1HCl; 2.3$H_2O$) C, H, N.

Example 135

Synthesis of (±)-Syn-Ethyl 1-(2-(2,4-dioxo-3,4-dihydroquinazolin-1(2H)-yl)ethyl)-4-(3,4-dichlorophenyl) piperidine-3-carboxylate (Compound syn-5nn) and (±)-Anti-Ethyl 1-(2-(2,4-dioxo-3,4-dihydroquinazolin-1(2H)-yl)ethyl)-4-(3,4-dichlorophenyl) piperidine-3-carboxylate (Compound anti-5nn)

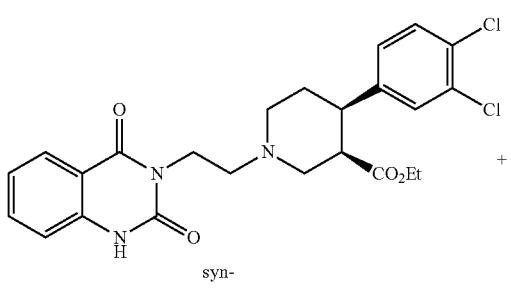 [SMILES: CCOC(=O)[C@H]1CN(CCn2c(=O)[nH]c3ccccc3c2=O)CC[C@H]1c1ccc(Cl)c(Cl)c1]

Compounds syn-5nn and anti-5nn were produced according to the following method:

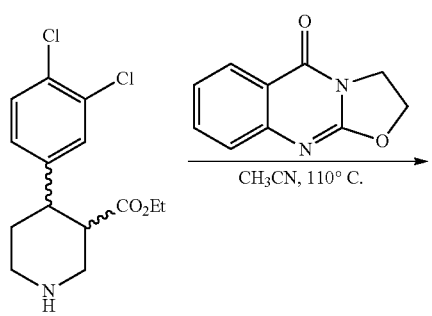

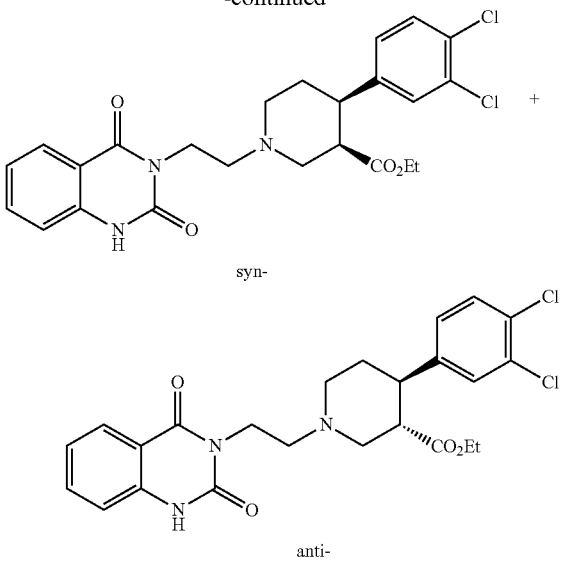

The diasteromers were separated by prep-TLC eluting with 1% MeOH/CHCl$_3$ (20 mg/plate, 3-5 elutions per plate).

Syn-5nn:
Isolated 11 mg (15% impurity of anti-)$^1$H NMR (300 MHz, CDCl$_3$) δ ppm 9.46 (s, 1H), 8.11 (dd, J=8.0, 1.7 Hz, 1H), 7.64-7.54-(m, 1H), 7.35-7.17 (m, 6H), 7.12-6.99 (m, 2H), 4.37-4.21 (m, 1H), 4.21-4.06 (m, 1H), 3.73 (q, J=7.0 Hz, 2H), 3.43-3.29 (m, 1H), 3.24 (d, J=13.5 Hz, 1H), 2.99-2.85 (m, 1H), 2.81-2.62 (m, 3H), 2.61-2.44 (m, 2H), 2.30-2.14 (m, 1H), 1.84-1.68 (m, 1H), 0.94 (t, J=7.0 Hz, 3H). $^{13}$C NMR (76 MHz, CDCl$_3$) δ 171.7, 162.3, 151.5, 143.9, 138.6, 135.1, 135.0, 132.0, 129.9, 129.9, 128.5, 127.2, 123.4, 114.8, 114.6, 114.6, 60.0, 57.1, 55.3, 53.6, 46.3, 41.5, 38.2, 26.5, 14.0. MP(HCl salt)=144-146° C.

Anti-5nn:
Isolated 20 mg pure. $^1$H NMR (300 MHz, CDCl$_3$) δ ppm 9.50 (s, 1H), 8.13 (dd, J=8.0, 1.7 Hz, 1H), 7.69-7.54 (m, 1H), 7.38-7.17 (m, 3H), 7.11-6.94 (m, 2H), 4.40-4.13 (m, 2H), 3.91 (qd, J=7.2, 1.7 Hz, 7H), 3.25 (dd, J=29.2, 11.3 Hz, 6H), 2.85-2.63 (m, 4H), 2.39-2.14 (m, 2H), 1.85-1.65 (m, 2H), 1.00 (t, J=7.2 Hz, 3H). $^{13}$C NMR (75 MHz, CHLOROFORM-d) δ 172.9, 162.4, 152.1, 144.0, 138.7, 135.2, 132.3, 130.5, 130.4, 129.6, 128.5, 127.0, 123.6, 115.1, 114.7, 60.5, 56.4, 55.3, 53.6, 48.9, 44.5, 38.3, 33.0, 14.1.

Example 136

Synthesis of (±) syn-ethyl 4-(4-chlorophenyl)-1-(2-(2,4-dioxo-1,2-dihydroquinazolin-3(4H)-yl)ethyl) piperidine-3-carboxylate (Compound 5oo)

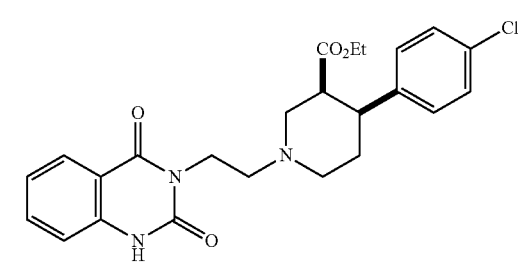 [SMILES: CCOC(=O)[C@@H]1CN(CCn2c(=O)[nH]c3ccccc3c2=O)CC[C@@H]1c1ccc(Cl)cc1]

Compound 5oo was prepared from 4oo and 1a as a white solid (118 mg, 38%) using the method of Example 98 above. mp=194.8-196.1° C.; $^1$H NMR (300 MHz, CDCl$_3$) δ 9.39 (br. s, 1H), 8.12 (d, J=6.6 Hz, 1H), 7.61-7.56 (m, 1H), 7.20 (dd, J=11.4, 9.0 Hz, 4H), 7.04 (d, J=8.1 Hz, 1H), 4.34-4.24 (m, 1H), 4.19-4.10 (m, 1H), 3.73 (q, J=7.2 Hz, 2H), 3.37 (d, J=9.3 Hz, 1H), 3.26-3.19 (m, 1H), 2.92 (q, J=3.3 Hz, 1H), 2.79 (dt, J=4.2, 12.0 Hz, 1H), 2.70 (t, J=6.6 Hz, 2H), 2.62-2.49 (comp, 2H), 2.25 (dt, J=2.7, 10.5 Hz, 1H), 1.81-1.74 (m, 1H), 0.93 (t, J=7.2 Hz, 3H); $^{13}$C NMR (75 MHz, CDCl$_3$) δ 171.9, 162.3, 151.5, 142.0, 138.6, 135.0, 131.8, 129.1, 128.5, 128.1, 123.4, 114.8, 114.7, 59.8, 57.0, 55.4, 53.7, 46.4, 41.7, 38.3, 26.7, 14.0; Anal. Calcd for C$_{24}$H$_{26}$ClN$_3$O$_4$: C, 63.22; H, 5.75; N, 9.22; Cl, 7.78. Found: C, 63.25; H, 5.83; N, 9.25; Cl, 7.54.

Example 137

Synthesis of (±) syn-ethyl 4-(3-chlorophenyl)-1-(2-(2,4-dioxo-1,2-dihydroquinazolin-3(4H)-yl)ethyl)piperidine-3-carboxylate (Compound 5pp)

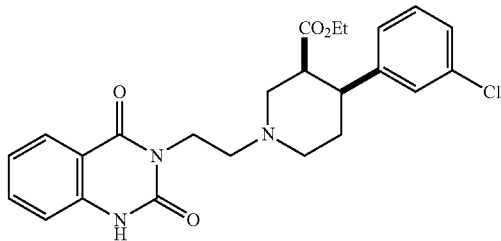 [SMILES: CCOC(=O)[C@@H]1CN(CCn2c(=O)[nH]c3ccccc3c2=O)CC[C@@H]1c1cccc(Cl)c1]

Compound 5pp was prepared from 4pp and 1a as a white solid (93 mg, 27%) using the method of Example 98 above. mp=161.8-162.9° C.; $^1$H NMR (300 MHz, CDCl$_3$) δ 8.89 (br. s, 1H), 8.12 (dd, J=1.5, 6.6 Hz, 1H), 7.62-7.56 (m, 1H), 7.26-7.02 (comp, 4H), 7.01 (d, J=8.1 Hz, 1H), 4.32-4.24 (m, 1H), 4.18-4.09 (m, 1H), 3.72 (q, J=7.2 Hz, 2H), 3.37 (d, J=11.1 Hz, 1H), 3.25-3.22 (m, 1H), 2.93 (q, J=3.3 Hz, 1H), 2.78 (dt, J=4.2, 12.0 Hz, 1H), 2.70 (t, J=6.9 Hz, 2H), 2.61-2.50 (comp, 2H), 2.22 (dt, J=2.7, 10.8 Hz, 1H), 1.83-1.78 (m, 1H), 0.93 (t, J=7.2 Hz, 3H); $^{13}$C NMR (75 MHz, CDCl$_3$) δ 171.9, 162.3, 151.5, 145.6, 138.6, 135.0, 133.9, 129.2, 128.5, 128.0, 126.2, 125.9, 123.4, 114.8, 114.7, 59.9, 57.0, 55.3, 53.7, 46.3, 41.9, 38.2, 16.6, 14.0; Anal. Calcd for C$_{24}$H$_{26}$ClN$_3$O$_4$: C, 63.22; H, 5.75; N, 9.22; Cl, 7.78. Found: C, 63.11; H, 5.94; N, 9.04; Cl, 7.53.

Example 138

Synthesis of (±)-syn-Ethyl 4-(3-((tert-butoxycarbonyl)amino)phenyl)-1-(2-(2,4-dioxo-1,2-dihydroquinazolin-3(4H)-yl)ethyl)piperidine-3-carboxylate (Compound 5qq)

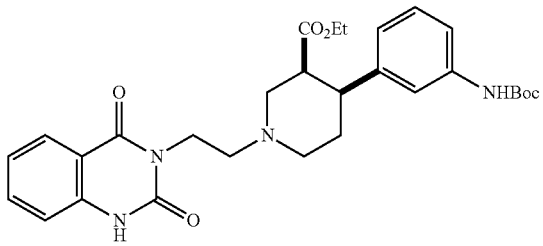 [SMILES: CCOC(=O)[C@@H]1CN(CCn2c(=O)[nH]c3ccccc3c2=O)CC[C@@H]1c1cccc(NC(=O)OC(C)(C)C)c1]

Compound 5qq was prepared from 4qq and 1a as a white solid (199 mg, 88%) using the method of Example 98 above. $^1$H NMR (300 MHz, CDCl$_3$) δ 10.09 (br. s., 1H), 8.11 (dd, J=1.65, 7.98 Hz, 1H), 7.62-7.52 (m, 1H), 7.24-7.10 (m, 4H), 7.08 (d, J=7.98 Hz, 1H), 6.92 (d, J=7.15 Hz, 1H), 4.37-4.15 (m, 1H), 4.11 (q, J=7.15 Hz, 2H), 3.80-3.67 (m, 2H), 3.37 (dd, J=2.06, 11.14 Hz, 1H), 3.21 (d, J=10.46 Hz, 1H), 3.01-2.90 (m, 1H), 2.88-2.75 (m, 1H), 2.71 (t, J=6.88 Hz, 2H), 2.56 (ddd, J=0.83, 2.75, 11.28 Hz, 2H), 2.31-2.17 (m, 1H), 1.78 (d, J=11.28 Hz, 1H), 1.50 (s, 8H), 1.25 (t, J=7.15 Hz, 3H), 0.93 (t, J=7.15 Hz, 3H).

Example 139

Synthesis of (±) syn-ethyl 1-(2-(2,4-dioxo-1,2-dihydroquinazolin-3(4H)-yl)ethyl)-4-(1H-pyrrol-2-yl)piperidine-3-carboxylate (Compound 5rr)

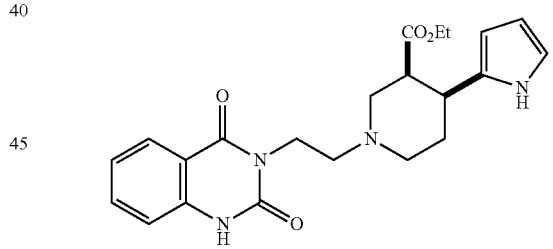

Silica gel (1.07 g) was added to a solution of 5k (95 mg, 0.19 mmol) in CH$_2$Cl$_2$ (4 mL). The solvent was evaporated at room temperature, and the residue was heated to 55° C. in a vacuum oven (2 mmHg) for 4 days. The silicagel was cooled to room temperature, and EtOAc (5 mL) was added. The mixture was filtered through a filter paper washing thoroughly with EtOAc (20 mL). The combined filtrate and washings were concentrated and dried under vacuum to give 5rr (41 mg, 52%) as an off-white solid: mp=202.0° C. (December); $^1$H NMR (300 MHz, CDCl$_3$) δ 9.05 (br. s, 1H), 8.80 (br. s, 1H), 8.12 (d, J=7.2 Hz, 1H), 7.57 (dt, J=0.9, 7.5 Hz, 1H), 7.23 (t, J=7.5 Hz, 1H), 7.03 (d, J=7.8 Hz, 1H), 6.65 (m, 1H), 6.05 (dd, J=2.7, 5.7, 1H), 5.93 (br. s, 1H), 4.30-4.21 (m, 1H), 4.17-4.08 (m, 1H), 3.95-3.84 (m, 2H), 3.26-3.22 (m, 1H), 3.11-3.07 (m, 1H), 2.99-2.95 (m, 1H), 2.81 (dd, J=4.2, 8.1 Hz, 1H), 2.68 (t, J=6.9 Hz, 2H), 2.59 (dd, J=2.7, 12.0 Hz, 1H), 2.51-2.28 (comp, 2H), 1.75-1.69 (m, 1H), 1.07

(t, J=7.2 Hz, 3H); $^1$H NMR (75 MHz, CDCl$_3$) δ 174.2, 162.4, 151.8, 138.6, 135.1, 133.7, 128.5, 123.5, 116.9, 114.9, 114.7, 107.4, 106.2, 60.4, 56.8, 55.5, 53.6, 46.5, 38.3, 36.9, 29.1, 14.1; Anal. Calcd for C$_{22}$H$_{26}$N$_4$O$_4$.0.25H$_2$O. 0.08EtOAc: C, 63.52; H, 6.38; N, 13.65. Found: C, 63.67; H, 6.38; N, 13.18; MS (APCl, [M+H]$^+$, m/z) 411.2.

Example 140

Synthesis of (±)-syn-Ethyl 4-(3,4-difluorophenyl)-1-(2-(2,4-dioxo-1,2-dihydroquinazolin-3(4H)-yl)ethyl)piperidine-3-carboxylate (Compound 5ss)

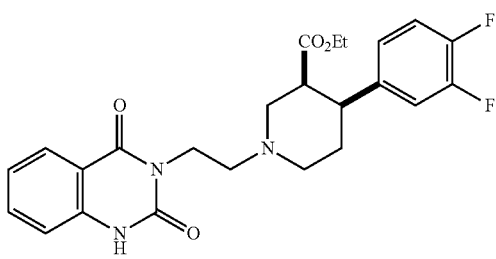 [SMILES: CCOC(=O)[C@@H]1CN(CCn2c(=O)[nH]c3ccccc3c2=O)CC[C@@H]1c1ccc(F)c(F)c1]

Compound 5ss was prepared from 4ss and 1a as a white solid (54% yield) using the method of Example 98 above. MP=196.6-198.4° C. $^1$H NMR (300 MHz, CDCl$_3$) δ 9.80 (Br. S. 1H), 8.11 (dd, J=1.65, 7.98 Hz, 1H), 7.64-7.52 (m, 1H), 7.27-7.17 (t, J=7.71 Hz, 2H), 7.12-6.89 (m, 4H), 4.37-4.077 (m, 2H), 3.75 (q, J=7.15 Hz, 2H), 3.45-3.34 (d, J=11.28 Hz, 1H), 3.23 (d, J=11.56 Hz, 1H), 2.95-2.88 (m, 1H), 2.86-2.65 (m, 3H), 2.62-2.44 (m, 2H), 2.23 (t, J=11.01 Hz, 3H), 1.77 (d, J=11.56 Hz, 1H), 0.95 (t, J=7.15 Hz, 3H). $^{13}$C NMR (75 MHz, CDCl$_3$) δ 171.8, 162.4, 151.8, 140.6, 138.7, 135.0, 128.5, 123.5, 123.4, 116.8, 116.7, 116.5, 116.5, 116.5, 114.9, 114.7, 59.9, 57.0, 55.3, 53.7, 46.4, 41.5, 38.2, 26.8, 14.0. Anal. (C$_{24}$H$_{25}$F$_2$N$_3$O$_4$) C, H, N, F. MS (APCl, [M+H]$^+$, m/z) 458.2.

Example 141

Synthesis of (±)-syn-Ethyl 4-(4-nitrophenyl)-1-(2-(2,4-dioxo-1,2-dihydroquinazolin-3(4H)-yl)ethyl)piperidine-3-carboxylate (Compound 5tt)

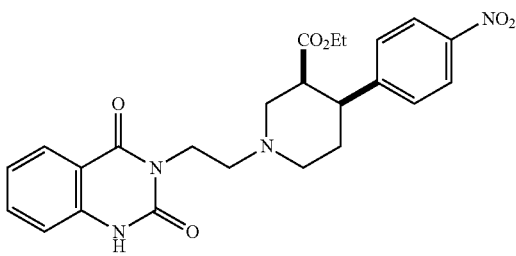 [SMILES: CCOC(=O)[C@@H]1CN(CCn2c(=O)[nH]c3ccccc3c2=O)CC[C@@H]1c1ccc([N+](=O)[O-])cc1]

Compound 5tt was prepared from 4tt and 1a as a white solid (60% yield) using the method of Example 98 above. MP=216-217.4° C. $^1$H NMR (300 MHz, CDCl$_3$) δ 8.84 (s, 1H), 8.17-8.03 (m, 3H), 7.65-7.49 (m, 1H), 7.48-7.36 (m, 2H), 7.26-7.12 (m, 2H), 7.02 (d, J=7.98 Hz, 1H), 4.43-4.20 (m, 1H), 4.20-4.03 (m, 1H), 3.69 (q, J=6.97 Hz, 2H), 3.43 (d, J=11.01 Hz, 1H), 3.29 (d, J=11.28 Hz, 1H), 3.03-2.95 (m, 1H), 2.89 (dt, J=3.89, 11.76 Hz, 1H), 2.79-2.51 (m, 4H), 2.24 (td, J=2.75, 11.28 Hz, 1H), 1.85 (dd, J=2.20, 12.66 Hz, 1H), 0.92 (t, J=7.15 Hz, 3H). $^{13}$C NMR (75 MHz, CDCl$_3$) δ 171.5, 162.3, 151.5, 146.4, 138.5, 135.0, 128.6, 128.5, 123.5, 123.3, 114.8, 114.7, 60.0, 57.3, 55.2, 53.6, 46.3, 42.2, 38.2, 26.3, 14.0. Anal. (C$_{24}$H$_{26}$N$_4$O$_6$) C, H, N. MS (APCl, [M+H]$^+$, m/z) 467.2.

Example 142

Synthesis of (±)-syn-Ethyl 1-(3-(2,4-dioxo-1,2-dihydroquinazolin-3(4H)-yl)propyl)-4-(4-fluorophenyl)piperidine-3-carboxylate

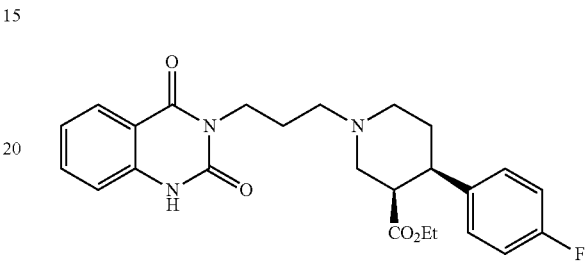

The compound was prepared from 4d and 3-(3-chloropropyl)quinazoline-2,4(1H,3H)-dione (Chem J W et al, J Het Chem 25, 1103-1105 (1988); incorporated by reference herein) as a white solid (54% yield) using the method of Example 98 above. MP=171.8-172.4° C. $^1$H NMR (300 MHz, CDCl$_3$) δ 9.27 (s, 1H), 8.13 (dd, J=1.65, 7.98 Hz, 1H), 7.65-7.54 (m, 1H), 7.29-7.18 (m, 4H), 7.07 (d, J=7.98 Hz, 1H), 6.95 (t, J=8.81 Hz, 2H), 4.17-3.87 (m, 4H), 3.39-3.23 (m, 1H), 3.04 (d, J=10.46 Hz, 1H), 2.99-2.90 (m, 1H), 2.83 (dt, J=4.02, 11.76 Hz, 1H), 2.66-2.34 (m, 4H), 2.15 (td, J=3.16, 11.08 Hz, 1H), 2.00-1.83 (m, 2H), 1.79 (d, J=12.38 Hz, 1H), 1.06 (t, J=7.15 Hz, 3H). $^{13}$C NMR (75 MHz, CDCl$_3$) δ 172.3, 163.0, 162.4, 159.7, 152.0, 139.1, 139.1, 139.1, 138.6, 135.0, 129.2, 129.2, 129.2, 129.1, 128.5, 123.4, 115.0, 114.9, 114.7, 114.6, 60.0, 56.1, 55.9, 53.9, 46.4, 41.7, 39.6, 27.0, 25.3, 14.2 Anal. (C$_{25}$H$_{28}$FN$_3$O$_4$) C, H, N. MS (APCl, [M+H]$^+$, m/z) 454.2.

Example 143

Synthesis of (±)-syn-Ethyl 1-(4-(2,4-dioxo-1,2-dihydroquinazolin-3(4H)-yl)butyl)-4-(4-fluorophenyl)piperidine-3-carboxylate

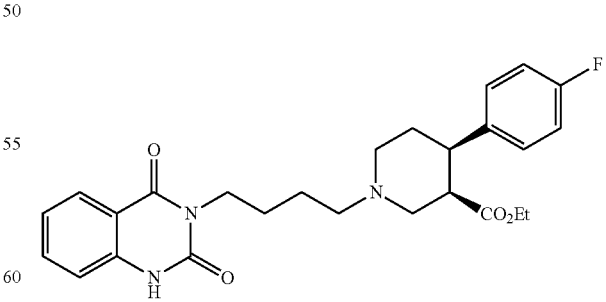

The compound was prepared from 4d and 3-(3-chlorobutyl)quinazoline-2,4(1H,3H)-dione (Chem et al, 1988 supra) as a white solid (40% yield) using the general procedure described above. MP=148.5-149.7° C. $^1$H NMR (300 MHz, CDCl$_3$) δ 9.27 (s, 1H), 8.13 (dd, J=1.65, 7.98 Hz, 1H), 7.65-7.54 (m, 1H), 7.29-7.18 (m, 4H), 7.07 (d, J=7.98 Hz, 1H), 6.95 (t, J=8.81 Hz, 2H), 4.17-3.87 (m, 4H), 3.39-3.23 (m, 1H), 3.04 (d, J=10.46 Hz, 1H), 2.99-2.90 (m, 1H), 2.83 (dt, J=4.02, 11.76 Hz, 1H), 2.66-2.34 (m, 4H), 2.15 (td, J=3.16, 11.08 Hz, 1H), 2.00-1.83 (m, 2H), 1.79 (d, J=12.38 Hz, 1H), 1.06 (t, J=7.15 Hz, 3H). $^{13}$C NMR (75 MHz, CDCl$_3$) δ 172.3, 163.0, 162.4, 159.7, 152.0, 139.1, 139.1, 139.1, 138.6, 135.0, 129.2, 129.2, 129.2, 129.1, 128.5, 123.4, 115.0, 114.9, 114.7, 114.6, 60.0, 56.1, 55.9, 53.9, 46.4, 41.7, 39.6, 27.0, 25.3, 14.2 Anal. (C$_{26}$H$_{30}$FN$_3$O$_4$) C, H, N, F. MS (APCI, [M+H]$^+$, m/z) 454.2.

Example 144

Synthesis of (±)-syn-Ethyl 1-(2-(1,3-dioxoisoindolin-2-yl)ethyl)-4-(4-fluorophenyl)piperidine-3-carboxylate

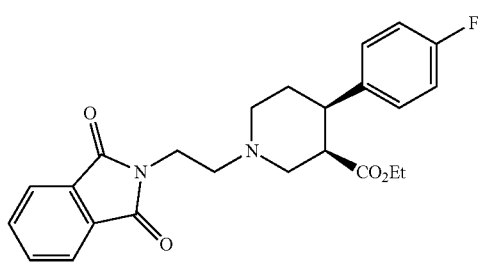 [SMILES: CCOC(=O)[C@H]1CN(CCN2C(=O)c3ccccc3C2=O)CC[C@H]1c1ccc(F)cc1]

The compound was prepared according to the general procedure above in 57% yield from 4d and N-(2-Bromoethyl)phthalimide. MP(HCl)=104.5-105.5° C. $^1$H NMR (300 MHz, CDCl$_3$) δ 7.85-7.80 (m, 2H), 7.71-7.66 (m, 2H), 7.22 (dd, J=8.3, 5.8 Hz, 7H), 6.93 (t, J=8.8 Hz, 2H), 3.92-3.70 (m, 2H), 3.63 (td, J=7.3, 3.6 Hz, 2H), 3.27 (ddd, J=11.4, 3.5, 1.9 Hz, 1H), 3.21-3.10 (m, 1H), 2.93-2.84 (m, 1H), 2.78 (dt, J=11.8, 4.2 Hz, 1H), 2.65 (ddd, J=7.4, 5.7, 2.1 Hz, 2H), 2.51 (dd, J=11.0, 3.3 Hz, 2H), 2.18 (td, J=10.9, 2.9 Hz, 1H), 1.87-1.70 (m, 2H), 0.92 (t, J=7.2 Hz, 3H). $^{13}$C NMR (75 MHz, CDCl$_3$) δ 171.8, 168.4, 162.9, 159.7, 139.1, 139.0, 133.9, 132.3, 129.2, 129.1, 123.2, 114.9, 114.6, 59.7, 56.9, 55.6, 53.4, 46.5, 41.6, 35.4, 26.7, 14.0. Anal. (C$_{24}$H$_{25}$FN$_2$O$_4$; 1 HCl; 1.3H$_2$O) C, H, N.

Example 145

Synthesis of (±)-syn-Ethyl 1-(2-(6-bromo-2,4-dioxo-1,2-dihydroquinazolin-3(4H)-yl)ethyl)-4-(4-fluorophenyl) piperidine-3-carboxylate

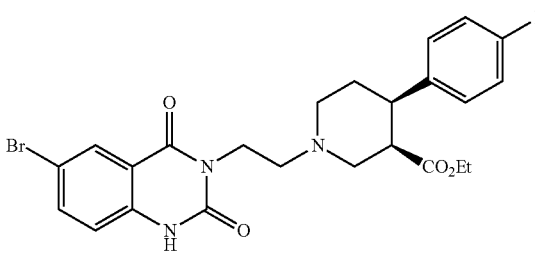

The compound was prepared in 51% yield from 4d and 1c. MP(HCl salt)=167-168° C. $^1$H NMR (300 MHz, CDCl$_3$) δ 8.21 (br. s., 1H), 7.64 (dd, J=2.48, 8.53 Hz, 1H), 7.23-7.11 (m, 2H), 7.06-6.84 (m, 3H), 4.35-4.08 (m, 2H), 3.74 (q, J=7.15 Hz, 2H), 3.44-3.29 (m, 1H), 3.27-3.11 (m, 1H), 2.98-2.87 (m, 1H), 2.82 (dt, J=4.09, 11.63 Hz, 1H), 2.76-2.63 (m, 2H), 2.63-2.44 (m, 2H), 2.24 (td, J=2.20, 11.01 Hz, 1H), 1.78 (dd, J=3.58, 12.11 Hz, 1H), 0.94 (t, J=7.15 Hz, 3H). $^{13}$C NMR (76 MHz, CDCl$_3$) δ 172.2, 163.0, 161.2, 159.7, 151.8, 138.9, 138.9, 138.9, 137.8, 137.7, 130.9, 129.1, 129.1, 129.0, 129.0, 116.9, 116.1, 116.0, 114.9, 114.7, 77.5, 77.3, 77.1, 76.7, 59.9, 56.7, 55.3, 53.8, 46.5, 41.5, 38.4, 26.9, 14.0. Anal. (C$_{24}$H$_{25}$FN$_3$O$_4$; 1HCl; 1.25H$_2$O) C, H, N.

Example 146

Synthesis of (±)-syn-Ethyl 1-(2-(6,8-dibromo-2,4-dioxo-1,2-dihydroquinazolin-3(4H)-yl)ethyl)-4-(4-fluorophenyl) piperidine-3-carboxylate

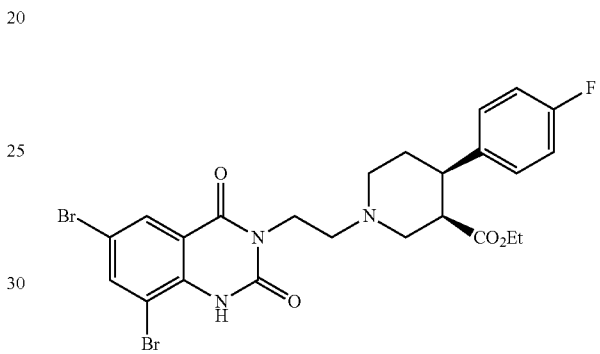

The title compound was prepared in 58% yield from 4d and 1d. $^1$H NMR (300 MHz, CDCl$_3$) δ 8.21 (d, J=2.20 Hz, 1H), 8.05 (s, 1H), 7.91 (d, J=2.20 Hz, 1H), 7.24-7.14 (m, 2H), 6.94 (t, J=8.67 Hz, 2H), 4.31-4.02 (m, 2H), 3.86-3.66 (m, 2H), 3.31 (ddd, J=1.79, 3.51, 11.49 Hz, 1H), 3.22-3.08 (m, 1H), 2.90 (t, J=3.85, Hz, 1H), 2.80 (dt, J=4.13, 12.11 Hz, 4H), 2.67 (t, J=6.74 Hz, 2H), 2.42-2.61 (m, 2H), 2.22 (td, J=2.75, 11.01 Hz, 1H), 1.78 (dd, J=3.44, 12.80 Hz, 1H), 0.97 (t, J=7.15 Hz, 3H). $^{13}$C NMR (76 MHz, CDCl$_3$) δ 171.9, 162.9, 160.4, 159.7, 149.4, 139.8, 139.1, 139.0, 139.0, 135.6, 130.8, 129.2, 129.1, 129.1, 117.0, 115.7, 114.9, 114.6, 109.1, 59.7, 56.8, 55.1, 53.7, 46.5, 41.6, 38.7, 26.9, 14.0.

Example 147

General Synthesis of Compounds of Series 6 from Compounds of Series 5

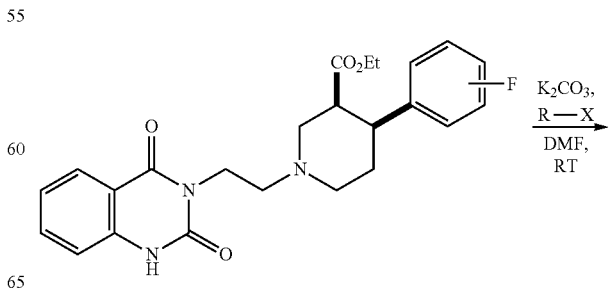

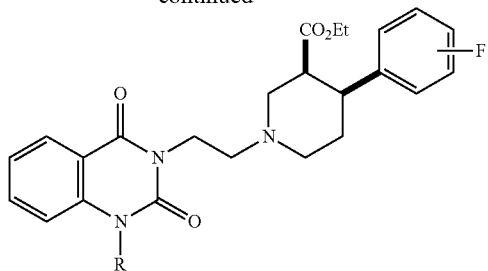

Anhydrous K₂CO₃ (0.43 mmol) and alkyl halide (0.2 mmol) were added to a solution of 5 (0.15 mmol) in anhydrous DMF (1.5 mL). The resulting mixture was stirred at room temperature for 2 h, and EtOAc (8 mL) and water (3 mL) were added. The organic layer was separated, dried (Na₂SO₄), and concentrated. The residue was purified by flash chromatography eluting with 80% EtOAc/hexanes (1% Et₃N, 1% MeOH) to give 6.

Example 148

Synthesis of (±) syn-ethyl 4-(4-fluorophenyl)-1-(2-(1-methyl-2,4-dioxo-1,2-dihydroquinazolin-3(4H)-yl)ethyl)piperidine-3-carboxylate (Compound 6a)

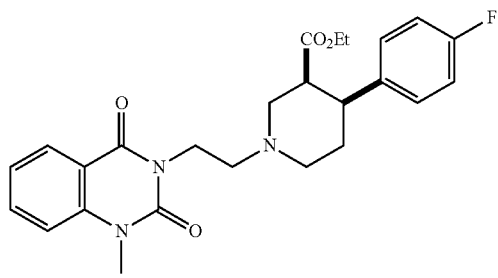 [SMILES: CCOC(=O)[C@@H]1CN(CCn2c(=O)c3ccccc3n(C)c2=O)CC[C@@H]1c1ccc(F)cc1]

Compound 6a was prepared according to the method of Example 147 above from 5d and methyl iodide in 93% yield. mp=131.1-133.0° C.; ¹H NMR (300 MHz, CDCl₃) δ 8.21 (dd, J=1.8, 8.1 Hz, 1H), 7.66 (ddd, J=1.8, 7.2, 8.4 Hz, 1H), 7.27-7.20 (comp, 4H), 6.94 (t, J=8.7 Hz, 2H), 4.32-4.13 (m, 2H), 3.72 (q, J=7.2 Hz, 2H), 3.61 (s, 3H), 3.37 (d, J=11.4 Hz, 1H), 3.21 (d, J=10.8 Hz, 1H), 2.90 (dd, J=3.6, 4.8 Hz, 1H), 2.80 (dt, J=3.9, 11.7 Hz, 1H), 2.70-2.65 (m, 2H), 2.62-2.52 (comp, 2H), 2.23 (dt, J=2.7, 10.8 Hz, 1H), 1.79 (dd, J=3.3, 12.6 Hz, 1H), 0.94 (t, J=7.2 Hz, 3H); ¹³C NMR (75 MHz, CDCl₃) δ 171.9, 161.8, 161.3 (d, J=242.2 Hz), 151.1, 140.7, 139.2, 135.1, 129.2 (d, J=7.4 Hz), 128.9, 122.9, 115.6, 114.7 (d, J=21.2 Hz), 113.6, 59.7, 57.0, 55.3, 53.9, 46.5, 41.7, 39.1, 30.8, 26.8, 14.0; Anal. Calcd for C₂₅H₂₈FN₃O₄: C, 66.21; H, 6.22; F, 4.19; N, 9.27. Found: C, 66.14; H, 6.30; F, 4.04; N, 9.15; MS (APCl, [M+H]⁺, m/z) 454.2.

Example 149

Synthesis of (±) syn-ethyl 1-(2-(2,4-dioxo-1-propyl-1,2-dihydroquinazolin-3(4H)-yl)ethyl)-4-(4-fluorophenyl)piperidine-3-carboxylate (Compound 6b)

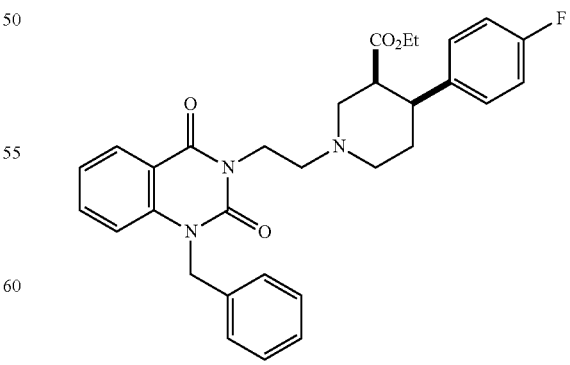

Compound 6b was prepared according to the method of Example 147 above using 5d and 1-bromopropane in 67% yield.: mp=96.8-97.7° C.; Rf=0.42 (80% EtOAc/hexanes, 1% Et₃N, 1% MeOH); ¹H NMR (300 MHz, CDCl₃) δ 8.20 (dd, J=1.5, 7.5 Hz, 1H), 7.64 (ddd, J=1.2, 7.5, 8.4 Hz, 1H), 7.27-7.15 (comp, 4H), 6.94 (t, J=8.7 Hz, 2H), 4.33-4.10 (m, 2H), 4.1-4.04 (m, 2H), 3.74 (dq, J=1.2, 7.2 Hz, 2H), 3.41-3.34 (m, 1H), 3.20 (d, J=11.7 Hz, 1H), 2.90 (q, J=3.3 Hz, 1H), 2.79 (dt, J=3.6, 11.1, 1H), 2.68 (t, J=7.2 Hz, 2H), 2.60-2.51 (comp, 2H), 2.25 (dt, J=3.3, 11.1 Hz, 1H), 1.83-1.71 (m, 2H), 1.04 (t, J=7.5 Hz, 3H), 0.95 (t, J=7.2 Hz, 3H); ¹³C NMR (75 MHz, CDCl₃) δ 171.9, 161.8, 161.3 (d, J=241.0), 150.9, 140.0, 139.2, 135.0, 129.2, 122.7, 115.8, 114.8 (d, J=20.6 Hz), 113.6, 59.7, 56.9, 55.3, 53.8, 46.5, 45.4, 41.7, 39.0, 26.9, 20.7, 14.0, 11.3; Anal. Calcd for C₂₇H₃₂FN₃O₄: C, 67.34; H, 6.70; F, 3.95; N, 8.73. Found: C, 67.57; H, 6.66; F, 3.81; N, 8.69; MS (APCl, [M+H]⁺, m/z) 482.2.

Example 150

Synthesis of (±) syn-ethyl 1-(2-(1-benzyl-2,4-dioxo-1,2-dihydroquinazolin-3(4H)-yl)ethyl)-4-(4-fluorophenyl)piperidine-3-carboxylate (Compound 6c)

Compound 6c was prepared according to the method of Example 147 above using 5d and benzyl bromide in 46% yield.: mp=134.9-136.4° C.; Rf=0.61 (80% EtOAc/hexanes, 1% Et₃N, 1% MeOH); $^1$H NMR (300 MHz, CDCl₃) δ 8.20 (d, J=7.8 Hz, 1H), 7.50 (dt, J=1.2, 7.2 Hz, 1H), 7.37-7.17 (comp, 3H), 7.08 (d, J=8.4 Hz, 1H), 6.95 (t, J=9.0 Hz, 2H), 5.37 (dd, J=16.8, 25.5 Hz, 2H), 4.39-4.32 (m, 1H), 4.27-4.20 (m, 1H), 3.70 (q, J=7.2 Hz, 2H), 3.36 (d, J=11.4 Hz, 1H), 3.23 (d, J=10.2 Hz, 1H), 2.91 (d, J=3.6 Hz, 1H), 2.81-2.71 (comp, 3H), 2.63-2.50 (comb, 2H), 2.26 (dt, J=3.3, 8.1 Hz, 1H), 1.78 (dd, J=3.3, 9.9 Hz, 1H), 0.91 (t, J=7.2 Hz, 3H); $^{13}$C NMR (75 MHz, CDCl₃) δ 172.0, 161.8, 161.3 (d, J=241.6 Hz), 151.5, 140.1, 139.2, 135.8, 135.0, 129.2, 129.1, 127.7, 126.5, 123.0, 115.8, 114.9, 114.5 (d, J=12.0 Hz), 59.7, 57.0, 55.3, 53.7, 47.5, 46.5, 41.6, 39.2, 26.9, 14.0; Anal. Calcd for C₃₁H₃₂FN₃O₄: C, 70.30; H, 6.09; N, 7.93. Found: C, 70.17; H, 6.10; N, 7.74; MS (APCl, [M+H]⁺, m/z) 530.2.

Binding Data:

| hVMAT2 [³H]DTBZ Ki (nM) ± SEM | hVMAT2 5HT Uptake IC₅₀ (nM) ± SEM | 5-HT1A [³H] 8—OH DPAT Ki(nM) ± SEM | 5-HT2A [¹²⁵I]DOI Ki (nM) ± SEM |
|---|---|---|---|
| >7 μM | 270 ± 53 | ND | ND |

Example 151

(±)-syn Ethyl 4-(3-fluorophenyl)-1-(2-(1-methyl-2,4-dioxo-1,2-dihydroquinazolin-3(4H)-yl)ethyl)piperidine-3-carboxylate (Compound 6d)

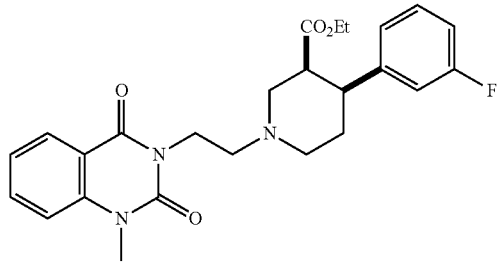 [SMILES: CCOC(=O)[C@@H]1CN(CCn2c(=O)c3ccccc3n(C)c2=O)CC[C@@H]1c1cccc(F)c1]

| hVMAT2 [³H]DTBZ Ki (nM) ± SEM | hVMAT2 5HT Uptake IC₅₀ (nM) ± SEM | 5-HT1A [³H] 8—OH DPAT Ki(nM) ± SEM | 5-HT2A [¹²⁵I]DOI Ki (nM) ± SEM |
|---|---|---|---|
| >9 μM | 89 ± 12 | >10 μM | ND |

Compound 6d was prepared according to the method of Example 147 above using 5e and methyl iodide in 67% yield.: mp=101.2-102.5° C.; Rf=0.32 (80% EtOAc/hexanes, 1% Et₃N, 1% MeOH); $^1$H NMR (300 MHz, CDCl₃) δ 8.20 (dd, J=1.5, 7.8 Hz, 1H), 1.65 (ddd, J=1.5, 6.9, 8.4 Hz, 1H), 7.27-7.17 (comp, 3H), 7.06-6.97 (comp, 2H), 6.85 (dt, J=2.7, 7.8 Hz, 1H), 4.35-4.25 (m, 1H), 4.22-4.13 (m, 1H), 3.72 (q, J=7.2 Hz, 2H), 3.60 (s, 3H), 3.41-3.35 (m, 1H), 3.22 (d, J=11.1 Hz, 1H), 2.95 (q, J=3.3 Hz, 1H), 2.81 (dt, J=3.6, 12.3 Hz, 1H), 2.68 (t, J=6.9 Hz, 2H), 2.60-2.53 (comp, 2H), 2.24 (dt, J=3.0, 11.1 Hz, 1H), 1.81 (dd, J=3.3, 12.9 Hz, 1H), 0.94 (t, J=7.2 Hz, 3H); NMR (75 MHz, CDCl₃) δ 171.8, 162.8 (d, J=242.8 Hz), 161.8, 151.1, 146.2 (d, J=6.9 Hz), 140.7, 135.1, 129.2 (d, J=8.0 Hz), 129.0, 123.3, 122.9, 115.7, 114.7 (d, J=21.2 Hz), 113.6, 112.8 (d, J=21.2 Hz), 59.7, 57.0, 55.3, 53.7, 46.3, 41.9, 39.1, 30.8, 26.6, 14.0; Anal. Calcd for C₂₅H₂₈FN₃O₄: C, 66.21; H, 6.22; F, 4.19; N, 9.27. Found: C, 66.04; H, 6.32; F, 4.09; N, 9.22; MS (APCl, [M+H]⁺, m/z) 454.2.

Example 152

Synthesis of (±)-syn-ethyl 1-(2-(1-methyl-2,4-dioxo-1,2-dihydroquinazolin-3(4H)-yl)ethyl)-4-(thiophen-2-yl)piperidine-3-carboxylate (Compound 6e)

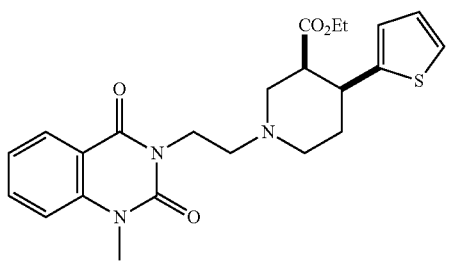 [SMILES: CCOC(=O)[C@@H]1CN(CCn2c(=O)c3ccccc3n(C)c2=O)CC[C@@H]1c1cccs1]

The title compound was prepared from 5m as a white solid (43 mg, 79%) using the method of Example 147 above. mp=99.5-100.7° C.; Rf=0.44 (80% EtOAc/hexanes, 1% Et₃N, 1% MeOH); $^1$H NMR (300 MHz, CDCl₃) δ 8.20 (dd, J=1.5, 7.8 Hz, 1H), 7.66 (ddd, J=1.8, 6.9, 8.7 Hz, 1H), 7.28-7.23 (m, 1H), 7.18 (d, J=8.4 Hz, 1H), 7.11 (dd, J=1.2, 5.1 Hz, 1H), 6.89 (dd, J=3.6, 4.8 Hz, 1H), 6.86-6.84 (m, 1H), 4.31-4.17 (m, 2H), 3.84 (q, J=7.2 Hz, 2H), 3.60 (s, 3H), 3.35 (br. s, 1H), 3.11 (dd, J=6.0, 11.1 Hz, 1H), 2.99-2.94 (comp, 2H), 2.77-2.65 (comp, 3H), 2.54-2.44 (m, 1H), 2.42-2.30 (m, 1H), 2.02-1.91 (m, 1H), 1.68 (br. s, 1H), 1.02 (t, J=7.2 Hz, 3H); $^{13}$C NMR (75 MHz, CDCl₃) δ 172.0, 161.8, 151.1, 146.5, 140.7, 135.1, 129.0, 126.4, 124.4, 123.2, 122.9, 115.6, 113.6, 60.0, 55.5, 54.5, 52.1, 46.5, 39.1, 37.7, 30.8, 29.8, 14.1; Anal. Calcd for C₂₃H₂₇N₃O₄S: C, 62.56; H, 6.16; S, 7.26; N, 9.52. Found: C, 62.38; H, 6.17; S, 7.19; N, 9.58; MS (APCl, [M+H]⁺, m/z) 442.2.

Example 153

Synthesis of Compounds of Series 7

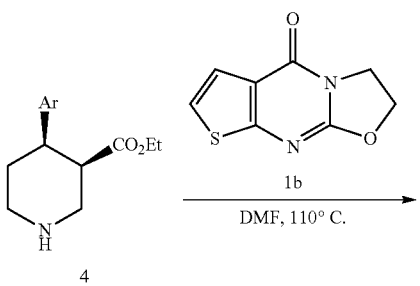

-continued

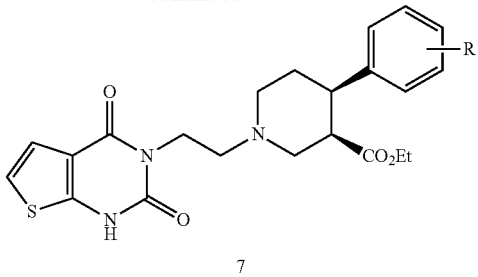

7

A 25 mL high-pressure tube was charged with compound 4 (118 mg, 0.47 mmol), 1b (91 mg, 0.47 mmol), anhydrous DMF (1 mL), and anhydrous 1,4-dioxane (1 mL). The tube was sealed and heated to 90° C. for 20 h. The mixture was concentrated and the residue was purified by flash chromatography eluting with 80% EtOAc/hexanes (1% MeOH, 1% Et3N) to give 7.

Example 154

Synthesis of (±) syn-ethyl 1-(2-(2,4-dioxo-1,2-dihydrothieno[2,3-d]pyrimidin-3(4H)-yl)ethyl)-4-(4-fluorophenyl)piperidine-3-carboxylate (Compound 7a)

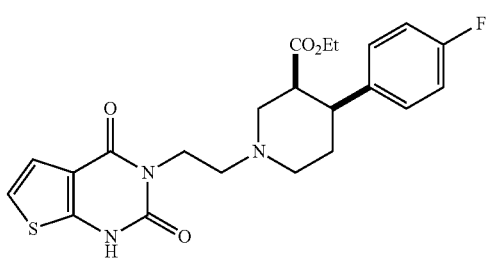 [SMILES: CCOC(=O)[C@@H]1CN(CCn2c(=O)[nH]c3sccc3c2=O)CC[C@@H]1c1ccc(F)cc1]

Compound 7a was prepared from Compound 4d (122 mg, 57%) as an off-white solid using the method of Example 153 above. mp=198.8-201.4° C.; $R_f$=0.10 (80% EtOAc/hexanes, 1% MeOH, 1% Et$_3$N); $^1$H NMR (300 MHz, CDCl$_3$) δ 7.27-7.19 (comp, 3H), 6.93 (t, J=8.7 Hz, 2H), 6.77 (d, J=5.7 Hz, 1H), 4.28-4.19 (m, 1H), 4.15-4.06 (m, 1H), 3.77 (q, J=7.2 Hz, 2H), 3.35 (dd, J=3.3, 10.5 Hz, 1H), 3.23 (d, J=11.7 Hz, 1H), 2.92 (d, J=3.3 Hz, 1H), 2.81 (dt, J=3.9, 11.4 Hz, 1H), 2.70 (t, J=6.9 Hz, 2H), 2.60-2.55 (comp, 2H), 2.24 (dt, J=3.6, 11.7 Hz, 1H), 1.80 (dd, J=3.0, 12.3 Hz, 1H), 0.97 (t, J=7.2 Hz, 3H); $^{13}$C NMR (75 MHz, CDCl$_3$) δ 172.2, 161.2 (d, J=242.2 Hz), 158.8, 151.9, 149.5, 139.1, 129.1 (d, J=7.4 Hz), 123.4, 116.1, 115.9, 114.7 (d, J=20.6 Hz), 59.9, 56.9, 55.4, 53.6, 46.5, 41.5, 38.1, 26.9, 14.0; Anal. Calcd for C$_{22}$H$_{24}$FN$_3$O$_4$S: C, 59.31; H, 5.43; N, 9.43; S, 7.20; F, 4.26. Found: C, 59.38; H, 5.49; N, 9.20; S, 7.00; F, 4.01; MS (APCl, [M+H]$^+$, m/z) 446.1.

Example 155

Synthesis of (±) syn-ethyl 1-(2-(2,4-dioxo-1,2-dihydrothieno[2,3-d]pyrimidin-3(4H)-yl)ethyl)-4-(3-fluorophenyl)piperidine-3-carboxylate (Compound 7b)

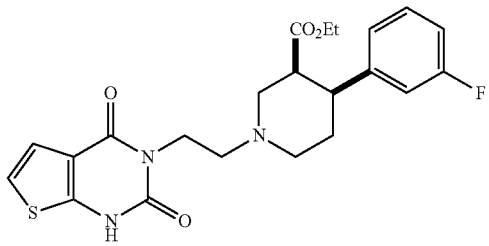 [SMILES: CCOC(=O)[C@@H]1CN(CCn2c(=O)[nH]c3sccc3c2=O)CC[C@@H]1c1cccc(F)c1]

Compound 7b was prepared from 4e and 1b as a white solid (137 mg, 60%) using the method of Example 153 above. mp=153.3-155.1° C.; $R_f$=0.10 (80% EtOAc/hexanes, 1% MeOH, 1% Et$_3$N); $^1$H NMR (300 MHz, CDCl$_3$) δ 7.26 (d, J=5.7 Hz, 1H), 7.22-7.17 (m, 1H), 7.04-6.96 (comp, 2H), 6.86 (dt, J=2.1, 7.8 Hz, 1H), 6.78 (d, J=5.7 Hz, 1H), 4.28-4.19 (m, 1H), 4.14-4.06 (m, 1H), 3.77 (q, J=7.2 Hz, 2H), 3.37 (d, J=8.7 Hz, 1H), 3.23 (d, J=11.1 Hz, 1H), 2.98-2.96 (m, 1H), 2.83 (dt, J=4.2, 12.0 Hz, 1H), 2.70 (t, J=7.2 Hz, 2H), 2.62-2.49 (comp, 2H), 2.24 (dt, J=3.0, 11.4 Hz, 1H), 1.82 (dd, J=3.3, 9.9 Hz, 1H), 0.97 (t, J=7.2 Hz, 3H); $^{13}$C NMR (75 MHz, CDCl$_3$) δ 172.2, 161.3 (d, J=242.8 Hz), 158.9, 152.3, 149.9, 146.1, 146.0, 129.4, 129.3, 123.3, 116.0, 114.6 (d, J=21.2 Hz), 112.9 (d, J=20.6 Hz), 60.0, 56.8, 55.4, 53.5, 46.2, 41.7, 38.1, 26.7, 14.0; Anal. Calcd for C$_{22}$H$_{24}$FN$_3$O$_4$S: C, 59.31; H, 5.43; N, 9.43; S, 7.20; F, 4.26. Found: C, 59.06; H, 5.52; N, 9.23; S, 7.05; F, 4.06; MS (APCl, [M+H]$^+$, m/z) 446.1.

Example 156

Synthesis of (±) syn-ethyl 1-(2-(2,4-dioxo-1,2-dihydrothieno[2,3-d]pyrimidin-3(4H)-yl)ethyl)-4-(4-(trifluoromethyl)phenyl)piperidine-3-carboxylate (Compound 7c)

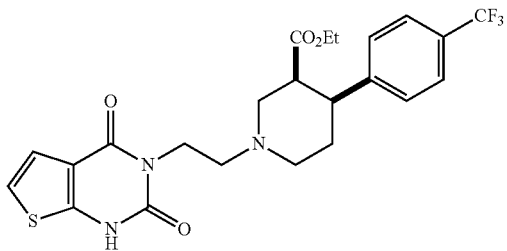 [SMILES: CCOC(=O)[C@@H]1CN(CCn2c(=O)[nH]c3sccc3c2=O)CC[C@@H]1c1ccc(C(F)(F)F)cc1]

Compound 7c was prepared from 4f and 1b as a white solid (142 mg, 52%) using the method of Example 153 above. mp=190.3-191.5° C.; $R_f$=0.10 (80% EtOAc/hexanes, 1% MeOH, 1% Et$_3$N); $^1$H NMR (300 MHz, CDCl$_3$) δ 7.50 (d, J=8.1 Hz, 2H), 7.37 (d, J=8.1 Hz, 2H), 7.26 (d, J=5.7 Hz, 1H), 6.77 (d, J=5.7 Hz, 1H), 4.31-4.21 (m, 1H), 4.15-4.07 (m, 1H), 3.75 (q, J=7.2 Hz, 2H), 3.40 (d, J=9.3 Hz, 1H), 3.27 (d, J=11.4 Hz, 1H), 3.01 (d, J=3.3 Hz, 1H), 2.92-2.85 (m, 1H), 2.75-2.66 (m, 2H), 2.63-2.58 (comp, 2H), 2.26 (dt, J=2.7, 11.1 Hz, 1H), 1.85 (dd, J=2.7, 12.6 Hz, 1H), 0.95 (t, J=7.2 Hz, 3H); $^{13}$C NMR (75 MHz, CDCl$_3$) δ 172.0, 158.8, 152.1, 149.6, 147.6, 128.4 (q, J=32.1 Hz), 128.0, 125.0, 124.4 (q, J=269.7 Hz), 123.4, 116.1, 116.0, 60.0, 57.1, 55.3, 53.6, 46.3, 42.0, 38.1, 26.5, 13.9; Anal. Calcd for C$_{23}$H$_{24}$F$_3$N$_3$O$_4$S: C, 55.75; H, 4.88; N, 8.48; S, 6.47; F, 11.50. Found: C, 55.36; H, 4.97; N, 8.34; S, 6.27; F, 11.21; MS (APCl, [M+H]$^+$, m/z) 496.1.

Example 157

Synthesis of syn-ethyl 1-(2-(2,4-dioxo-1,2-dihydrothieno[2,3-d]pyrimidin-3(4H)-yl)ethyl)-4-(3-(trifluoromethyl)phenyl)piperidine-3-carboxylate (Compound 7d)

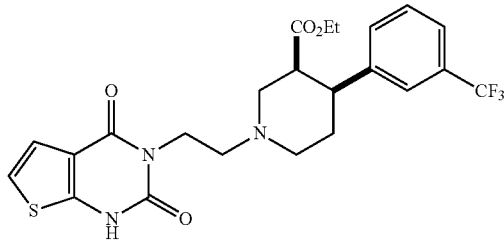 [SMILES: CCOC(=O)[C@@H]1CN(CCn2c(=O)[nH]c3sccc3c2=O)CC[C@@H]1c1cccc(C(F)(F)F)c1]

Compound 7d was prepared from 5g and 1b as a white solid (150 mg, 60%) using the method of Example 153 above. mp=153.5-156.5° C.; R$_f$=0.10 (80% EtOAc/hexanes, 1% MeOH, 1% Et$_3$N); $^1$H NMR (300 MHz, CDCl$_3$) δ 7.50-7.36 (comp, 4H), 7.26 (d, J=5.4 Hz, 1H), 6.78 (d, J=5.4 Hz, 1H), 4.30-4.21 (m, 1H), 4.14-4.06 (m, 1H), 3.76 (q, J=7.2 Hz, 2H), 3.40 (d, J=11.1 Hz, 1H), 3.27 (d, J=11.7 Hz, 1H), 2.99 (d, J=3.6 Hz, 1H), 2.87 (dt, J=3.9, 11.7 Hz, 1H), 2.74-2.67 (m, 2H), 2.64-2.54 (comp, 2H), 2.24 (dt, J=2.7, 11.4 Hz, 1H), 1.85 (d, J=12.9 Hz, 1H), 0.95 (t, J=7.2 Hz, 3H); $^{13}$C NMR (75 MHz, CDCl$_3$) δ 172.1, 158.8, 152.2, 149.6, 144.4, 131.1, 130.3 (q, J=31.5 Hz), 128.5, 124.5, 124.4 (q, J=270.2 Hz), 123.4, 123.0, 116.1, 116.0, 60.0, 57.0, 55.3, 53.6, 46.3, 42.0, 38.1, 26.6, 13.9; Anal. Calcd for C$_{23}$H$_{24}$F$_3$N$_3$O$_4$S: C, 55.75; H, 4.88; N, 8.48; S, 6.47; F, 11.50. Found: C, 56.01; H, 4.98; N, 8.37; S, 6.24; F, 11.26; MS (APCl, [M+H]$^+$, m/z) 496.1.

Example 158

Synthesis of (±) syn-ethyl 4-(4-fluorophenyl)-1-(2-(1-methyl-2,4-dioxo-1,2-dihydrothieno[2,3-d]pyrimidin-3(4H)-yl)ethyl)piperidine-3-carboxylate (Compound 8a)

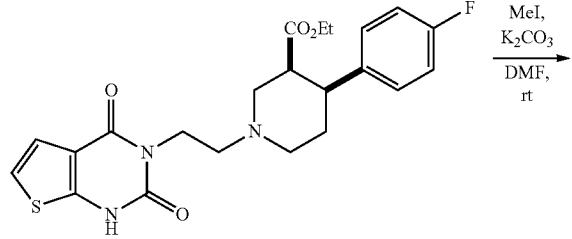

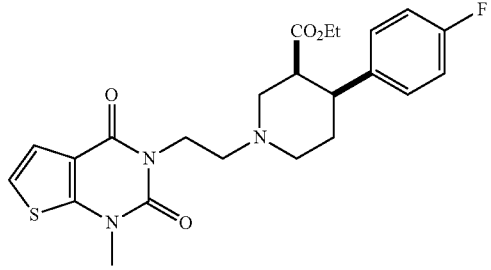

Compound 8a was prepared from 7a as a white solid (46 mg, 83%) using the method of Example 147 above. mp=132.5-133.8° C.; R$_f$=0.25 (80% EtOAc/hexanes, 1% Et$_3$N, 1% MeOH); $^1$H NMR (300 MHz, CDCl$_3$) δ 7.34 (d, J=5.7 Hz, 1H), 7.24 (dd, J=3.0, 5.4 Hz, 2H), 6.83 (d, J=5.7 Hz, 1H), 4.27-4.07 (m, 2H), 3.74 (dq, J=1.8, 7.2 Hz, 2H), 3.57 (s, 3H), 3.34 (d, J=9.9 Hz, 1H), 3.21 (d, J=10.5 Hz, 1H), 2.9 (q, J=3.3 Hz, 1H), 2.77 (dt, J=3.6, 11.7 Hz, 1H), 2.67-2.60 (comp, 2H), 2.58-2.50 (comp, 2H), 2.22 (dt, J=2.4, 11.1 Hz, 1H), 1.78 (dd, J=3.3, 12.9 Hz, 1H), 0.98 (t, J=7.2 Hz, 3H); $^{13}$C NMR (75 MHz, CDCl$_3$) δ 171.9, 161.3 (d, J=241.6 Hz), 158.4, 153.6, 151.1, 139.2, 129.1 (d, J=7.4 Hz), 124.7, 115.8, 115.6, 114.7 (d, J=21.2 Hz), 59.6, 57.0, 55.3, 53.8, 46.5, 41.7, 38.9, 35.0, 26.8, 14.0; Anal. Calcd for C$_{23}$H$_{26}$FN$_3$O$_4$S: C, 60.11; H, 5.70; N, 9.14; S, 6.98. Found: C, 59.88; H, 5.83; N, 8.89; S, 6.98; MS (APCl, [M+H]$^+$, m/z) 460.2.

Example 159

Synthesis of (±)-syn-Methyl 1-(2-(2,4-dioxo-1,2-dihydroquinazolin-3(4H),-yl)ethyl)-4-(4-fluorophenyl) piperidine-3-carboxylate (Compound 10a)

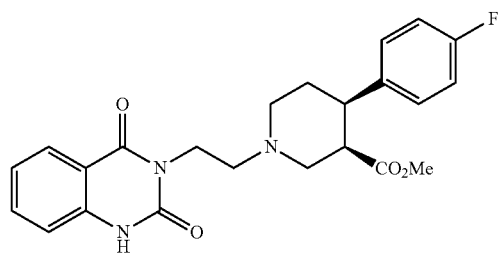 [SMILES: COC(=O)[C@H]1CN(CCn2c(=O)[nH]c3ccccc3c2=O)CC[C@H]1c1ccc(F)cc1]

Compound 10a was synthesized according to Scheme 1 above in 67% yield. MP(HCl)=191.5-193° C. $^1$H NMR (300 MHz, CDCl$_3$) δ 9.20 (s, 1H), 8.12 (d, J=7.98 Hz, 1H), 7.58 (td, J=1.4, 7.7 Hz, 1H), 7.24-7.15 (m, 4H), 7.04 (d, J=8.3 Hz, 1H), 6.93 (t, J=8.7 Hz, 2H), 4.35-4.07 (m, 2H), 3.37 (dd, J=2.9, 12.2 Hz, 1H), 3.28 (s, 3H), 3.26-3.16 (m, 1H), 2.93 (q, J=3.8 Hz, 1H), 2.86-2.74 (m, 1H), 2.74-2.65 (m, 2H), 2.62-2.49 (m, 2H), 2.24 (td, J=2.6, 11.1 Hz, 1H), 1.77 (dd, J=3.0, 12.7 Hz, 1H). $^{13}$C NMR (75 MHz, CDCl$_3$) δ 172.4, 162.5, 151.4, 139.0, 139.0, 138.5, 135.0, 129.2, 129.1, 128.6, 123.4, 115.0, 114.8, 114.7, 56.8, 55.3, 53.9, 50.9, 46.6, 41.7, 38.2, 26.8. Anal. (C$_{23}$H$_{24}$FN$_3$O$_4$; 1.2HCl; 1.5H$_2$O) C, H, N, Cl.

Example 160

Synthesis of (±)-syn-Isopropyl 1-(2-(2,4-dioxo-1,2-dihydroquinazolin-3(4H),-yl)ethyl)-4-(4-fluorophenyl)piperidine-3-carboxylate (Compound 10b)

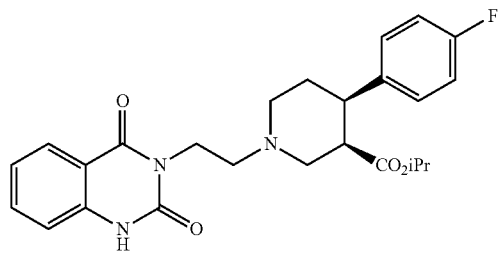

Compound 10b was synthesized as described in Scheme 1 above in 60% yield. MP (HCl)=157.5-159° C. $^1$H NMR (300 MHz, CDCl$_3$) δ ppm 9.42 (br. s., 1H), 8.11 (d, J=8.0 Hz, 1H), 7.59 (td, J=7.6, 1.1 Hz, 5H), 7.24-7.17 (m, 3H), 7.05 (d, J=8.0 Hz, 1H), 6.93 (t, J=8.8 Hz, 2H), 4.67 (quin, J=6.3 Hz, 1H), 4.36-4.21 (m, 1H), 4.15 (dt, J=12.8, 6.5 Hz, 1H), 3.34 (d, J=11.8 Hz, 1H), 3.22 (d, J=9.9 Hz, 1H), 2.94-2.76 (m, 2H), 2.69 (t, J=6.6 Hz, 2H), 2.57 (dd, J=11.6, 3.0 Hz, 2H), 2.25 (td, J=10.8, 2.3 Hz, 1H), 1.80 (d, J=10.2 Hz, 1H), 0.93 (d, J=2.8 Hz, 3H), 0.91 (d, J=2.5 Hz, 3H). $^{13}$C NMR (75 MHz, CDCl$_3$) δ 171.6, 162.4, 151.5, 138.6, 135.0, 129.2, 129.1, 128.5, 123.4, 114.8, 114.8, 114.7, 114.6, 67.0, 56.9, 55.4, 53.7, 46.5, 41.4, 38.3, 21.7, 21.5. Anal. (C$_{25}$H$_{28}$FN$_3$O$_4$.2HCl) C, H, N.

Example 161

Synthesis of Compound 12

Compound 12 was synthesized according to Scheme 2:

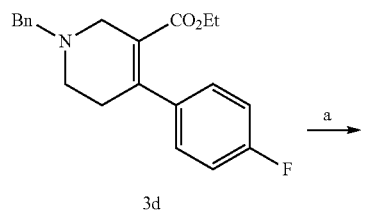

3d

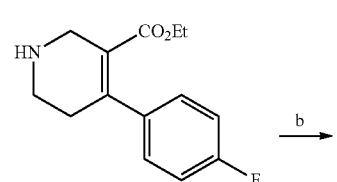

11

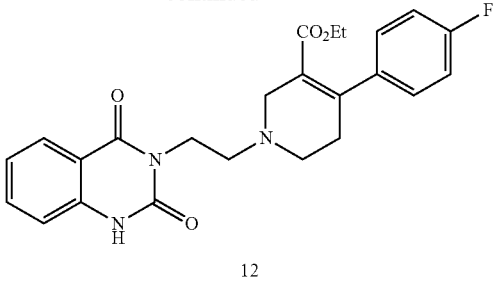

12 a) ACE-Cl 100° C., 2 hours
b) 1a, toulene 100° C. 24 hours

Example 162

Synthesis of Ethyl 4-(4-fluorophenyl)-1,2,5,6-tetrahydropyridine-3-carboxylate (Compound 11)

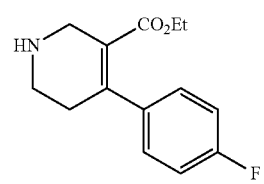 [SMILES: CCOC(=O)C1=C(c2ccc(F)cc2)CCNC1]

A round bottomed flask was charged with 3d (845 mg, 2.5 mmol), then α-chloroethyl chloroformate (ACE-Cl, 2.96 mL, 27.4 mmol) was added under nitrogen by syringe in one portion, and the reaction mixture stirred for 2 h at 100° C. Volatiles were removed in vacuo and the residue was treated with anhydrous EtOH (8.3 mL). The flask was then heated to reflux for 20 min and concentrated in vacuo. The solid residue was purified by flash chromatography using 0-10% MeOH/EtOAc (1% i-PrNH$_2$) to give 11 as a yellow oil (538 mg, 87%): R$_f$=0.22 (10% MeOH/CH$_2$Cl$_2$); $^1$H NMR (300 MHz, CDCl$_3$) δ 7.10 (dd, J=5.50, 8.81 Hz, 2H), 6.99 (t, J=8.81 Hz, 2H), 3.91 (q, J=7.15 Hz, 2H), 3.67 (t, J=2.75 Hz, 2H), 3.05 (t, J=5.78 Hz, 2H), 2.38 (spt, J=2.75 Hz, 2H), 0.91 (t, J=6.88 Hz, 3H).

Example 163

Synthesis of Ethyl 1-(2-(2,4-dioxo-1,2-dihydroquinazolin-3(4H)-yl)ethyl)-4-(4-fluorophenyl)-1,2,5,6-tetrahydropyridine-3-carboxylate (Compound 12)

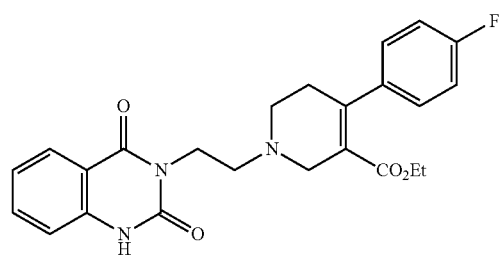 [SMILES: CCOC(=O)C1=C(c2ccc(F)cc2)CCN(CCn2c(=O)[nH]c3ccccc3c2=O)C1]

Compound 12 was prepared from 11 and 1a as a white solid (95 mg, 30%) using Scheme 2 above. mp=150-152° C.

(December); $R_f$=0.56 (10% MeOH/CH$_2$Cl$_2$); $^1$H NMR (301 MHz, CDCl$_3$) δ 10.31 (s, 1H), 8.09 (d, J=7.6 Hz, 1H), 7.60 (ddd, J=1.1, 7.2, 8.3 Hz, 1H), 7.21 (t, J=7.6 Hz, 1H), 7.04-7.14 (m, 3H), 6.98 (t, J=8.8 Hz, 2H), 4.34 (t, J=6.9 Hz, 2H), 3.93 (q, J=7.2 Hz, 2H), 3.50 (br. s., 2H), 2.89 (m, 4H), 2.53 (br. s., 2H), 0.93 (t, J=7.2 Hz, 3H); $^{13}$C NMR (75 MHz, DMSO-d$_6$) δ 167.4, 163.6, 162.5, 160.4, 150.7, 144.5, 140.0, 138.5, 135.6, 129.5, 129.4, 127.9, 126.2, 123.1, 115.7, 115.4, 115.2, 114.3, 60.3, 54.7, 53.5, 49.6, 38.1, 33.1, 14.0; Anal. Calcd for C$_{24}$H$_{24}$N$_3$O$_4$F.½H$_2$O: C, 64.56; H, 5.64; N, 9.41; F, 4.26. Found: C, 64.34; H, 5.40; N, 9.23; F, 4.39; MS (APCl, [M+H]$^+$, m/z) 438.2.

Example 164

Synthesis of Compounds 16 and 18

Compounds 16 and 18 were synthesized according to Scheme 3

Example 165

Synthesis of 3-(2-(4-(4-fluorophenyl)piperidin-1-yl)ethyl)quinazoline-2,4(1H,3H)-dione (Compound 16)

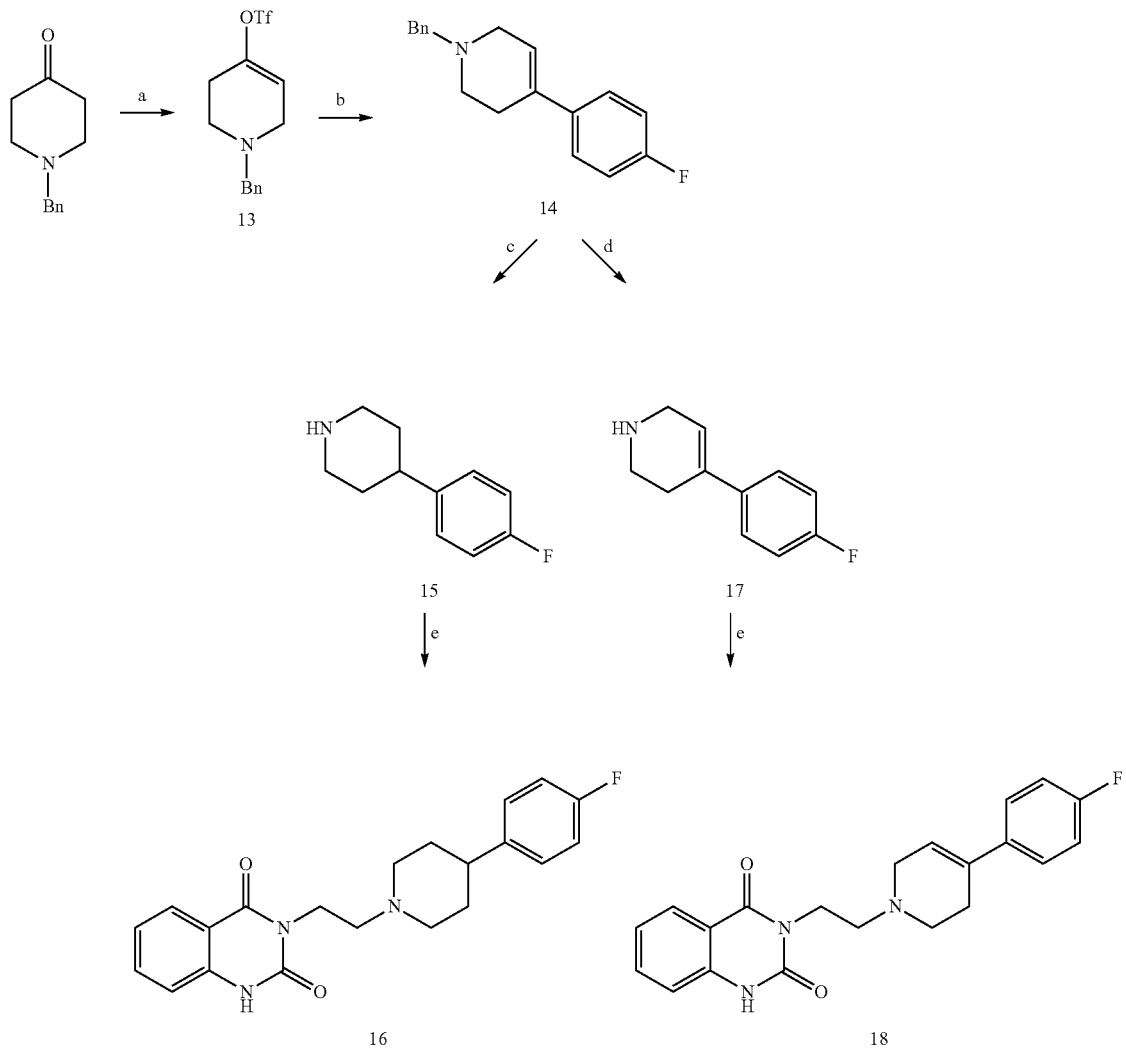

(a) NaHMDS, PhN(Tf)$_2$, THF, 0° C., 1.5 h;
(b) 4-fluorophenylboronic acid, Pd(PPh$_3$)$_4$, LiCl, K$_2$CO$_3$, 1,4-dioxane, 85° C.;
(c) Pd\C, H$_2$, EtOH, rt, 24 h;
(d) i) ACE-Cl, 100° C., 2 h; ii) EtOH, reflux, 30 min;
(e) 1a, toluene, 100° C., 24 h.

Compound 16 was prepared from 15 and 1a as a light-brown solid (170 mg, 86%) using Scheme 3 above. mp=263.0-264.0° C.; $^1$H NMR (300 MHz, DMSO-d$_6$) δ 11.44 (s, 1H), 7.93 (dd, J=1.0, 8.0 Hz, 1H), 7.65 (td, J=1.0, 7.7 Hz, 1H), 7.13-7.34 (m, 4H), 7.08 (t, J=8.8 Hz, 2H), 4.04 (t, J=7.2 Hz, 2H), 3.03 (d, J=11.0 Hz, 2H), 2.31-2.64 (m, 3H), 2.07 (t, J=11.0 Hz, 2H), 1.64-1.82 (m, 2H), 1.44-1.64 (m, 2H); $^{13}$C NMR (75 MHz, DMSO-d$_6$) δ 162.8, 162.4, 161.1, 150.7, 143.0, 140.0, 135.5, 129.0, 128.9, 127.9, 123.1, 115.6, 115.3, 114.3, 55.8, 54.4, 41.5, 38.2, 33.8; Anal. Calcd for $C_{21}H_{22}N_3O_2F$: C, 68.65; H, 6.04; N, 11.44; F, 5.17. Found: C, 68.36; H, 6.13; N, 11.04; F, 4.83; MS (APCl, [M+H]$^+$, m/z) 368.2.

Example 166

Synthesis of 3-(2-(4-(4-fluorophenyl)-5,6-dihydropyridin-1(2H)-yl)ethyl)quinazoline-2,4(1H,3H)-dione (Compound 18)

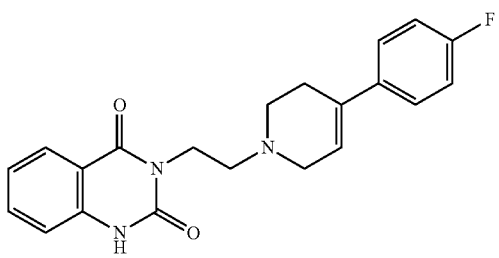 [SMILES: O=c1[nH]c2ccccc2c(=O)n1CCN1CC=C(c2ccc(F)cc2)CC1]

Compound 18 was prepared from 17 and 1a as a white solid (189 mg, 52%) using Scheme 3 above. mp=208.0° C. (December); R$_f$=0.20 (10% MeOH/CH$_2$Cl$_2$); $^1$H NMR (300 MHz, DMSO-d$_6$) δ 11.44 (br. s, 1H), 7.93 (d, J=8.0 Hz, 1H), 7.65 (t, J=7.7 Hz, 1H), 7.45 (dd, J=5.5, 8.8 Hz, 2H), 7.21 (d, J=7.7 Hz, 1H), 7.17 (d, J=8.0 Hz, 1H), 7.14 (t, J=8.8 Hz, 2H), 5.97-6.19 (m, 1H), 4.09 (t, J=6.9 Hz, 2H), 3.16 (d, J=2.5 Hz, 2H), 2.71 (t, J=5.5 Hz, 2H), 2.64 (t, J=6.9 Hz, 2H), 2.32-2.47 (m, 2H); $^{13}$C NMR (75 MHz, DMSO-d$_6$) δ 163.5, 162.5, 160.3, 150.7, 140.0, 137.1, 135.5, 133.5, 127.9, 127.0, 126.9, 123.1, 122.6, 115.7 (2 signals), 115.5, 114.3, 55.2, 53.4, 50.3, 38.1, 28.0; Anal. Calcd for $C_{21}H_{20}N_3O_2F$: C, 69.03; H, 5.52; N, 11.50; F, 5.20. Found: C, 68.79; H, 5.47; N, 11.35; F, 5.11; MS (APCl, [M+H]$^+$, m/z) 366.2.

Example 167

Synthesis of Compounds of Series 23

Compounds of Series 23 were prepared according to Scheme 4:

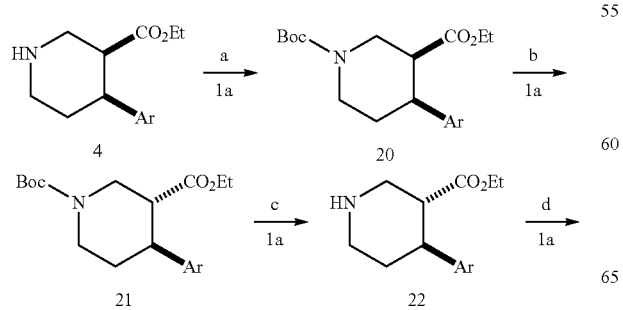

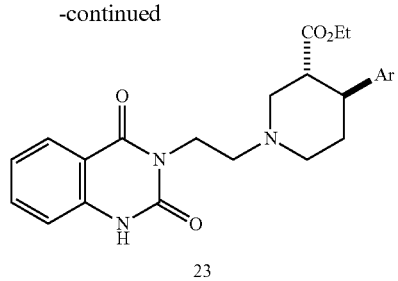

(a) (Boc)$_2$O, Et$_3$N, MeOH, 60° C., 30 min; (b) EtONa, EtOH, 70° C., 3 h;
(c) HCl 4M, 45 min;
(d) 1a, toluene, 100° C., 48 h.

Example 168

Synthesis of 1-tert-butyl 3α-ethyl 4α-(4-fluorophenyl)piperidine-1,3-dicarboxylate (Compound 20d)

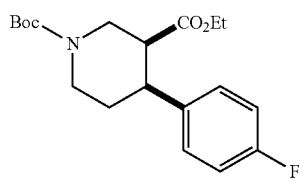 [SMILES: CCOC(=O)[C@@H]1CN(C(=O)OC(C)(C)C)CC[C@@H]1c1ccc(F)cc1]

A 50 mL round bottomed flask was charged with 5d (215 mg, 0.86 mmol), MeOH (5 mL), triethylamine (240 uL, 1.72 mmol) and a magnetic stir bar. Boc$_2$O (375 mg, 1.72 mmol) was added with vigorous stirring and the mixture was heated to 60° C. for 30 min. Volatiles were removed in vacuo and the residue was partitioned between CH$_2$Cl$_2$ (15 mL) and brine (5 mL). The layers were separated, and the aqueous layer was further extracted with CH$_2$Cl$_2$ (2×10 mL). The combined organic layers were dried (MgSO$_4$), filtered, and concentrated, then purified by flash chromatography eluting with 0-100% EtOAc/hexanes to give 20d (214 mg, 71%): R$_f$=0.75 (50% EtOAc/hexanes, 1% Et$_3$N); $^1$H NMR (300 MHz, CDCl$_3$) δ 7.19 (dd, J=5.5, 8.8 Hz, 1H), 6.95 (t, J=8.8 Hz, 2H), 4.09-4.64 (m, 2H), 3.92 (q, J=7.2 Hz, 2H), 3.01-3.29 (m, 1H), 2.71-3.02 (m, 2H), 2.48-2.71 (m, 1H), 1.54-1.85 (m, 2H), 1.47 (s, 9H), 1.04 (t, J=7.2 Hz, 3H); $^{13}$C NMR (75 MHz, CDCl$_3$) δ 171.6, 163.3, 160.0, 154.5, 138.3, 129.1, 129.0, 115.2, 115.0, 79.7, 60.2, 49.1, 45.7, 43.6, 42.5, 28.5, 25.9, 14.1.

Example 169

Synthesis of 1-tert-butyl 3β-ethyl 4α-(4-fluorophenyl)piperidine-1,3-dicarboxylate (Compound 21d)

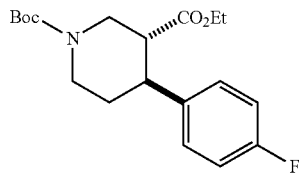 [SMILES: CCOC(=O)[C@H]1CN(C(=O)OC(C)(C)C)CC[C@@H]1c1ccc(F)cc1]

A 50 mL round bottomed flask was charged with 20d (194 mg, 0.55 mmol), EtOH (5 mL), and NaOEt (56 mg, 0.83 mmol), then heated to 70° C. for 3 h in an oil bath. The solution was concentrated in vacuo and purified by flash chromatography eluting with 0-30% EtOAc/hexanes to give pure (trans) 21d (137 mg, 71%): $R_f$=0.87 (50% EtOAc/hexanes, +1% Et$_3$N); $^1$H NMR (300 MHz, CDCl$_3$) δ 7.13 (dd, J=5.2, 8.8 Hz, 2H), 6.96 (t, J=8.8 Hz, 2H), 4.35 (br. s, 1H), 4.24 (br. s., 1H), 3.89 (q, J=7.2 Hz, 2H), 2.72-3.04 (m, 3H), 2.47-2.71 (m, 1H), 1.69-1.87 (m, 1H), 1.56-1.69 (m, H), 1.48 (s, 9H), 0.95 (t, J=7.2 Hz, 3H); $^{13}$C NMR (75 MHz, CDCl$_3$) δ 172.5, 163.4, 160.2, 154.5, 138.6, 129.0, 128.9, 115.5, 115.2, 80.2, 60.4, 49.1, 46.3, 45.1, 44.1, 32.9, 28.5, 14.0.

Example 170

Synthesis of Ethyl 4α-(4-fluorophenyl)piperidine-3β-carboxylate (Compound 22d)

Compound 21d (126 mg, 0.36 mmol) was taken up in HCl (4M in dioxane, 6.3 mL) under N$_2$. The solution was stirred 45 min, and neutralized with solid NaHCO$_3$ (4.60 g). The reaction mixture was diluted with water (20 mL), and extracted with CH$_2$Cl$_2$ (3×20 mL). The combined organic layers were dried (MgSO$_4$), concentrated. The residue was purified by flash chromatography eluting with 0-10% MeOH/CH$_2$Cl$_2$ (1% Et$_3$N) to give 22d (90 mg, 100%); $^1$H NMR (300 MHz, CDCl$_3$) δ 7.15 (dd, J=5.2, 8.8 Hz, 2H), 6.94 (t, J=8.8 Hz, 2H), 3.87 (q, J=7.2 Hz, 2H), 3.33 (dd, J=3.6, 11.8 Hz, 1H), 3.10-3.25 (m, 1H), 2.62-2.95 (m, 4H), 2.25 (br. s, 1H), 1.74-1.92 (m, 1H), 1.62 (dq, J=4.1, 12.6 Hz, 1H), 0.95 (t, J=7.2 Hz, 3H).

Example 171

Synthesis of Ethyl 1-(2-(2,4-dioxo-1,2-dihydroquinazolin-3(4H)-yl)ethyl)-4α-(4-fluorophenyl) piperidine-3β-carboxylate (Compound 23d)

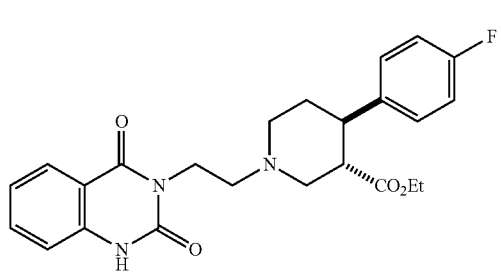 [SMILES: CCOC(=O)[C@@H]1CN(CCn2c(=O)[nH]c3ccccc3c2=O)CC[C@H]1c1ccc(F)cc1]

Compound 23d was prepared from 22d and 1a as an off-white solid (68 mg, 47%) using the general procedure described above. mp=195.0-197.0° C.; $R_f$=0.54 (10% MeOH/CH$_2$Cl$_2$); $^1$H NMR (300 MHz, DMSO-d$_6$) δ 11.47 (s, 1H), 7.94 (dd, J=1.1, 8.0 Hz, 1H), 7.66 (ddd, J=1.4, 7.4, 8.0 Hz, 1H), 7.14-7.30 (m, 4H), 7.07 (t, J=8.8 Hz, 2H), 4.04 (t, J=6.9 Hz, 2H), 3.82 (qd, J=1.7, 7.2 Hz, 2H), 3.18 (d, J=10.7 Hz, 1H), 3.02 (d, J=10.7 Hz, 1H), 2.65-2.78 (m, 2H), 2.60 (t, J=6.9 Hz, 2H), 2.07-2.27 (m, 2H), 1.51-1.75 (m, 2H), 0.87 (t, J=7.2 Hz, 3H); $^{13}$C NMR (75 MHz, DMSO-d$_6$) δ 172.9, 163.0, 162.5, 159.8, 150.7, 140.2, 140.0, 135.6, 129.7, 129.6, 127.9, 123.1, 115.7, 115.6, 115.3, 114.3, 60.1, 56.2, 55.2, 53.9, 49.1, 44.7, 38.0, 33.3, 14.3; Anal. Calcd for C$_{24}$H$_{26}$N$_3$O$_4$F: C, 65.59; H, 5.96; N, 9.56; F, 4.32. Found: C, 65.52; H, 6.09; N, 9.42; F, 4.24; MS (APCl, [M+H]$^+$, m/z) 440.2.

Example 172

Synthesis of 1-methylquinazoline-2,4(1H,3H)-dione

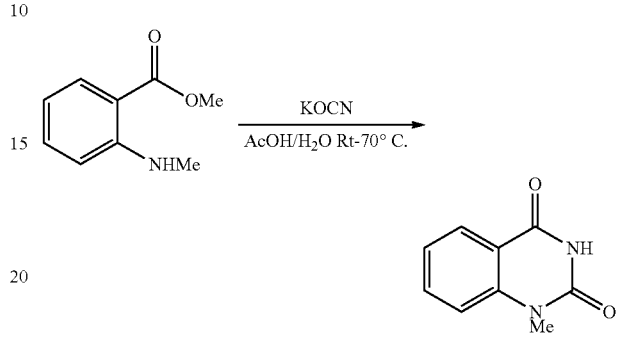

To a stirred mixture of Methyl N-Methyl anthranilate (1.46 mL, 10 mmol) in glacial acetic acid (10 mL) was added KOCN (975 mg, 12 mmol) in 3 mL of H$_2$O. The solution was stirred at room temperature overnight and then heated to 70° C. for 3 hours. The reaction was cooled to 0° C. and then filtered. The white solid was washed with cold ethanol and dried. The product was collected as a white solid (1.46 g) in 80% yield. $^1$H NMR (300 MHz, DMSO-d$_6$) δ 11.53 (br. s., 1H), 7.97 (d, J=7.71 Hz, 1H), 7.88-7.64 (m, 1H), 7.38 (d, J=8.81 Hz, 1H), 7.25 (t, J=7.57 Hz, 1H) 3.42 (s, 3H).

Example 173

Synthesis of 3-(2-hydroxyethyl)-1-methylquinazoline-2,4(1H,3H)-dione

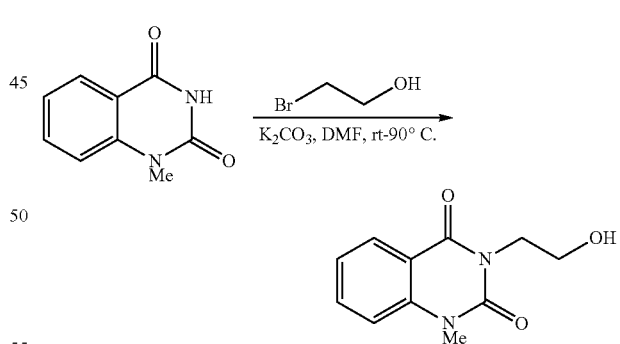

To a stirred solution of 1-methylquinazoline-2,4(1H,3H)-dione (1.40 g, 7.95 mmol) and K$_2$CO$_3$ (2.2 g, 15.9 mmol) in dry DMF (10 mL) under a positive stream of nitrogen was added 2-Bromoethanol (0.62 mL, 8.75 mmol). The solution was heated to 90° C. for 3 hours. The reaction mixture was cooled to room temperature, filtered and concentrated. The crude oil was diluted with EtOAc (20 mL) and washed with brine (3×~50 mL). The organic layer was dried over Na$_2$SO$_4$ and concentrated to provide the title compound (1.13 g) in 65% yield. $^1$H NMR (300 MHz, DMSO-d$_6$) □ 8.03 (dd, J=1.65, 7.98 Hz, 1H), 7.76 (ddd, J=1.65, 7.09, 8.60 Hz, 1H), 7.43 (d, J=8.26 Hz, 1H), 7.28 (t, J=7.57 Hz, 1H), 4.76 (t, J=6.05, Hz, 1H), 4.03 (t, J=6.60 Hz, 2H), 3.55 (q, J=6.51 Hz, 2H), 3.50 (s, 3H).

Example 174

Synthesis of 2-(1-methyl-2,4-dioxo-1,2-dihydroquinazolin-3(4H)-yl)acetaldehyde (Compound SM B)

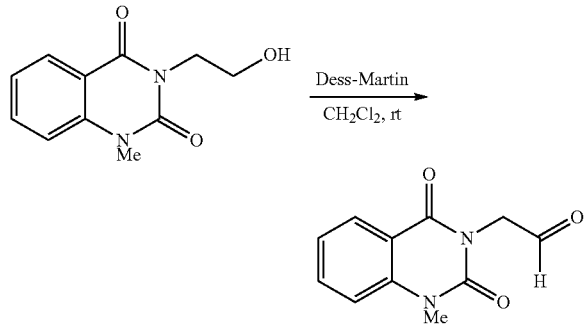

To a solution of 3-(2-hydroxyethyl)-1-methylquinazoline-2,4(1H,3H)-dione (500 mg, 2.27 mmol) in dry CH$_2$Cl$_2$ was added Dess-Martin periodirane (1.45 g, 3.41 mmol) under a positive stream of N$_2$. The solution was stirred overnight at room temperature. The reaction was then quenched by the addition of an aqueous sat. NaHCO$_3$ solution and extracted with CH$_2$Cl$_2$ (3×20 mL). The combined organic extracts were dried over Na$_2$SO$_4$ and concentrated. The crude product was purified on a silica gel column (50-100% EtOAc/Hexanes) to give pure title compound (410 mg) in 83% yield. $^1$H NMR (300 MHz, DMSO-d$_6$) δ 9.60 (s, 1H), 8.05 (dd, J=1.65, 7.71 Hz, 1H), 7.82 (ddd, J=1.79, 7.15, 8.67 Hz, 1H), 7.50 (d, J=8.26 Hz, 1H), 7.40-7.27 (m, 1H), 4.82 (s, 2H), 3.53 (s, 3H).

Example 175

Synthesis of -(2-(4-(4-fluorophenyl)-3-propionyl-5,6-dihydropyridin-1(2H)-yl)ethyl)-1-methylquinazoline-2,4(1H,3H)-dione

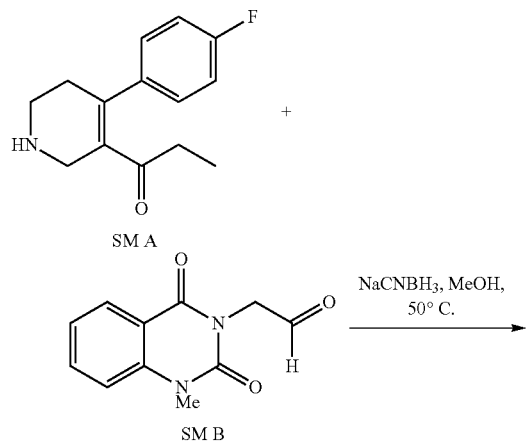

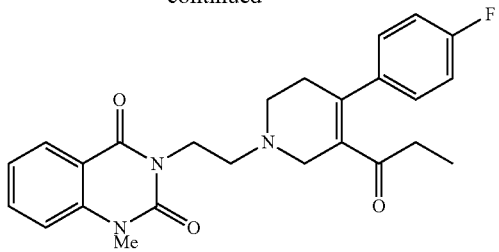

To a dry 25 mL round bottomed flask under a nitrogen atmosphere was added SM A (25 mg, 0.107 mmol) and SM B (25.6 mg, 0.118 mmol) followed by dry MeOH (2 mL). NaCNBH$_3$ (8.1 mg, 0.128 mmol) was then added to the solution and the mixture was heated to 50° C. for 2 hours. The solution was diluted with CH$_2$Cl$_2$ and the organic layer was washed with brine. The organic layer was dried over Na$_2$SO$_4$ and concentrated. The crude product was purified on a silica gel column (50-100% EtOAc/Hexanes) to provide the title compound as a white solid (45.4 mg) in 97% yield. $^1$H NMR (300 MHz, CDCl$_3$) δ 8.20 (dd, J=1.79, 7.84 Hz, 1H), 7.67 (ddd, J=1.65, 7.09, 8.60 Hz, 1H), 2.28-7.16 (m, 2H), 7.16-7.06 (m, 2H), 7.00 (t, J=8.67 Hz, 2H), 4.31 (t, J=6.88, 6.88 Hz, 2H), 3.59 (s, 3H), 3.35 (t, J=2.61 Hz, 2H), 2.74-2.90 (m, 4H), 2.53 (sept., J=3.03 Hz, 2H), 1.96 (q, J=7.25 Hz, 2H), 0.79 (t, J=7.29 Hz, 3H).

All documents, including patents, patent application and publications cited herein, including all documents cited therein, tables, and drawings, are hereby expressly incorporated by reference in their entirety for all purposes.

While the foregoing written description of the compounds, uses, and methods described herein enables one of ordinary skill in the art to make and use the compounds, uses, and methods described herein, those of ordinary skill in the art will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

The invention claimed is:
1. A method for treating a subject having a methamphetamine (MA) addiction comprising:
   administering to the subject a therapeutically effective amount of a pharmaceutical composition comprising a compound with the formula:

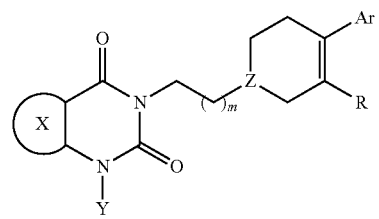

wherein X is a substituted or unsubstituted 5- or 6-membered aryl or substituted or unsubstituted 5- or 6-membered heteroaryl,
Z is N or CH,
m is 1, 2, or 3, Ar is a substituted or unsubstituted 5- or 6-membered aryl or a substituted or unsubstituted 5- or 6-membered heteroaryl, R is H, ethyl ester, isopropyl ester, —C(O)-alkyl, or substituted or unsubstituted 5-membered heteroaryl, Y is H, substituted or unsubstituted alkyl, substituted or unsubstituted aryl, or substituted or unsubstituted heteroaryl;

or a pharmaceutically acceptable salt, solvate, hydrate, stereoisomer, mixture of stereoisomers, crystal form, or isotopomer thereof.

2. The method of claim 1, wherein the pharmaceutical composition reduces a pathological effect or symptom of the MA addiction.

3. The method of claim 1, wherein the pharmaceutical composition binds vesicular monoamine transporter 2 (VMAT2).

4. The method of claim 1, wherein the pharmaceutical composition inhibits or substantially inhibits vesicular monoamine transporter 2 (VMAT2) function.

5. The method of claim 1, wherein the pharmaceutical composition reduces a craving for MA.

6. The method of claim 1, further comprising identifying a subject having an MA addiction.

7. The method of claim 1, wherein the subject is a human or a mammal.

8. The method of claim 1, wherein R is ethyl ester, isopropyl ester, —C(O)-alkyl, or substituted or unsubstituted 5-membered heteroaryl.

9. The method of claim 8, wherein R is ethyl ester.

10. The method of claim 8, wherein R is —C(O)-alkyl.

11. The method of claim 1, wherein Ar is phenyl, substituted phenyl, pyrrolyl, substituted pyrrolyl, pyridinyl, substituted pyridinyl, thiophene-yl, substituted thiophene-yl, or [1,4]-dioxinyl.

12. The method of claim 1, wherein the structure of the compound is:

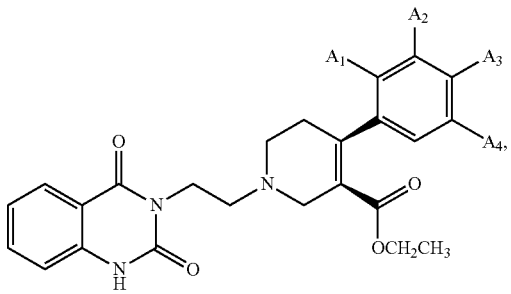

and
wherein $A_1$, $A_2$, $A_3$, and $A_4$, are independently H, alkyl, substituted alkyl, aryl, substituted aryl, halo, alkoxy, haloalkyl, haloalkoxy, ester, keto, hydroxyl, amino, substituted amino, amido, or nitro.

13. The method of claim 12, wherein $A_1$, $A_2$, $A_3$, and $A_4$ are independently H, methyl, ethyl, isopropyl, [1,4]dioxin-5-yl, fluoro, chloro, trifluoromethyl, amino, dimethylamino, methylamido, nitro, azo, benzyl, 2-phenyl ethyl, pyrrolyl, ethyl ester, 1-hydroxyethyl, hydroxyl, methoxy, trifluoromethoxy, or tert-butoxycarbonylamino.

14. The method of claim 12, wherein $A_1$ and $A_2$ are H, and $A_3$ and $A_4$ are independently H, fluoro, or trifluoromethyl.

15. The method of claim 1, wherein the structure of the compound is:

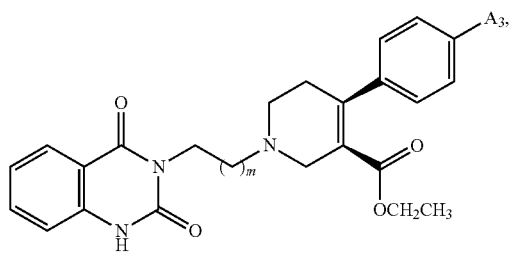

and
wherein $A_3$ is halo, and m is 2 or 3.

16. The method of claim 15, wherein $A_3$ is fluoro.

17. The method of claim 1, wherein the structure of the compound is:

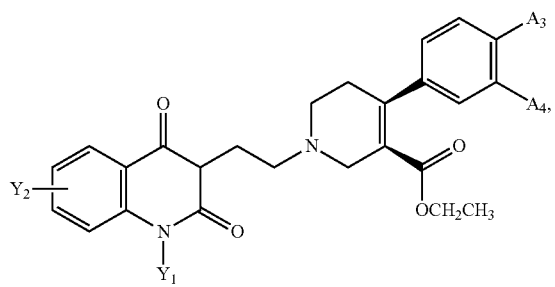

wherein $Y_1$ is H, methyl, ethyl, or 2-benzylethyl, wherein $Y_2$ is H or halo, and wherein $A_3$ and $A_4$ are independently H or halo.

18. The method of claim 1, wherein the structure of the compound is:

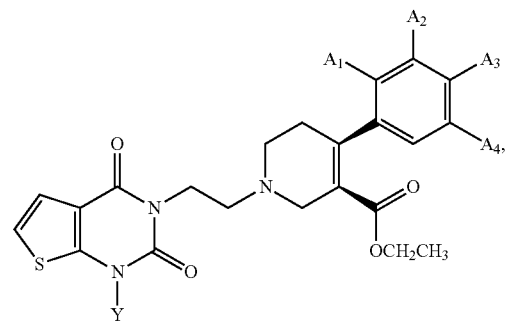

wherein $A_1$, $A_2$, $A_3$, and $A_4$ are independently H, halo, or haloalkyl, and wherein Y is H or alkyl.

19. The method of claim 18, wherein Y is H, $A_1$ and $A_2$ are H, and $A_3$ and $A_4$ are independently H, fluoro, or trifluoromethyl.

* * * * *